US007906104B2

(12) United States Patent
Chessler et al.

(10) Patent No.: US 7,906,104 B2
(45) Date of Patent: Mar. 15, 2011

(54) METHODS FOR DETECTING PANCREATIC BETA-ISLET CELLS AND DISEASES THEREOF

(75) Inventors: Steven D. Chessler, San Diego, CA (US); Arthur T. Suckow, Chula Vista, CA (US)

(73) Assignee: The Regents of the University of California, Oakland, CA (US)

( * ) Notice: Subject to any disclaimer, the term of this patent is extended or adjusted under 35 U.S.C. 154(b) by 70 days.

(21) Appl. No.: 11/997,872

(22) PCT Filed: Aug. 4, 2006

(86) PCT No.: PCT/US2006/030644

§ 371 (c)(1), (2), (4) Date: Mar. 7, 2008

(87) PCT Pub. No.: WO2007/019406

PCT Pub. Date: Feb. 15, 2007

(65) Prior Publication Data

US 2009/0068199 A1 Mar. 12, 2009

Related U.S. Application Data

(60) Provisional application No. 60/706,133, filed on Aug. 4, 2005.

(51) Int. Cl.

| | |
|---|---|
| ***A61K 49/16*** | (2006.01) |
| ***A61B 5/055*** | (2006.01) |
| ***G01N 33/53*** | (2006.01) |
| ***G01N 33/533*** | (2006.01) |
| ***G01N 33/534*** | (2006.01) |
| ***G01N 33/535*** | (2006.01) |
| ***G01N 33/563*** | (2006.01) |
| ***G01N 33/574*** | (2006.01) |
| ***G01N 33/577*** | (2006.01) |
| *C07K 16/28* | (2006.01) |
| *C12P 21/08* | (2006.01) |

(52) U.S. Cl. .................... 424/9.34; 424/9.3; 424/9.323; 424/9.6; 424/9.341; 530/387.3; 530/387.9; 530/388.1; 530/387.1; 530/388.15; 435/7.1; 435/7.2; 435/7.21; 435/7.23

(58) Field of Classification Search ....................... None
See application file for complete search history.

(56) References Cited

OTHER PUBLICATIONS

Fujita E et al. Distribution of RA175/TSLC1/SynCAM, a member of the immunoglobulin superfamily, in the developing nervous system. Feb. 2005; 154(2):199-209.*

Bolliger MF et al. Identification of a novel neuroligin in humans which binds to PSD-95 and has a widespread expression. Biochem J. 2001; 356:581-588.*

Song J-Y et al. Neuroligin 1 is a postsynaptic cell-adhesion molecule of excitatory synapses. Proc. Natl. Acad. Sci. USA, 1999; 96:1100-1105.*

X-linked neuroligin 4 [Homo sapiens] protein sequence. NCBI reference sequence NP_065793.1. Accessed on Dec. 3, 2009.*

Fukahi K et al. Aberrant expression of Neuropilin-1 and -2 in human pancreatic cancer cells. Clin Cancer Res. Jan. 2004; 10:581-590.*

Parikh AA et al. Expression and regulation of the novel vascular endothelial growth factor receptor Neuropilin-1 by epidermal growth factor in human pancreatic carcinoma. Cancer, 2003; 98:720-729.*

Suckow AT et al. Expression of Neurexin, Neuroligin, and their cytoplasmic binding partners in the pancreatic beta-cells and the involvement of Neuroligin in insulin secretion. Endocrinology. 2008; 148:6006-6017.*

* cited by examiner

*Primary Examiner* — Elizabeth C. Kemmerer
*Assistant Examiner* — Kimberly A. Ballard
(74) *Attorney, Agent, or Firm* — RatnerPrestia

(57) ABSTRACT

The role of synaptic adhesion molecules in human cell development and function is largely unknown. This invention provides methods to study β-cell function in native tissue through the use of novel adhesion and migrations assays. Through the use of these assays, the inventors have been able to for the first time describe the contribution of SAMs to human β-cell adhesion, spreading, and motility. Furthermore, the inventors have used the results of these assays to develop methods for detection, treatment, and prevention of diseases related to the pancreas.

17 Claims, 16 Drawing Sheets

Neuroligin 2 (and glucagon)

Neurexin 1: preliminary immunohistochemistry

- preliminary immunofluorescence shows staining to be beta-cell specific (ab: SC-14334)

FIG. 1B

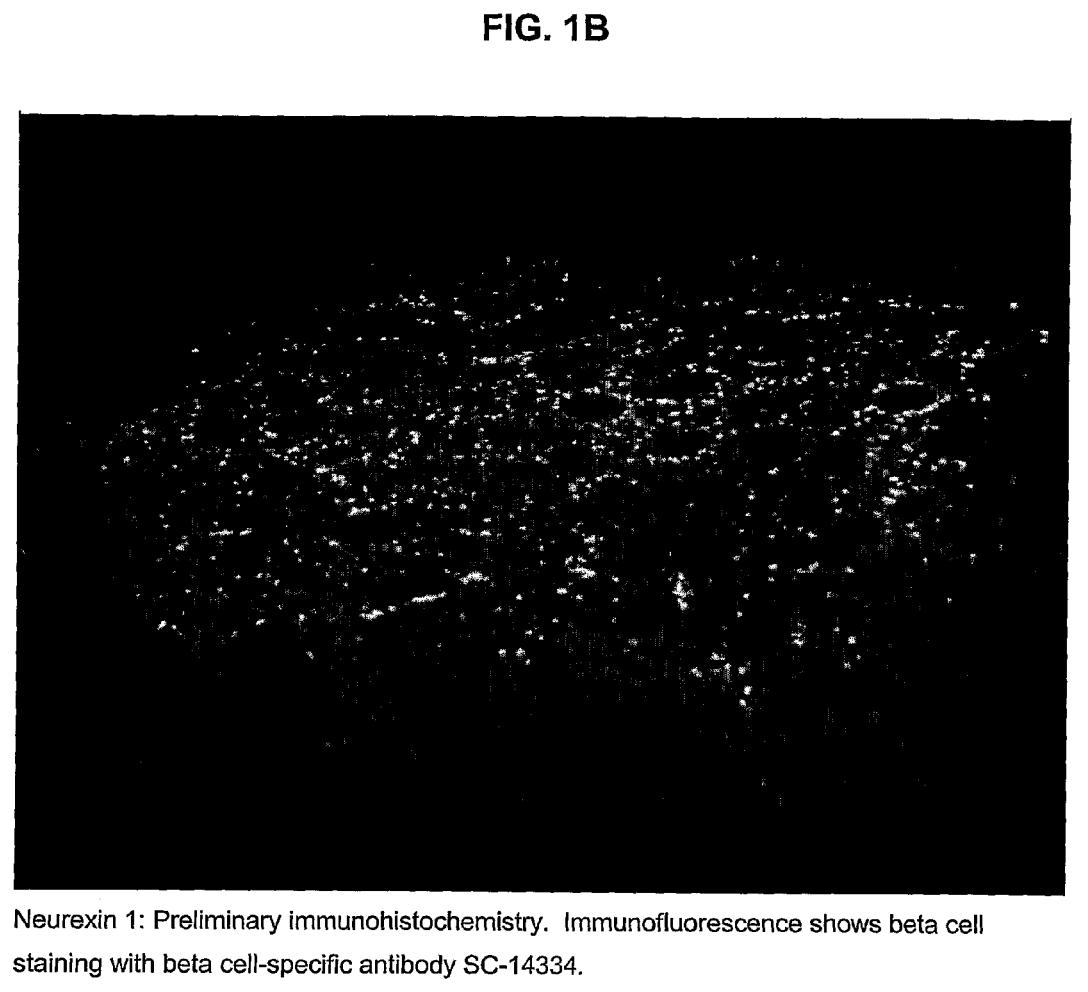

Neurexin 1: Preliminary immunohistochemistry. Immunofluorescence shows beta cell staining with beta cell-specific antibody SC-14334.

SynCam: Islet Specificity

PCR

- Human islet +
- INS-1 cells +
- Human fetal pancreas +

Beta cell expression of NL-1

NL-1 *in* INS-1 cells.

NL-1: Rat Pancreas

Neurexin-1 (Left, rat pancreas, Right INS-1 cells)

SynCam: INS-1

METHODS FOR DETECTING PANCREATIC BETA-ISLET CELLS AND DISEASES THEREOF

CROSS-REFERENCE TO RELATED APPLICATIONS

This application is a U.S. National of PCT/US2006/030644 filed on Aug. 4, 2006, which claims priority from U.S. Provisional Application Ser. No. 60/706,133 filed on Aug. 4, 2005, and which are incorporated herein by reference in their entirety.

STATEMENT REGARDING FEDERALLY SPONSORED RESEARCH OR DEVELOPMENT

This invention was made with Government support under National Institutes of Health Grant DK02944. The Government has certain rights in the invention.

INCORPORATION-BY-REFERENCE OF MATERIAL SUBMITTED ON A COMPACT DISC

Not Applicable.

INCORPORATION-BY-REFERENCE OF SEQUENCE LISTING

The Sequence Listing, which is a part of the present disclosure, includes a computer file "5014987-87_ST25.TXT" generated by U.S. Patent & Trademark Office PatentIn Version 3.5 software comprising nucleotide and/or amino acid sequences of the present invention. The subject matter of the Sequence Listing is incorporated herein by reference in its entirety.

BACKGROUND OF THE INVENTION

1. Field of the Invention

The present invention relates generally to synaptic adhesion molecules and their role in pancreatic islet β-cells and, in particular, methods for imaging, isolating, and detecting the islets as well as inhibiting, treating and reversing diseases related to β-cell and pancreatic abnormalities.

2. Description of Related Art

Synaptic adhesion molecules are a disparate family of cell surface proteins involved in the adhesion of cells at synaptic junctions. The main constituents of synaptic adhesion molecules are members of the cadherin family and immunoglobulin superfamily. Synaptic adhesion molecules are thought to serve a plethora of functions, ranging from adhesion and cellular signaling to synaptic differentiation. Recent research has identified a synaptic adhesion molecule, SynCAM, as a molecule located at the synaptic junction. Two other known groups of synaptic adhesion molecules include neuroligins (e.g., neuroligin 1, neuroligin 2, neuroligin 3, neuroligin 4X and neuroligin 4Y) and neurexins (e.g., neurexin 1α, neurexin 2α, neurexin 3α, neurexin 1β, neurexin 2β, and neurexin 3β). The sequences of these polypeptides are known in the art and are available on the Internet at National Center for Biotechnology Information ("NCBI").

As the incidence of diabetes increases, so too does the need for more improved diagnostic and treatment modalities. Islet β-cell transplantation has emerged as a key therapy in the treatment of type 1 diabetes. Although β-cell transplantation has met with some success, the treatment is fraught with numerous problems. Although, β-cell transplantation is initially effective for many patients, over time the recipient's ability to maintain insulin independence diminishes. The causes of this loss of independence are not known although a loss of β-cell mass is believed to be one cause. Because distinct β-cell specific cell surface proteins have not heretofore been identified, this has made determining the exact cause difficult.

The ability to measure islet β-cell mass in vivo is of great interest to researchers and clinicians alike. Cell-surface proteins specific enough to be targeted for imaging and treatment have not heretofore been obtained which has hindered research in the areas of pancreatic cancer and, especially, diabetes mellitus. There are no known cell surface markers expressed in islet, β-cells of the pancreas that are specific enough to β-cells to be used for imaging or treatment.

BRIEF SUMMARY OF THE INVENTION

Accordingly, it is an object of the invention to overcome these and other problems associated with the related art. These and other objects, features and technical advantages are achieved by targeting synaptic adhesion molecules expressed on islet β-cells, which include neuroligin 1, neuroligin 2, neuroligin 3, neuroligin 4X, neuroligin 4Y, neurexin 1α, neurexin 2α, neurexin 3α, neurexin 1β, neurexin 2β, neurexin 3β, SynCam, Thy-1, and neuronal pentraxin (hereinafter "SAMs") and/or neuropilin 1 (sequences available at NCBI, supra) on the surface of β-cells, particularly pancreatic islet, β-cells.

In accordance with a further aspect of the present invention, a method is provided for treating pancreatic disease such as diabetes mellitus or islet cell carcinoma by administering to a mammal in need thereof a therapeutically effective amount of an agent that selectively binds SAMs and/or neuropilin 1. The agent provided may be any of the classes of molecules and delivered by the various routes described herein.

In accordance with yet another aspect of the present invention, a method is provided for treatment of autoimmune diabetes mellitus by administering to a mammal in need thereof a therapeutically effective amount of an agent capable of binding a component of the immunologic synapse. The component of the immunologic synapse targeted may be selected from the group consisting of SynCam, Thy-1 and neuropilin 1.

This invention provides a method for imaging, targeting, detecting, identifying, and separating cells expressing SAMs and/or neuropilin 1, particularly pancreatic islet β-cells comprising treating cells with an agent capable of specifically binding to pancreatic islet β-cells. In one aspect of the present invention, the mammal is human. In accordance with a further aspect of the invention the agent is selected from the group consisting of an antibody, antibody fragment, polypeptide, polynucleotide, and aptamer. In one aspect of the present invention, the agent is an antibody. The antibody could be selected from the group consisting of a polyclonal, monoclonal, chimeric, or single chain antibody. The antibody fragments could consist of Fab fragments or Fab expression library.

In yet another aspect of the current invention the agent can be a conjugate of a first compound and a second compound. For the purpose of detecting cells expressing SAMs and/or neuropilin 1 or treating a disease, the second agent can be a radioisotope or paramagnetic ion. In yet another aspect of the invention the disease to be treated can be diabetes, in particular diabetes mellitus, and more particularly autoimmune diabetes mellitus, pancreatic cancer, particularly metastatic pancreatic cancer.

In accordance with a further aspect of the present invention, agents targeting SAMs and/or neuropilin 1 on the surface of islet, β-cells may be used to determine β-cell mass. β-cell mass may be monitored over time by repeated imaging using the methods of the present invention.

In accordance with yet another aspect of the present invention, a method is provided for identifying agents capable of binding SAMs and/or neuropilin 1 by providing an immobilized SAMs and/or neuropilin 1 and incubating the immobilized molecule in the presence of a sample to be assayed. The immobilize molecule is subsequently removed from the sample and it is determined whether an agent is bound thereto.

In accordance with yet another aspect of the present invention, a method is provided for detecting β-cell tumors by administering to a mammal in need thereof an effective amount of an agent capable of binding SAMs and/or neuropilin 1, imaging the β-cells of the mammal, and determining the presence or absence of tumors by use of the images generated. Over time, the progression or regression of a tumor may be monitored by this method.

In yet another aspect of the present invention, kits are provided containing the necessary reagents to carry out the methods as described above and further herein.

BRIEF DESCRIPTION OF THE FIGURES

FIG. 1B: Depiction of another view of neurexin 1 staining to be β-cell specific.

DETAILED DESCRIPTION OF THE INVENTION

Abbreviations and Definitions

Figure 1A:
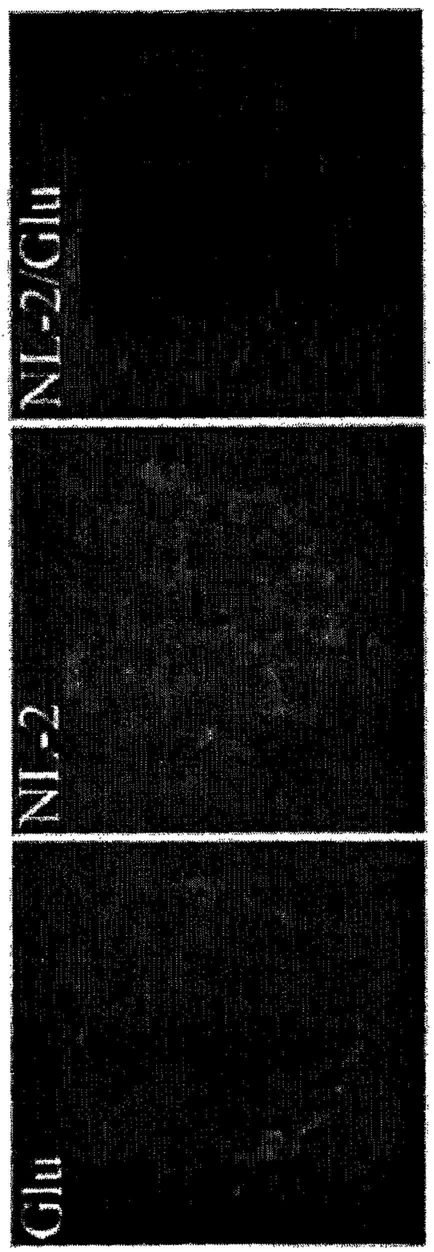
FIG. 1A. Depiction of neuroligin 2 and neurexin 1 staining to be, β-cell specific.
Figure 1A:
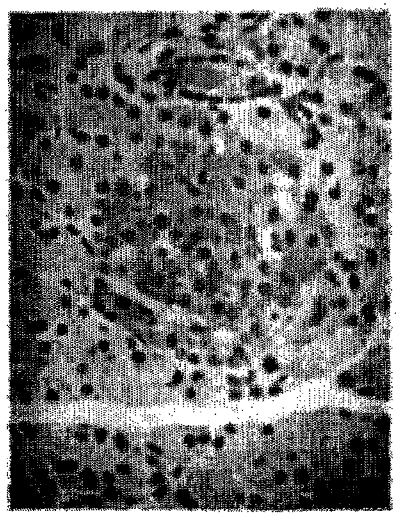
Figure 2:
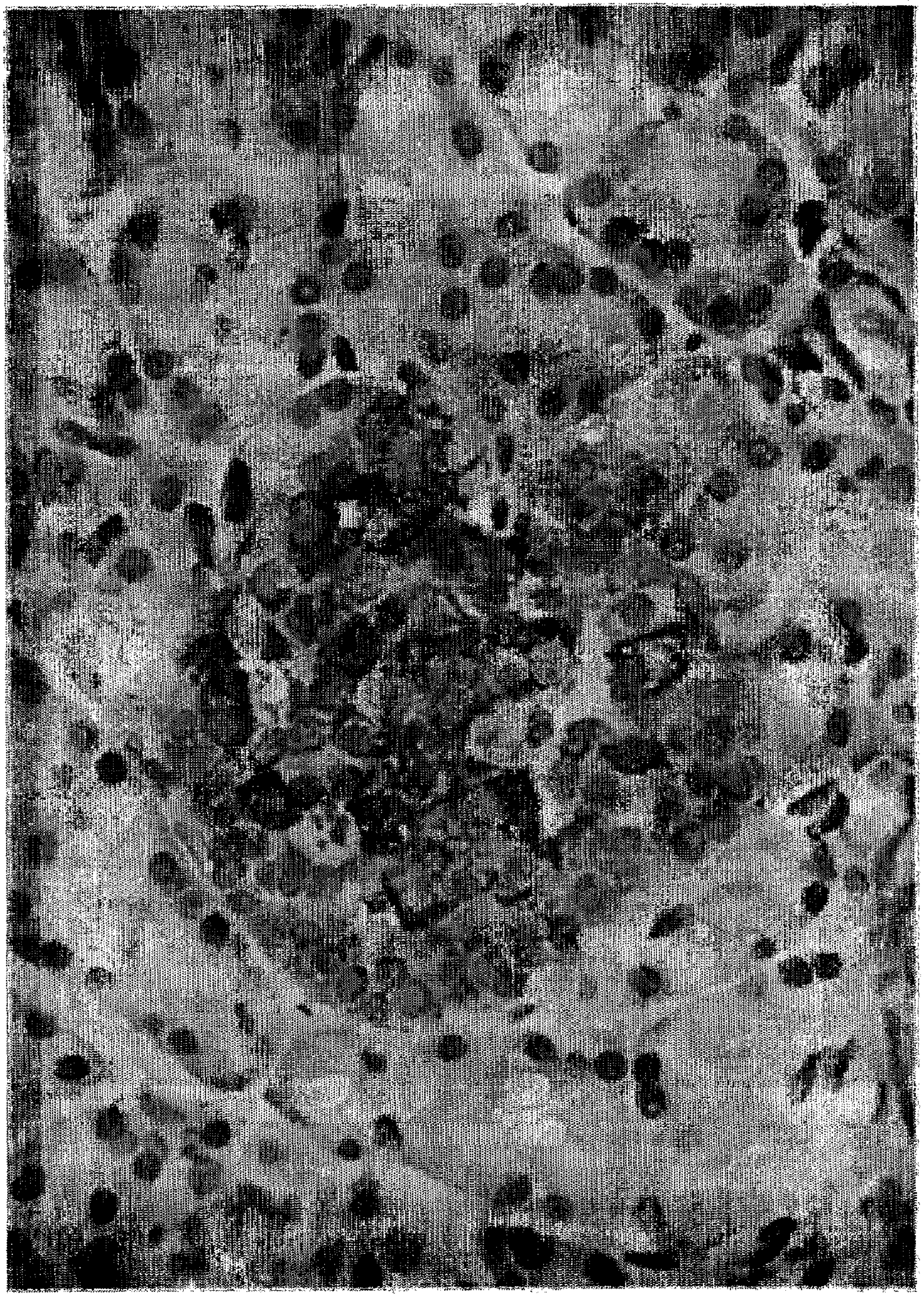
FIG. 2. Depiction of SynCam specificity islet specificity.
Figure 3:
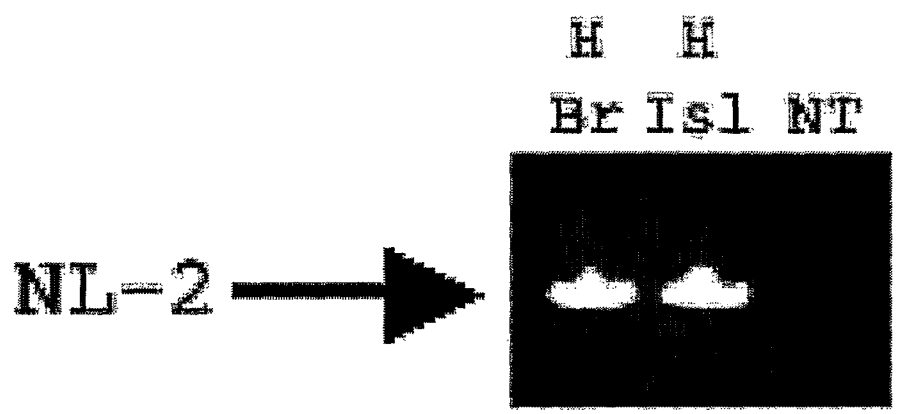
FIG. 3. NL-2 (neuroligin 2) is expressed in Beta cells. PCR data (human brain and islet cDNA, NT=negative control). INS-1 is a commonly used cell line used to study the biology of the pancreatic islet β cells.
Figure 4:
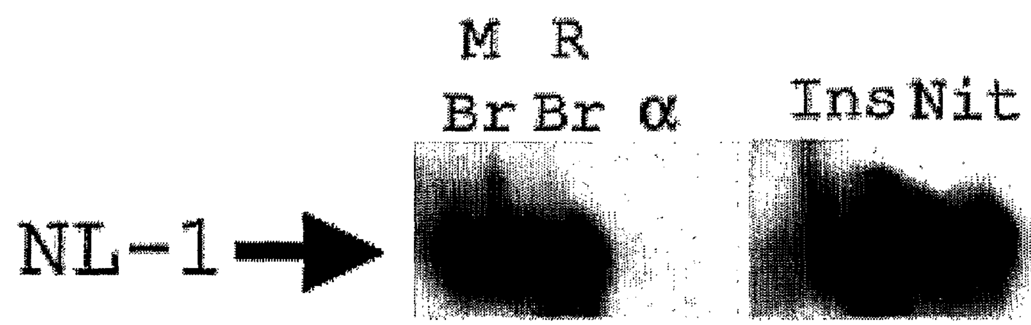
FIG. 4. Western blot: neuroligin 1 in mouse brain, rat brain (on left) and two insulin-producing Beta cell lines (NIT and INS-1; on right) but not the alpha cell line alpha-TC6 (3rd lane). Antibody was monoclonal antibody (4C12) specific for neuroligin 1.
Figure 5:
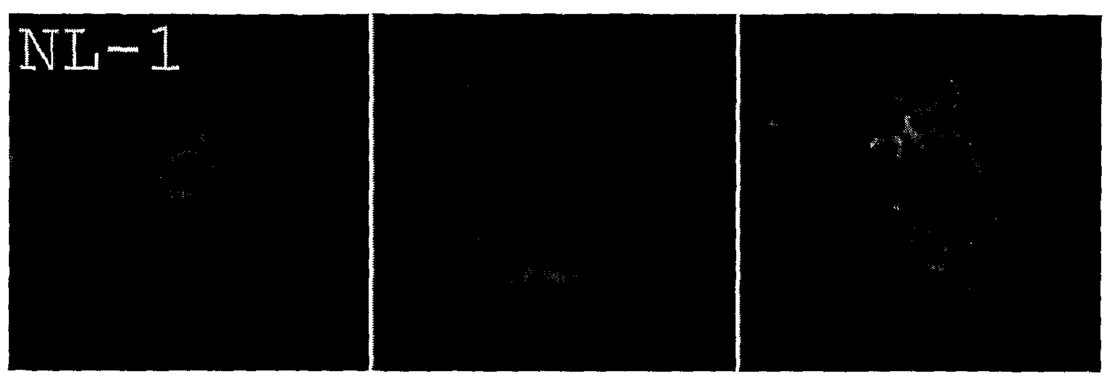
FIG. 5. NL-1 immunostaining. Neuroligin 1 is in the Beta cell line INS-1.
Figure 6:
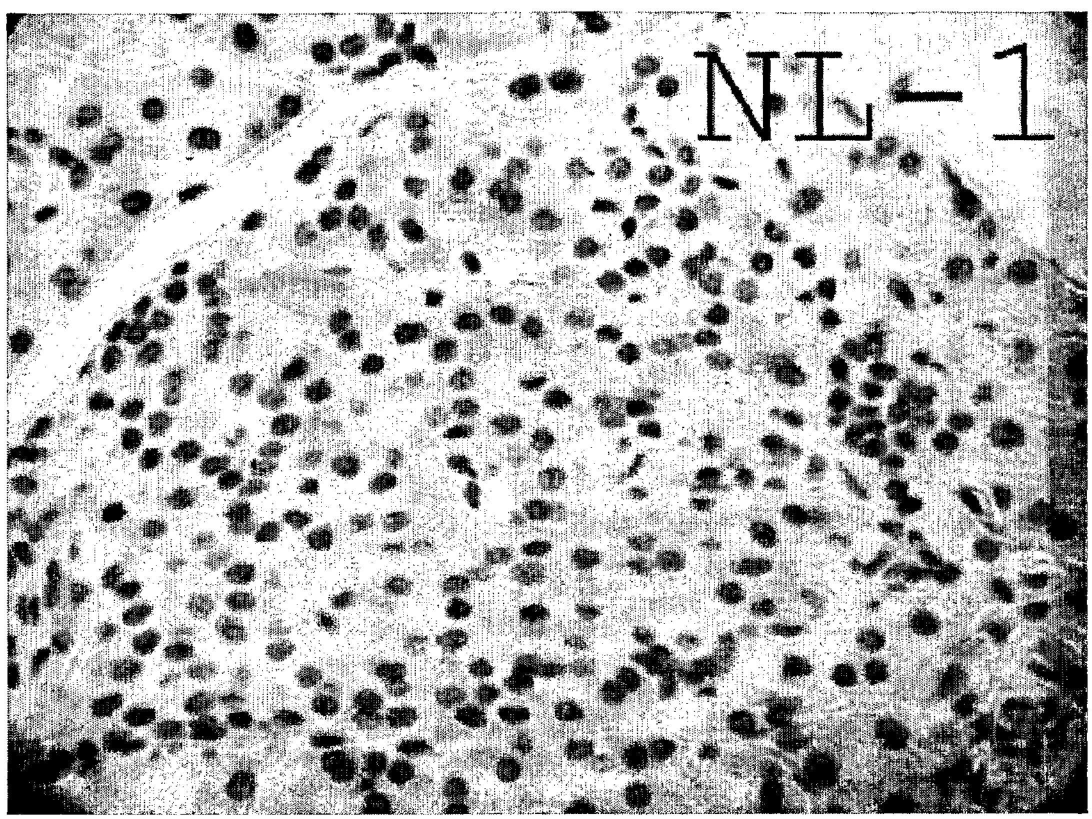
FIG. 6. An antibody to NL-1 stains islets in rat pancreas sections.
Figure 7:
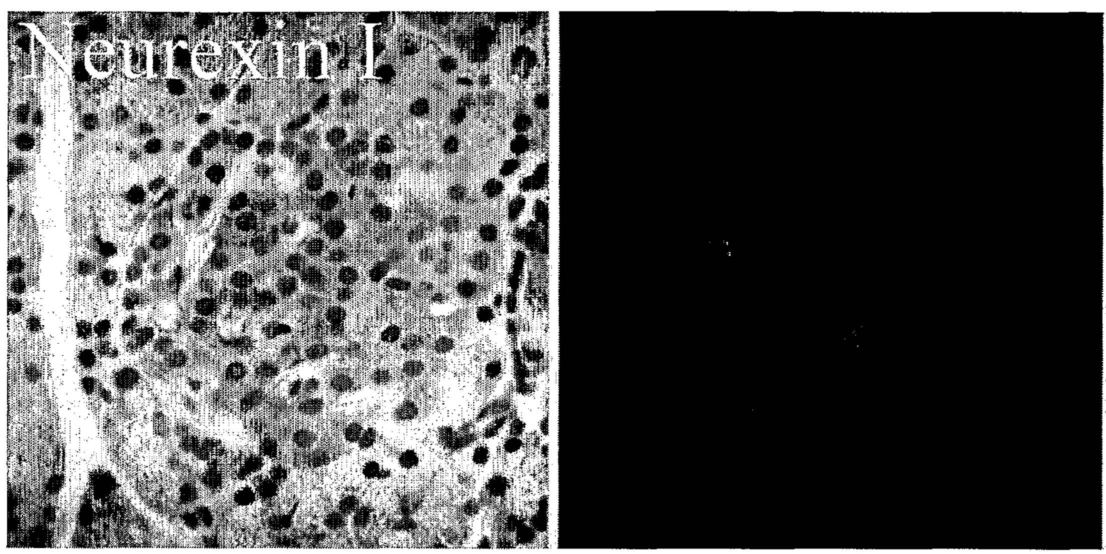
FIG. 7. Immunostaining for neurexin 1. Neurexin 1 is in pancreatic islets (on left; pancreas staining is islet-specific) and in the insulin-producing INS-1 Beta cell line.
Figure 8:
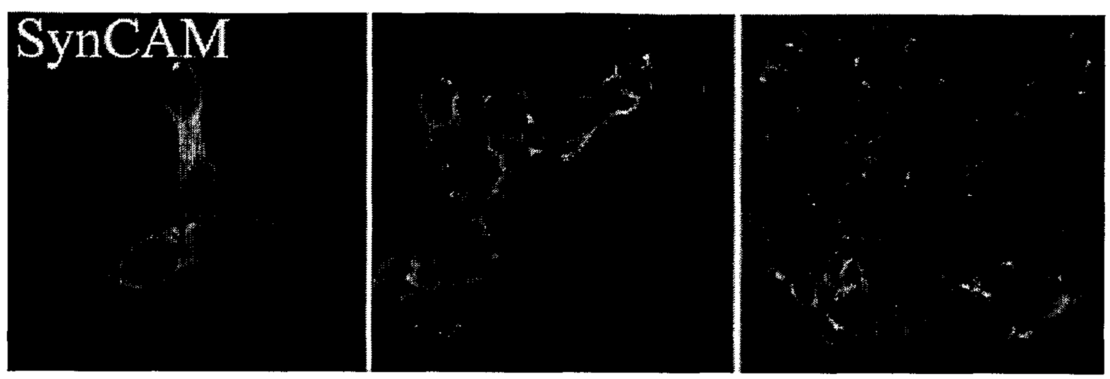
FIG. 8. Immunostaining for SynCam. SynCam is present on the surface of the islet Beta cell line INS-1.
Figure 9:
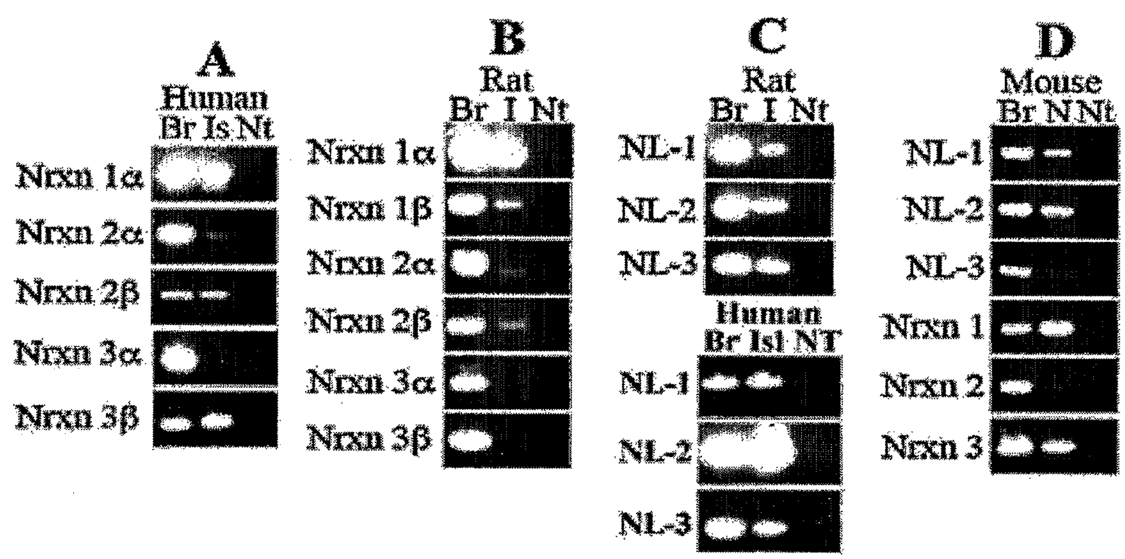
FIG. 9. Polymerase chain reaction using gene-specific primers shows that the neuroligins (NLs) and neurexins (Nrxn) are expressed in human islets (Is) and the rat-derived islet Beta cell line INS-1 (I) and the mouse-derived islet Beta cell line Nit-1 (N). As expected, the genes are also expressed in brain (Br).
Figure 10:
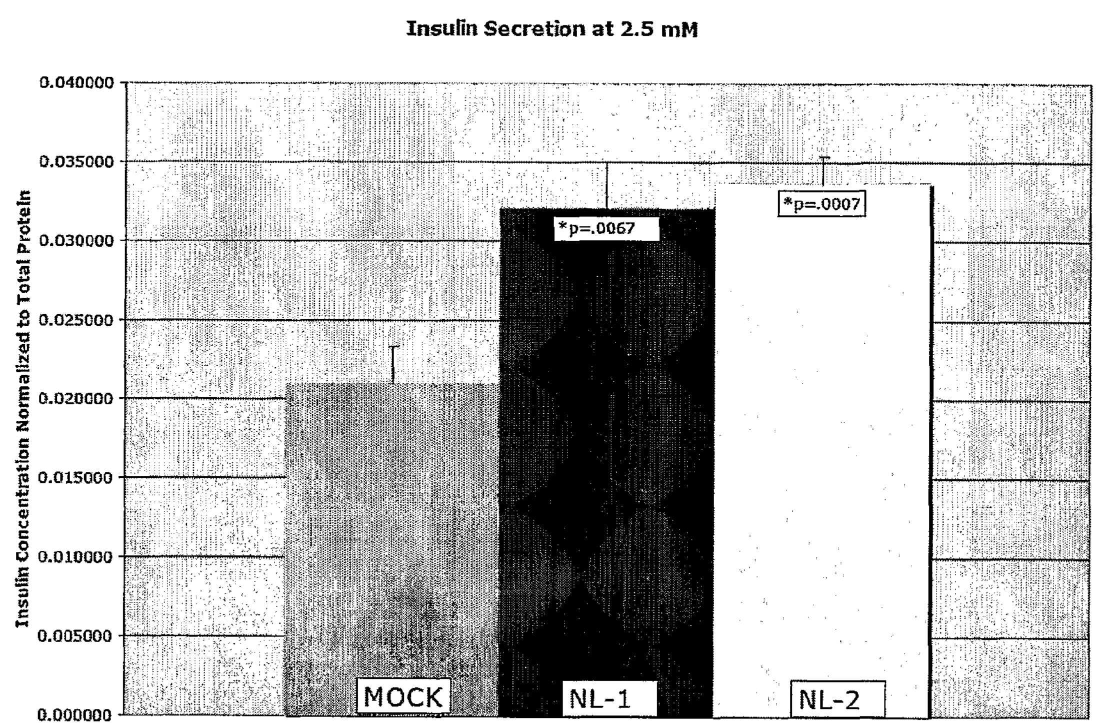
FIG. 10. Neuroligins 1 and 2 are involved in insulin secretion. Increased insulin secretion is evident after overexpression (by gene transfection) of NL-1 and NL-2 in the Beta cell line INS-1. "Mock" is a control with no neuroligin overexpression.
Figure 11:
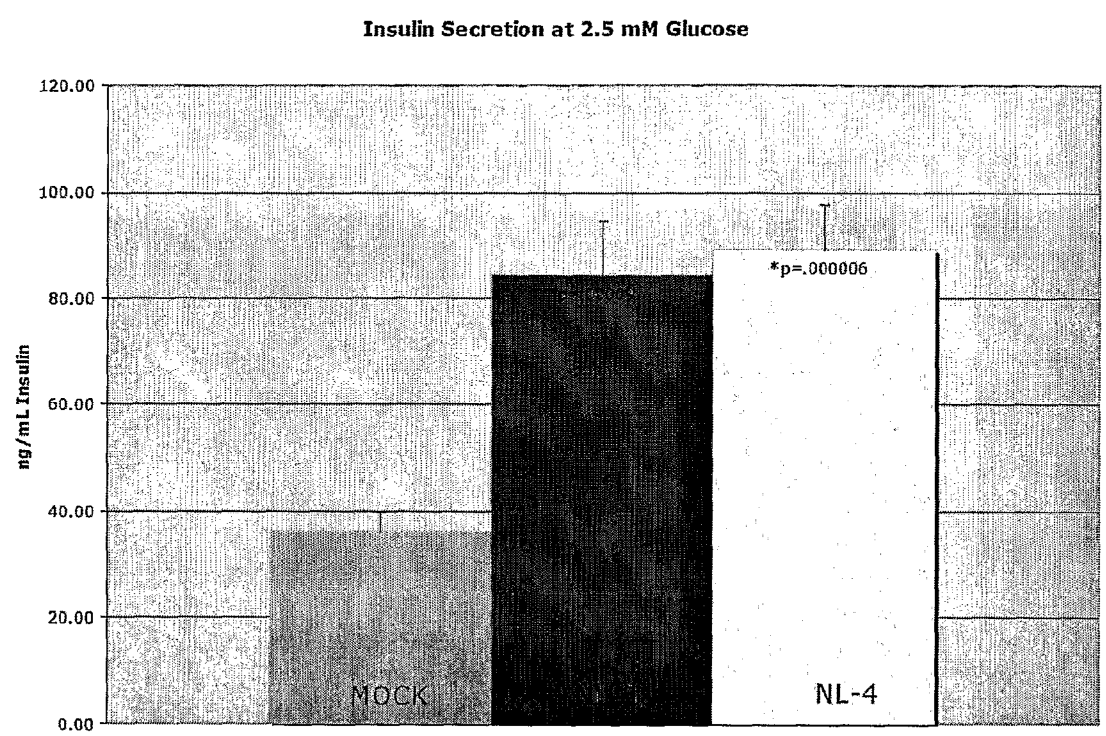
FIG. 11. Neuroligins 3 and 4 are involved in insulin secretion. Increased insulin secretion is evident after overexpression (by gene transfection) of NL-1 and NL-2 in the Beta cell line INS-1. "Mock" is a control with no neuroligin overexpression.
Figure 12:
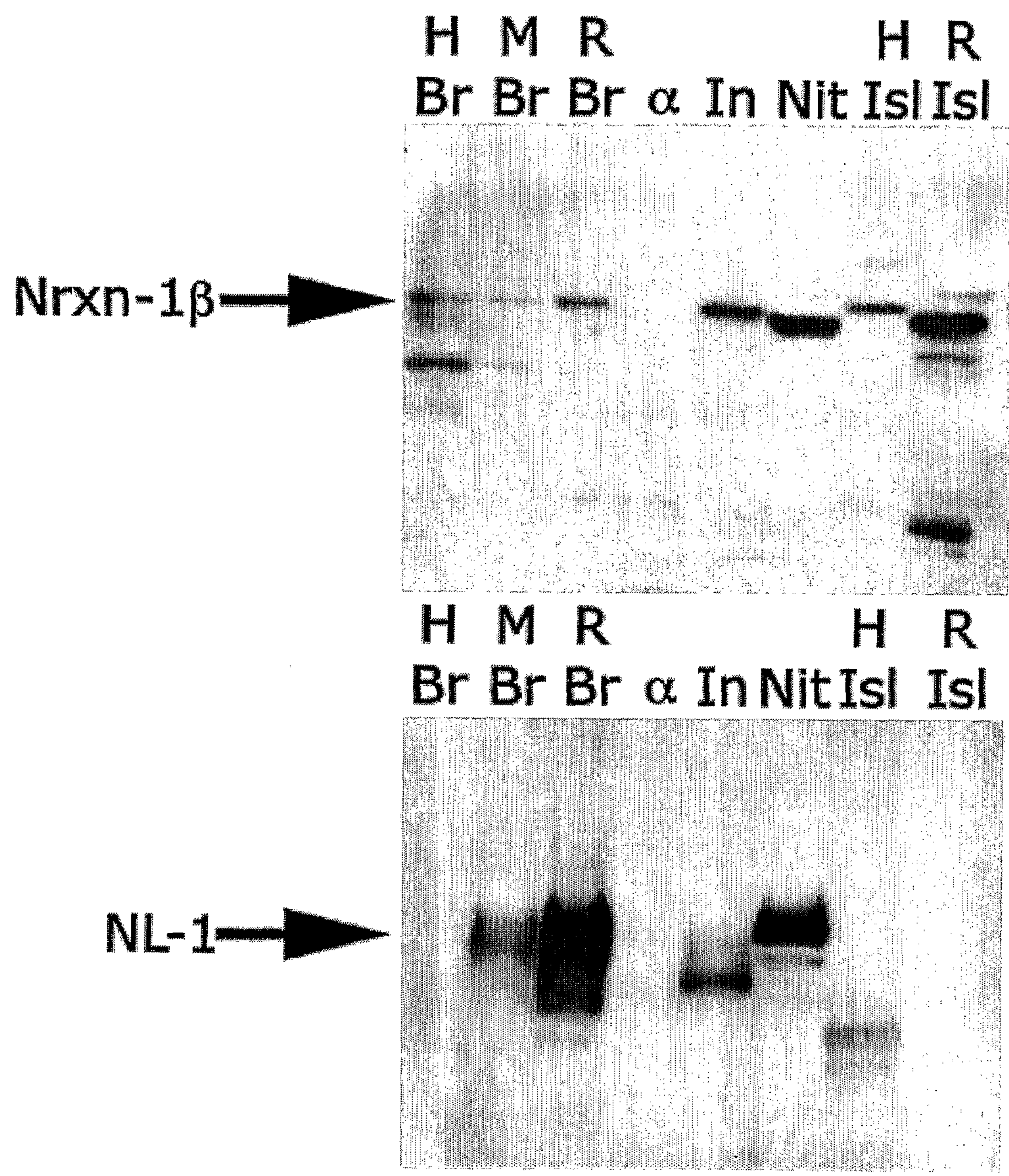
FIG. 12. Expression of Neurexin 1 and Neuroligin 1 Protein in Islets and Islet cell lines. To determine whether neurexin and neuroligin proteins are expressed in islets, western blot analysis was performed using a goat polyclonal antibody to neurexin 1 and a mouse monoclonal antibody to neuroligin 1 (4C12). Neurexin 1b was detected in the b-cell lines Ins-1 and NIT, as well as in both human and rat islet extracts. Neuroligin 1 was only detected in INS-1 and NIT cells. In all experiments, protein extract from rat, mouse and human brains were used as positive controls. Since Neuroligin 1 was not detected in Human or Rat Islets, we suspected that the method used to isolate islets affected detection of it. It is notoriously difficult to detect cell surface proteins via WB analysis due to digestive enzymes produced in the pancreas. To determine of NL-1 was sensitive to some of these enzymes, we treated the beta-cell line NIT with trypsin. Here, we show that neuroligin is sensitive to trypsin. We also demonstrated that neurexin is not. In doing this experiment, we also confirmed that neurexin was expressed on the cell surface of NIT cells.
Figure 13:
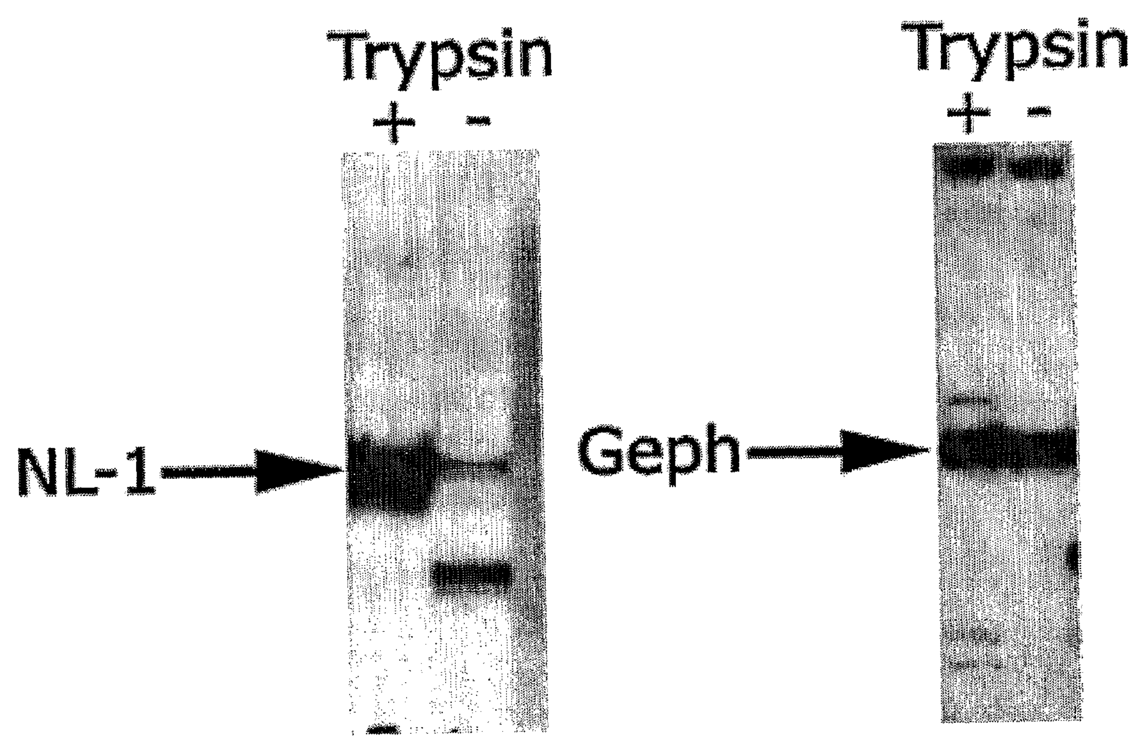
FIG. 13. Cell Surface Expression of Neuroligin 1 in the NIT b-cell line. To determine if Neuroligin 1 is expressed on the cell surface, NIT cells were plated in flasks, cultured for 48 hours and either treated with or without trypsin. Protein was then extracted and western blot analysis was performed with equal amounts of protein using monoclonal neuroligin 1 antibody. Neuroligin 1 was decreased in cells treated with trypsin, suggesting that it is expressed on the cell surface of NIT cells. As a negative control, the same experiment was performed probing for the intracellular protein gephryin. As expected, gephyrin was not affected by treatment of cells with trypsin. (+, trypsin; −, not treated with trypsin).
Figure 14:
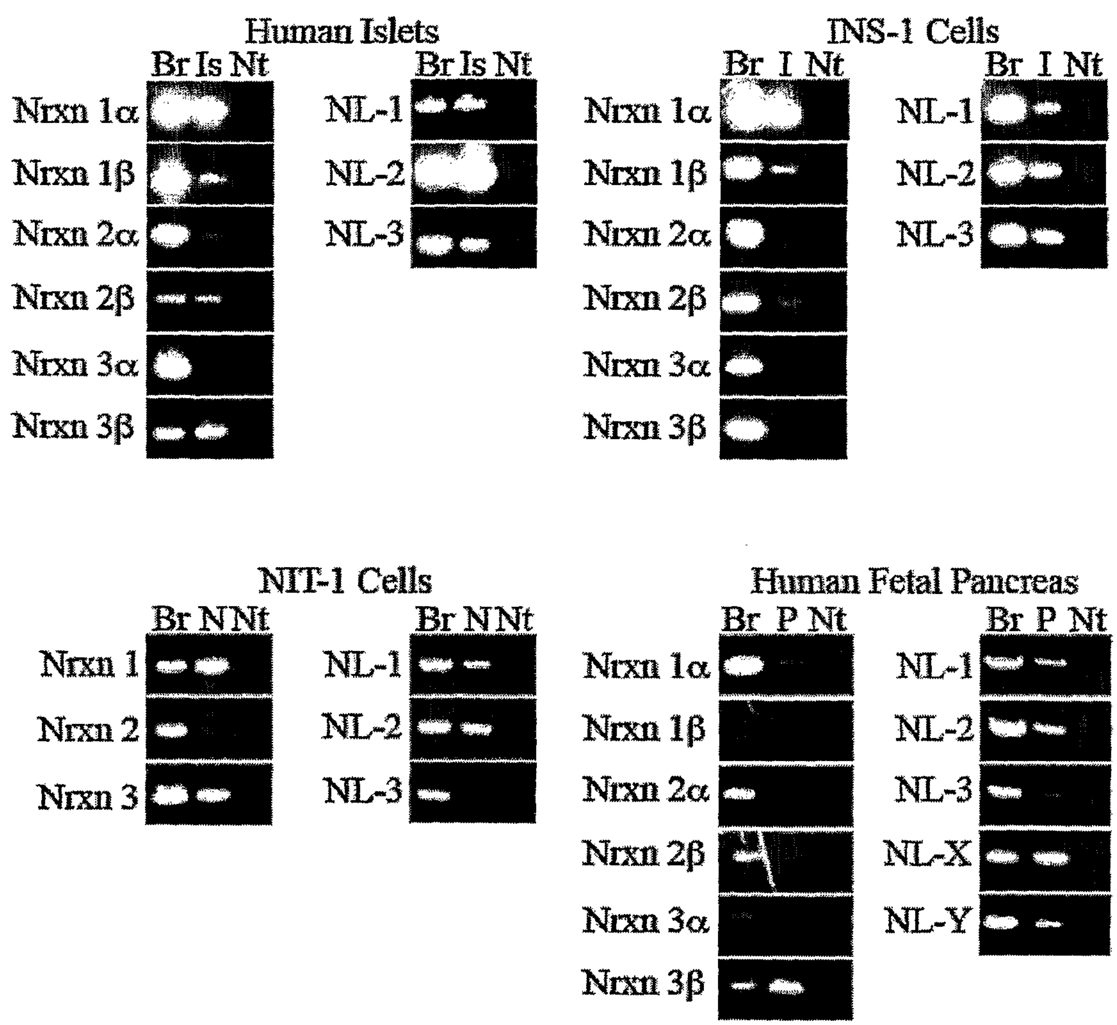
FIG. 14. Expression of neurexin and neuroligin RNA in Human pancreatic Islets and Rat and Mouse b-cell lines. To determine whether neurexin and neuroligin messages are expressed in islets, RT-PCR analysis was performed on (A) human pancreatic islets, (B) INS-1 cells, (C) NIT cells and (D) human fetal pancreas using gene specific primers to all neurexin (Nrxn) and neuroligin (NL) family members. In all experiments, brain RNA from the appropriate species was used as a positive control. (Br, brain; Is; human islets; Nt, no template; I, INS-1 cells; N, NIT cells; P, human fetal pancreas; Nrxn, neurexin; NL, neuroligin).
Figure 15:
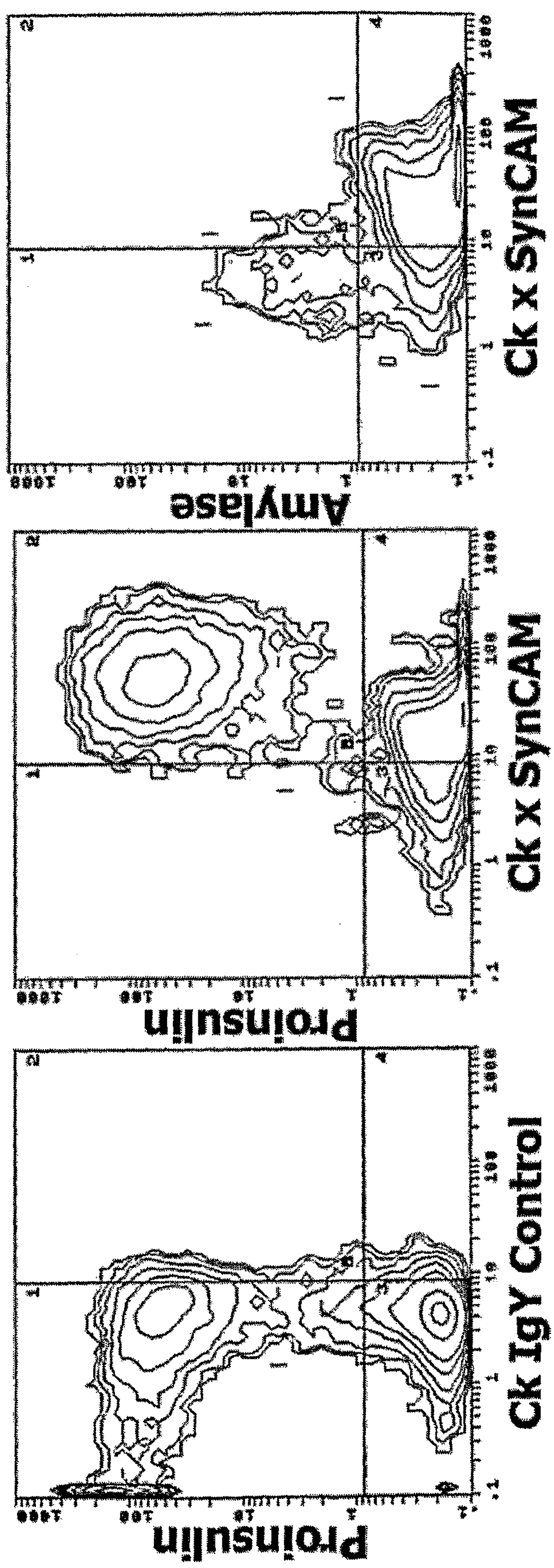
FIG. 15. Data from fluorescent activated cell sorting (FACS) obtained using human pancreatic cells. Cells were labeled with antibodies to proinsulin and to the extracellular domain of SynCam (an antibody of chicken egg origin). Left panel: control chicken antibody (IgY) does not enable sorting for proinsulin-positive cells, Center panel: A large fraction of the cells with high labelling by the extracellular SynCam antibody (towards the right) also exhibit high proinsulin antibody labelling (towards the top). Right panel: Cell with high amylase expression (in other words, pancreatic acinar [non-islet] cells) did not label with SynCam (the acinar cells were towards the left). Conclusion: Sorting pancreatic cells with SynCam enables purification of the insulin-producing islet beta cells from the pancreatic acinar cells (which comprise most of the 98% of the pancreas that is non-islet). Sorting with SynCam yields a population of cells greatly enriched for beta cells.

Unless otherwise defined, all technical terms used herein have the same meaning as commonly understood by one of ordinary skill in the art to which this invention belongs. Commonly understood definitions of molecular biology terms can be found in Rieger et al., GLOSSARY OF GENETICS: CLASSICAL AND MOLECULAR, 5th edition, Springer-Verlag; New York, 1991; and Lewin, GENES V, Oxford University Press; New York, 1994. To facilitate the understanding of the invention, a number of terms and abbreviations as used herein are defined below as follows:

Bind(s) or Interacts With: As used herein, the terms "bind," or "interacts with" refers to an activity wherein one molecule recognizes and adheres to a particular second molecule in a sample, but does not substantially recognize or adhere to other structurally-unrelated molecules in the sample. Generally, a first molecule that "specifically binds" to a second molecule has a binding affinity greater than about $10^5$ to $10^6$ moles/liter for that second molecule.

Nucleic Acid or Nucleic Acid Molecule or polynucleotide: As used herein, the terms "nucleic acid" or "nucleic acid molecule" refer to a chain of two or more nucleotides such as RNA (ribonucleic acid) and DNA (deoxyribonucleic acid).

Pharmaceutically Acceptable: As used herein, the term "pharmaceutically acceptable" means approved by a regulatory agency or authority, either national (e.g. the FDA), supranational (e.g. the EMEA), or other regulatory agency, governmental entity, ethics board, or committee involved in the granting of Regulatory Approval, or a state government, or listed in the U.S. Pharmacopeia or other generally recognized pharmacopeia for use in animals and, more particularly, in humans.

Pharmaceutically Acceptable Carrier: As used herein, the term "pharmaceutically acceptable carrier" refers to a diluent, adjuvant, excipient, or vehicle with which an agent is administered. Such carriers can be sterile liquids, such as water and oils, including those of petroleum, animal, vegetable, or synthetic origin, such as peanut oil, soybean oil, mineral oil, sesame oil, tocopherols and the like, polyethylene glycols, glycerine, propylene glycol, or other synthetic solvents. Water is a preferred carrier when an agent is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or and compound found in the *Handbook of Pharmaceutical Excipients* (4th edition, Pharmaceutical Press) and the like. An agent, if desired, can also contain minor amount of wetting or emulsifying agents, or pH buffering agents such as acetates, citrates, or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier.

Protein or Polypeptide: As used herein, the terms "protein" or "polypeptide" mean any peptide-linked chain of amino acids, regardless of length or post-translational modification, e.g. glycosylation or phosphorylation.

Therapeutically Effective Amount: As used herein, the term "therapeutically effective amount" refers to those amounts that, when administered to a particular subject in view of the nature and severity of that subject's disease or condition, will have a desired therapeutic effect, e.g. an amount which will cure, prevent, inhibit, or at least partially arrest or partially prevent a target disease or condition.

Methods for Treating and Detecting Beta-Cell Disease

The present invention relates to a method for imaging, treating, separating and identifying islet β-cells using β-cell specific molecules present on the surface thereof. In one aspect of the present invention, a class of molecules known collectively as SAMs are utilized. SAMs have previously been thought to be expressed only in neurons. It has been surprisingly discovered, however, that such molecules are also expressed in pancreatic islet β-cells. In another aspect of the present invention, neuropilin 1, a member of the immunological synapse (but not a synaptic adhesion molecule) is used in the present method.

The SAM and neuropilin sequences of the invention include: Neuroligin 1 (NCBI Accession No: NM_014932, SEQ ID NO: 1); Neuroligin 2 (NCBI Accession Nos: NM_020795 and AF376802, SEQ ID NOs: 2 and 3); Neuroligin 3 (NCBI Accession No: NM_018977, SEQ ID NO: 4); Neuroligin 4Y (NCBI Accession No: AF376804, SEQ ID NO: 5); Neuroligin 4X (NCBI Accession No: AF376803, SEQ ID NO: 6); Neurexin 1 Alpha (NCBI Accession No: NM_004801, SEQ ID NO: 7); Neurexin 1 Beta (NCBI Accession No: NM_138735, SEQ ID NO: 8); Neurexin 2 alpha (NCBI Accession Nos: NM_015080, NM_138732, SEQ ID NOs: 9 and 10); Neurexin 2 beta (NCBI Accession No: NM_138734, SEQ ID NO: 11); Neurexin 3 alpha (NCBI Accession No: NM_004796, SEQ ID NO: 12); Neurexin 3 beta (NCBI Accession No: NM_138970, SEQ ID NO: 13); Syncam (NCBI Accession No: NM_014333, SEQ ID NO: 14); THY-1 (NCBI Accession No: BC065559, SEQ ID NO: 15); and Neuropilin 1 (NCBI Accession Nos: NM_003873, NM_001024628 NM_001024629, SEQ ID NOs: 16, 17, and 18). The invention also includes SAM and neuropilin proteins including SAM and neuropilin variants, fragments, analogs and the like as described below.

Previously published articles in the art claim that neuropilin 1 is not expressed in the pancreas. It has been surprisingly found that this molecule is, in fact, expressed in the β-cells of the pancreas. The presence of SAMs and/or neuropilin 1 on β-cells may be utilized to assess β-cell mass, location, presence, and depletion as they relate to certain diseases such as pancreatic cancer and diabetes mellitus.

Because the blood brain barrier functions to prevent the transmission of macromolecules circulating in the body from entering the nervous tissue—an immune privileged site—the present method results specifically in the imaging, identification, treatment, and separation of SAMs on pancreatic islet β-cells. Thus, SAMs are a preferred target for imaging and treating pancreatic diseases.

The current invention provides a method for detecting both in vitro and in vivo, and imaging pancreatic islets, β-cells in vitro and in vivo by administering to a mammal an agent capable of selectively binding to SAMs and/or neuropilin 1 molecules present on the surface of pancreatic islet β-cells. Experiments using the polymerase chain reaction have revealed that the SAMs expressed in islet β-cells include neuroligin 1, neuroligin 2, neuroligin 3, neuroligin 4X, neuroligin 4Y, neurexin 1α, neurexin 2α, neurexin 3α, neurexin 1β, neurexin 2β, neurexin 3β, SynCam, Thy-1, and neuronal pentraxin. In accordance with a further aspect of the invention the agent is selected from a group consisting of an antibody, antibody fragment, variable region of an antibody, protein, polypeptide, nucleic acids, probes, oligonucleotides, and ribozymes. The various aspects of the agent are described more fully below.

Antibodies

Antibodies that specifically recognize and bind to SAM and/or neuropilin 1 protein are useful in the invention. For example, such antibodies can be used for detection and modulation of SAM function. Antibodies within the scope of the invention include, for example, polyclonal antibodies, monoclonal antibodies, and antibody fragments. Engineering, production, purification, fragmentation, and use of various types of antibodies is well known in the art. See generally, Carter (2006) Nat Rev Immunol. 6(5), 343-357; Teillaud (2005) Expert Opin Biol Ther. 5 (Supp. 1) S15-27; Subramanian, ed. (2004) Antibodies: Volume 1: Production and Purification, Springer, ISBN 0306482452; Lo, ed. (2003) Antibody Engineering Methods and Protocols, Humana Press, ISBN 1588290921; Ausubel et al., ed. (2002) Short Protocols in Molecular Biology 5th Ed., Current Protocols, ISBN 0471250929; Brent et al., ed. (2003) Current Protocols in Molecular Biology, John Wiley & Sons Inc, ISBN 047150338X; Coligan (2005) Short Protocols in Immunology, John Wiley & Sons, ISBN 0471715786.

Polyclonal Antibodies

Polyclonal antibodies are heterogeneous populations of antibody molecules that are obtained from immunized animals, usually from sera. Polyclonal antibodies may be readily generated by one of ordinary skill in the art from a variety of warm-blooded animals, as well known in the art and described in the numerous references listed above. Further, polyclonal antibodies can be obtained from a variety of commercial sources.

Monoclonal Antibodies

Monoclonal antibodies are homogeneous populations of antibodies to a particular antigen. In contrast to polyclonal antibodies that may be specific for several epitopes of an antigen, monoclonal antibodies are usually specific for a single epitope. Generally, monoclonal antibodies are produced by removing B-cells from the spleen of an antigen-challenged animal (wherein the antigen includes the proteins described herein) and then fusing with myeloma tumor cells that can grow indefinitely in culture. The fused hybrid cells, or hybridomas, multiply rapidly and indefinitely and can produce large amounts of antibodies. The hybridomas can be sufficiently diluted and grown so as to obtain a number of different colonies, each producing only one type of antibody. The antibodies from the different colonies can then be tested for their ability to bind to the antigen, followed by selection of the most effective.

In particular, monoclonal antibodies can be obtained by any technique that provides for the production of antibody molecules by continuous cell lines in culture such as those described in references listed above. Further, monoclonal antibodies can be obtained from a variety of commercial sources.

Such antibodies can be of any immunoglobulin class including IgG, IgM, IgE, IgA, IgD and any subclass thereof. Preferably, the antibody is of the IgG immunoglobulin class. A hybridoma producing a mAb of the invention may be cultivated in vitro or in vivo. The ability to produce high titers of mAbs in vivo makes this a particularly useful method of production. MAbs generally have a longer terminal half life than many antibody fragments, translating into greater uptake, that can be desirable for therapeutic applications.

MAbs can be selected on the basis of their (a) specificity, (b) high binding affinity, (c) isotype, and (d) stability. MAbs can be screened or tested for specificity using any of a variety of standard techniques, including Western Blotting (Koren, E. et al., Biochim. Biophys. Acta 876:91-100 (1986)) and enzyme-linked immunosorbent assay (ELISA) (Koren et al., Biochim. Biophys. Acta 876:91-100 (1986)).

These monoclonal antibodies will usually bind with at least a KD of about 1 mM, more usually at least about 300 μM, typically at least about 10 μM, more typically at least about 30 μM, preferably at least about 10 μM, and more preferably at least about 3 μM or better.

Antibody Fragments

It may be desirable to produce and use functional antibody fragments, for example Fab, F(ab')2, F(ab')2, F(ab')3, Fc, single chain Fv (scFv), scFV-Fc, (scFv)2, dsFv, Vh, Vl, Minibody, Diabody, Triabody, Tetrabody. Generally, these alternative antibody formats can span a molecular-weight range of 12-150 kDa; a valency (n) range from monomeric (n=1), dimeric (n=2), trimeric (n=3), tetrameric, or even higher; and antigen-binding specificities from 1 to more than three antigens or epitopes on the same antigen.

These fragments will generally include hypervariable regions containing stretches of amino acid sequences known as complementarity determining regions, which are responsible for the antibody's specificity for one particular site on an antigen molecule. A building block that can be used to create various antibody formats is the single-chain variable (V)-domain antibody fragment (scFv), which comprises V domains from the heavy and light chain (VH and VL domain) joined by a peptide linker of up to about 15 amino-acid residues. Preferably, the scFV antibody fragment is composed of the VL-domain-peptide-linker-VH-domain topology or the VH-domain-peptide-linker-VL-domain topology.

Techniques for designing, producing, purifying, screening, antibody fragments are well known in the art as described in the numerous references cited above. For example, filamentous phage display expressing large combinatorial libraries of human VH and VL make it possible to select for specific fragments (see e.g., Hoogenboom (2002) Methods Mol. Biol. 178, 1-37, providing a review of antibody phage display technology). Phage-display selection technology can also be utilized to, for example, optimize binding affinity; select for specific binding properties, such as species cross-reactivity; or obtain large (e.g., over 1,000) collections of specific antibodies to identify combinatorial properties or very high potency. Antibody fragments produced via phage display can be reformatted through high-throughput methods into various other forms of antibodies, such as IgG, as known in the art. As another example, generation and isolation of high-affinity antibodies can be based upon the use of hypermutating B cell lines and on a selection process initiated at a very low affinity threshold (see e.g., Cumber et al. (2002) Nat. Biotechnol. 20, 1129-1134). As a further example, antibody fragments can be produced by ribosome display library screening, involving selection, recovery, amplification, and expression of antibody fragment mRNAs, optionally followed by reformatting of VH and VL (see e.g., Hanes et al. (2000) Nat. Biotechnol. 18, 1287-1292). As yet another example, using multiplex yeast library screening involving C-terminus fusion to the mating adhesion receptor of *Saccharomyces cerevisiae*, antibody fragments from a randomly mutated library can be selected and isolated (see e.g., Feldhaus et al. (2003) Nat. Biotechnol. 21, 163-170). 1

Also, the antibody fragments described herein can be reformatted through high-throughput methods to, for example, IgG molecules. See e.g., Carter et al. (2006) Nat Rev Immunol. 6(5), 343-357, 347. Antibody fragments can be desirable to avoid Fc-dependent effector functions. And, after PEGylation, antibody fragments can show a broad range of pharmacokinetic properties. Because of more efficient tumor penetration and faster clearance, antibody fragments can be desirable for imaging applications. And a monovalent antibody fragment can be more desirable than a bivalent form, such as IgG, for use as a receptor antagonist that can block ligand binding to a receptor without crosslinking and potentially activate the receptor.

Antibody-Based Fusion Molecules

Antibody-based fusion molecules exhibiting at least two different modules with bifunctional activities can be produced from molecular engineering techniques known in the art. Engineered fusion molecules contain a flexible linker between the two modules. The linker can be, for example, derived from the hinge region of an IgG isotope, a small stretch of hydrophobic amino acids such as the (Gly4Ser)3 motif, or a few amino acids corresponding to a DNA enzyme restriction site.

Generally, two types of antibody-based fusion molecules can be engineered. The first type of antibody-based fusion molecules are molecules that retain antibody specificity fused to enzymes, toxins, growth factors, chemokines, cytokines, etc. The target recognition module can be antibody fragments or whole antibodies. For example, the target module can be fused to a toxin module such as *Pseudomonas* toxin, ricin, diphtheria toxin, or other toxins known to the art. As another example, the target module can be fused to an enzyme, preferably an enzyme used to generate a toxic product from a prodrug. This strategy, termed ADPET (antibody-directed enzyme prodrug therapy) is based on the pretargeting of, for example, tumor cells by the fusion molecule, which is injected systemically and allowed to clear from normal tissue. Glycosolation can improve control and clearance from non-target tissue sites. A nontoxic prodrug is then infused and transformed by the enzyme to a bioactive agent at the target site. As another example, fusion reagents for various ELISAs can be generated by fusing an antibody with alkaline phosphatase.

An alternative to bifunctional molecules include bispecific antibodies (BsAbs) that crosslink effector and target cells (see e.g., Weiner and Adams (2000) Oncogene 19, 6144-6151). BsAbs facilitate pretargetting strategies where a BsAb is first infused, followed by injection of molecules such as radiolabelled haptens, drugs, or cytokines, which allows concentrating effector molecules in the vicinity of the cells to which the BsAb is bound (see e.g., Chang et al. (2002) Mol. Cancer. Ther. 1, 553-563).

The second type of antibody-based fusion molecules act as competitors of surface molecules for ligand binding or as soluble decoy receptors for capturing soluble ligands (see e.g., Teillaud (2005) Expert Opin Biol Ther. 5(Suppl 1) S15-27). Generally, these fusion molecules contain an Fc region (e.g., Fc derived from IgG1 or IgG4) and are secreted under dimeric forms by mammalian cells, such as CHO or NS1 cells, due to formation of a disulfide bridge between each of the expressed single-strand fusion protein via the three cysteines present in the Fc region. This dimeric recombinant form can bind the target molecule with an avidity higher than the monovalent equivalent. Furthermore, the Fc region increases the serum-half life and tissue diffusion, facilitates clearance of the immune complexes, and/or stabilizes interactions of the fusion molecule with its target antigen by interacting also with FcγRs expressed by immune cells.

Engineering Antibodies for Reduced Immunogenicity

Chimeric, humanized, and fully human MAbs can effectively overcome potential limitations on the use of antibodies derived from non-human sources, this providing decreased immunogenicity with optimized effector functions. Such agents can be produced through protein engineering (e.g., complementarity-determining region grafting), through library technologies (e.g., phage, yeast, or ribosome display), or by MAb generation in transgenic mice.

Generally, chimeric and humanized antibodies will contain an Fc region derived from human IgG1, because this subclass exhibits characteristics (FcγRs binding, serum half-life) and functional properties (ADCC, phagocytosis, endocytosis, complement activation) adequate for immune intervention. To avoid triggering of effector functions (i.e., complement activation and functional properties triggered by FcγRs binding) and to decrease nonspecific binding to normal tissues, it is preferable to use the Fc region of human IgG2 or IgG4. Antibody fragments for use in developing chimeric and humanized antibodies can be produced by any of the methods discussed above, including but not limited to, phage display library screening, hypermutating B cell lines, ribosome display library screening, and yeast display library screening.

Chimeric antibodies can be obtained by joining the variable domains of, for example, a mouse monoclonal antibody to the constant domains of human heavy and light chains. Such an approach can address the sometimes high immunogenicity of foreign proteins in humans, the weak interactions and inefficient effector functions that non-human antibodies can have with human complement and FcγRs, and the reduced terminal half-life of non-human antibodies that can occur in human system. Expression vectors can be built to contain appropriate cloning sites allowing the in-frame cloning of the rodent leader heavy-chain variable domain (VH) cDNA and leader-light chain variable domain (VL) cDNA, 5' of DNA sequences coding human IgG Fc region and Cκ domain, respectively. Thus, reshaped VH and VL cDNA together with leader sequences can be cloned into expression vectors that contain human constant regions.

Humanized antibodies can be obtained by grafting complementarity determining regions (CDRs) derived from murine antibodies with desired specificity onto human VH and VL frameworks (FRs) (see e.g., Teillaud (2005) Expert Opin. Biol. Ther. 5(1), S15-S27). Further, transfer of one or more framework-region residues from the parent mouse antibody can result in the generation of humanized antibodies with a high binding affinity for antigen. Antibody humanization generally requires analysis of the primary amino acid sequences of the mouse variable domains to identify the residues involved in the antigen-binding site formation. Alternatively, in variable domain resurfacing, humanization of murine mAbs can be based on systematic analysis of known antibody structures to determine the solvent accessibility distributions of amino acid residues in murine and human variable regions (see e.g., Roguska et al. (1994) Proc. Natl. Acad. Ci. USA 91, 969-973; Delagrave et al. (1999) Protein Eng. 12, 357-362). The identified murine surface residues pattern can be converted to a human pattern with only a few amino acid changes.

It can often desirable to obtain species-cross reactive antibodies, allowing the biological function of the antibodies to be evaluated and/or utilized in animal models of disease. Selection of humanized antibodies with species cross-reactivity can be accomplished with, for example, phage-display libraries.

Fully human antibodies can be derived by several means known to the art. For example, phage display As another example, gene inactivation and insertion of large human DNA fragments from yeast artificial chromosome or human chromosome fragments in mouse germline can produce transgenic mice capable of producing fully human antibodies following immunization (see e.g., Tomizuka et al. (2000) Proc. Nat. Acad. Sci. USA 97, 722-727). Such mice can generate a repertoire of human sequence immunoglobulins and, additionally, their spleen cells can be fused to mouse myeloma cells for generating hybridomas secreting human IgG antigen-specific antibodies exhibiting high affinity. Alternatively, transgenic mice such as double trans-chromosomic/double knockout mice can mount an antigen-specific human antibody response following immunization, and human-specific mAbs can be generated (see e.g., Tomizuka et al. (2000) Proc. Nat. Acad. Sci. USA 97, 722-727). Other examples for generation of human antibodies include phage-, ribosome-, mRNA- and yeast-display libraries, as well as human hybridomas from patients and antibody-cDNA cloning from single lymphocytes selected on antigen (see e.g., Carter et al. (2006) Nat Rev Immunol. 6(5), 343-357, 346-347.

Different Ig isotypes can be generated, other than then commonly used IgG1, with the humanized mice so as to tailor the produced antibody to different applications. For example, human IgG4 has limited capacity to activate effector functions of immune cells, and so, can be preferably used to block targets with limited immune activation. Radiolabelled IgG4 mAbs are particularly preferred for radioimmunotherapy and imaging, as a reduced nonspecific binding to normal tissue can be achieved with this isotope due to its poor binding to FcγRs. As another example, IgAs are preferred anti-infective reagents and, in addition, are potent activators of immune functions such as ADCC and phagocytosis.

Optimization of FcγRs Function of Antibodies

Various antibodies elicit effector functions following interactions between their Fc region and different Fc receptors (FcRs). The therapeutic efficacy of antibodies containing the Fc region can be optimized or diminished by engineering the interactions between the Fc region and various FcRs (e.g., FcγRs). For example, cytotoxic mAbs with enhanced engagement of activating FcγR and reduced binding to inhibitory FcγR can elicit increased antitumor and/or antiviral efficacy. As another example, mAbs that recruit and activate preferentially inhibitory FcγR can be used in the treatment of autoimmune diseases. As a further example, Fc-containing fusion molecules can be engineered for minimum interactions with some FcγRs and increased binding to some other FcR. As yet another example, an Fc fusion protein can be mutated so that the cellular toxicity and cell lysis triggered by FcγRs engagement does not occur.

The Fc-FcRs interaction can be tailored by, for example, substituting amino acids residues and/or altering the glycosylation pattern of Fc. It is known in the art that a number of specific amino acid residues of Fc (of for example, human IgG1) are critical for FcγR interaction (see e.g., Shields et al. (2001) J. Biol. Chem. 276, 6591-6604). These amino acids residues can be substituted to achieve a desired FcRs binding profile. The glycosylation pattern of the Fc region is important for effector functions of the molecule. Alteration of this Fc region glycosylation pattern can increase or decrease the efficacy of the molecule (see e.g., Teillaud (2005) Expert Opin Biol Ther. 5(Suppl 1) S15-27). For example, deglycosylation of the conserved Asn297 of each CH2 domain in the Fc region causes a domain conformation change that prevents FcγR binding.

Aptamer

Aptamers are oligonucleic acid or peptide molecules selected from a large random sequence pool to bind to specific target molecule. The small size of aptamers makes them easier to synthesize and chemically modify and enables them to access epitopes that otherwise might be blocked or hidden. And aptamers are generally nontoxic and weak antigens because of their close resemblance to endogenous molecules.

DNA or RNA aptamers consist of (usually short) strands of oligonucleotides. Oligonucleotide aptamers are DNA or RNA molecules that have been, for example, selected from vast populations of random sequences, through a combinatorial approach known as systematic evolution of ligands by exponential enrichment (SELEX). The selected sequences have the ability to recognize specific ligands by forming binding pockets and can bind to nucleic acids, proteins or small organic compounds. Generation, selection, and delivery of aptamers is within the skill of the art (see e.g., Lee et al. (2006) Curr Opin Chem. Biol. 10, 1-8). For example, capillary electrophoreses can be used to select aptamers with extremely well-defined affinity profiles. Aptamers can be selected not only against purified targets or antigens, but also against heterogeneous targets, such as whole cells (see e.g., Yan et al. (2005) Front Biosci 10, 1802-1827). Selection against complex targets, such as cell surfaces, allows the identification of aptamers even in the absence of known biomarkers. Furthermore, negative selection procedures with whole cells can yield aptamers that can finely discriminate between different cell types, for example transformed and normal cells. Incorporation of modified nucleotides into aptamers allows the selection of aptamers with increased affinities and reduced labilities.

Peptide aptamers are proteins that are designed to interfere with, for example, other protein interactions inside cells (see e.g., Hoppe-Seyler and Butz (2000) J Mol. Med. 78(8), 426-430, reviewing peptide aptamers). Peptide aptamers consist of a short variable peptide domain, attached at both end to a protein scaffold. They consist of a variable peptide loop attached at both ends to a protein scaffold. This double structural constraint can greatly increases the binding affinity of the peptide aptamer to levels comparable to an antibody's (nanomolar range). The variable loop length is typically comprised of 10 to 20 amino acids, and the scaffold can be any protein which have good solubility and compacity properties. For example, the bacterial protein Thioredoxin-A can be used as a scaffold protein, the variable loop being inserted within the reducing active site, which is a -Cys-Gly-Pro-Cys-loop in the wild protein, the two Cysteins lateral chains being able to form a disulfide bridge. Peptide aptamers selection can be made using various systems, including the yeast two-hybrid system. Protein aptamers can also be used to temporally and spatially regulate protein function in cells and organisms. For example, the ligand-regulated peptide (LiRP) system provides a general method where the binding activity of intracellular peptides is controlled by a cell-permeable small molecule (see e.g., Binkowski (2005) Chem & Biol. 12(7), 847-55).

Antibody Production

Engineering, generation, and screening of various types of antibodies is well known in the art. See e.g., Carter (2006) Nat Rev Immunol. 6(5), 343-357; Teillaud (2005) Expert Opin Biol Ther. 5(Suppl 1) S15-27; Subramanian, ed. (2004) Antibodies: Volume 1: Production and Purification, Springer, ISBN 0306482452; Subramanian, ed. (2001) Manufacturing of Gene Therapeutics—Methods, Processing, Regulation and Validation, Springer, ISBN 0306466805; Lo, ed. (2003) Antibody Engineering Methods and Protocols, Humana Press, ISBN 1588290921. These methods can generally be used for the generation of antibodies having similar affinity and specificity and which are functionally equivalent to those used in the working examples.

While antibody therapeutics are conventionally produced in mammalian cells—commonly Chinese hamster ovary cells, NS0 mouse myeloma cells or hybridoma cells—alternative hosts for production can also be employed (e.g., *E. coli*, other microorganisms, insect cells, and transgenic plants and animals). See generally Carter et al. (2006) Nat Rev Immunol. 6(5), 343-357. For example, antibody fragments can be produced at gram-per-liter titres by *E. coli* fermentation.

Once produced, immunopeptides can be tested for SAM and/or neuropilin 1 recognition by various procedures including Western blot or immunoprecipitation analysis by standard methods, as described in the references above. Preferred antigen-binding affinity ranges from a Kd of, for example, 0.001 to 100 nM, 0.01 to 50 nM, and 0.08 nM to 32 nM.

Numerous interdependent properties of the antibodies described herein can be tuned to improve their clinical and/or diagnostic efficacy. These properties include, but are not limited to, immunogenicity, antigen binding specificity and affinity, effector functions and other biological activities, pharmacokinetics, molecular architecture, internalization after cell binding, and biophysical properties. For example, display libraries and structure-based design (i.e., rational design) can be used, either individually or in combination, for the optimization of antibody therapeutics. See e.g., Carter et al. (2006) Nat Rev Immunol. 6(5), 343-357, 348; Wu et al. (2005) Nature Biotech 23(9), 1137-1146. Such optimization can include, for example, minimizing adverse-immunogenicity risk; improving antigen selectivity; increasing species cross-reactivity; increasing or decreasing antigen binding affinity; increasing potency; increasing or decreasing effector functions; increasing or decreasing plasma half-life; increasing or decreasing internalization efficiency; increase chemical, proteolytic, and thermodynamic stability; and improve solubility and folding kinetics. As a specific example, phage-display libraries can be used to select antibody fragments optimized for robust expression, high stability, and solubility. As another specific example, phage-display libraries can be used for affinity maturation of antibodies and increased in vitro biological potency. See e.g., Carter et al. (2006) Nat Rev Immunol. 6(5), 343-357, 350. Such increases can increase efficacy as well as reduce dosage or frequency of administration.

The terminal half-life of antibodies in plasma can be tuned over a wide range to fit clinical goals. The antibody half-life can be engineered to be between several minutes to several weeks. It can also be desirable to increase the terminal half-life of an antibody to improve efficacy, to reduce the dose or frequency of administration, or to improve localization to the target. Alternatively, it can be advantageous to do the converse—that is, to decrease the terminal half-life of an antibody—to reduce whole body exposure or to improve the target-to-non-target binding ratios.

Monoclonal antibody fragments can be engineered to tailor pharmacokinetics and allow selection of optimized versions for various applications, such as imaging or therapeutics. See e.g., Wu et al. (2005) Nature Biotech 23(9) 1137-1146. For example, scFVs (around 25 kDa) are diabodies (around 55 kDa) below the threshold for first-pass renal clearance and can show terminal half-lives on the order of, for example, several hours. Larger fragments such as minibodies or small immunoproteins (e.g., scFVs fused to single constant domains of IgG, 80 kDa) show intermediate clearance rate and reach higher tissue uptake levels. Still larger fragments include scFVs fused to intact Fc domains (scFVs-Fcs, 110-120 kDa) have similar pharmokinetics to intact monoclonal antibodies because of the Fc region, including the neonatal Fc receptor binding site.

Decreasing antibody terminal half-life can, for example, allow tumor imaging by positron emission tomography. For example, the terminal half-life of IgG can be increased or decreased by tailoring the interaction between IgG and its salvage receptor, FcRn. See e.g., Carter et al. (2006) Nat Rev Immunol. 6(5), 343-357, 353. The terminal half-life of antibody fragments, usually shorter than non-fragments, can be extended by binding to longer-lived molecules, such as IgG and serum albumin, or conjugation to molecules such as polyethylene glycol (i.e., PEGylation). PEGylated antibody fragments provide the advantage of, for example, lack of undesirable Fc-mediated effects, reduction in the risk of immunogenicity, and a moderate reduction in cost.

Antibodies can be altered or selected so as to achieve efficient antibody internalization. Further, antibody-drug conjugates can increase the efficiency of antibody internalization. Efficient antibody internalization can be desirable for certain applications, such as for delivery of cytotoxic drugs and immunoliposomes. Removal of the target antigen from the cell surface prevents the further binding of any ligands and can therefore be a desirable outcome when using a receptor antagonist, in for example, antibody therapeutics. By contrast, rapid antibody internalization after cell binding can be undesirable where the therapeutic strategy requires effector functions.

Conjugation of antibodies to a variety of agents, including drugs, toxins, and radionuclides, is well known in the art. See generally, Wu et al. (2005) Nat. Biotechnol. 23(9), 1137-1146; McCarron et al. (2005) Mol Interv 5(6), 368-380; Niemeyer (2004) Bioconjugation Protocols, Strategies and Methods, Humana Press, ISBN 1588290980; Hermanson (1996) Bioconjugate Techniques, Academic Press, ISBN 0123423368.

Antibody Uses

Among the various uses for antibodies described herein are, for example, function inhibitor, expression inhibitor, detector agent, diagnostic agent, purification agent, therapeutic agent, and imaging agent.

Antibodies of this invention can be used as inhibitors of SAM and/or neuropilin 1 function and expression. For example, antibody inhibitors of the insulin secretion pathway can target, directly or indirectly, any factor or component involved in the biological cascade which results in promoting pancreatic islet hormone release. Inhibitors of SAM and/or neuropilin 1 include inhibitors targeting neuroligin 1, neuroligin 2, neuroligin 3, neuroligin 4X, neuroligin 4Y, neurexin 1$\alpha$, neurexin 2$\alpha$, neurexin 3$\alpha$, neurexin 1$\beta$, neurexin 2$\beta$, neurexin 3$\beta$, SynCam, Thy-1, and neuronal pentraxin and/or neuropilin 1. Standard methods using antibodies can be used to detect and quantitate SAM and/or neuropilin 1 expression, including but not limited to: radioimmunoassays, receptor assays, enzyme immunoassays, cytochemical bioassays, ligand assays, immunoradiometric assays, fluoroimmunoassays, and enzyme-linked immunosorbent assays.

The antibodies described herein can be used to detect the presence and quantity of the substance against which they were raised. For example, the antibodies of the invention can be used to detect SAM and/or neuropilin 1 protein in a biological sample. Various protocols well known in the art can be utilized for these purposes, including but not limited to, a Western blot test (to detect a substance in a solution) or an immunofluorescence test (to detect a substance in a whole cell). For example, antibodies described herein can be used in an immunoassay to monitor the level of a SAM and/or neuropilin 1 protein produced by a mammal (e.g., to determine the amount or subcellular location of an SAM and/or neuropilin 1 protein).

In biochemical applications, antibodies can be used for immunological identification of proteins, using, for example, the Western blot method. A similar technique is used in ELISPOT and ELISA assays, in which detection antibodies are used to detect cell secretions such as cytokines or antibodies. Antibodies can also be used to separate proteins (and anything bound to them) from the other molecules in a cell lysate. Antibodies can also be used in immunohistochemical staining.

Antibodies of the invention can also be used to purify a substance with techniques such as immunoprecipitation and affinity chromatography.

Antibodies described herein can be used as therapeutic agents, either alone or conjugated to another active agent. Therapeutic use of antibodies is known in the art. See e.g., Carter (2006) Nat Rev Immunol. 6(5), 343-357; Subramanian, ed. (2004) Antibodies vol. 2 Novel Technologies and Therapeutic Use, Springer, ISBN 0306483157. Antibodies can be used therapeutically by nature of their ability to bind to cell-specific antigens and induce an immunological response against the target cell, for example an islet Beta cell. Such antibodies can also be modified for delivery of, for example, a toxin, radioisotope, cytokine or other active conjugate. Bispecific antibodies can also be designed to bind with their Fab regions both to a target antigen and to a conjugate or effector cell.

The antibodies of the invention can be used in a variety of imaging and/or localization applications.

The methods discussed above are well known and will be understood by those skilled in the art to require a reasonable amount of experimentation to optimize the interaction between antibodies and antigens and the detection of the antigens by the antibodies. See e.g., Wild (2005) The Immunoassay Handbook, 3d ed., Elsevier Science, ISBN 0080445268; Coligan (2005) Short Protocols in Immunology, John Wiley & Sons, ISBN 0471715786; Brent et al., ed. (2003) Current Protocols in Molecular Biology, John Wiley & Sons Inc, ISBN 047150338X; Ausubel et al., ed. (2002) Short Protocols in Molecular Biology 5th Ed., Current Protocols, ISBN 0471250929.

Radioimaging and Radioimmunotherapy

Radionucleotides can be coupled to the antibodies described herein, thus facilitating a variety of imaging and therapeutic protocols. See e.g., Wu et al. (2005) Nature Biotech 23(9), 1137-1146. As an imaging example, radioimmunoscintigraphy using gamma cameras or single photon emmission tomography requires coupling of gamma emitting isotopes (e.g., 99 mTc, 123I, 111In) to an antibody. Positron emission tomogrpahy (PET) relies on attachment of positron emitters (e.g., 18F, 64Cu, 68Ga, 86Y, 124I) to antibodies. Targeted delivery of beta emitters (e.g., 131I, 90Y, 177Lu, 67Cu) or alpha-emitting radionucleotides (e.g., 213Bi, 211At) through conjugation to an antibody is a touchstone for effective radioimmunotherapy procedures. Radioimmunoimaging can be used in conjunction with radioimmunotherapy as a means for evaluating targeting and dosimetry. Generally, antibody fragments are desirable for immunoimaging applications due to their relatively shorter circulating half-life, tissue penetration, and more homogenous distribution within tissues.

Antibodies can be coupled to radionuclides for radioimmunotherapy applications. Generally, dose delivered to the target is balanced against exposure of normal organs and tissues to radiation. Both alpha and beta emitters with a variety of energy transfer properties, half-lives and emission rates can be used for radioimmunotherapy. See e.g., Milenic et al. (2004) Nat Rev Drug Discov 3, 488-499. Examples of toxic radionuclides that can be coupled to the antibody include 131I, 90Y, and 177Lu.

Coupling radionucleotides and proteins is well known in the art and can be accomplished, for example, through conjugation to existing or genetically introduced cysteine residues in the antibody. See e.g., Wu et al. (2005) Nature Biotech 23(9), 1137-1146.; McCarron et al. (2005) Mol Interv 5(6), 368-380; Niemeyer (2004) Bioconjugation Protocols, Strategies and Methods, Humana Press, ISBN 1588290980; Hermanson (1996) Bioconjugate Techniques, Academic Press, ISBN 0123423368. Other examples include labeling of hexahistidine-tagged recombinant proteins and covalent modification of monoclonal antibody binding sites for ligand binding. A further coupling example is incorporation of enyzmatically labile linkers between radiometal and antibody that allow release and clearance of the conjugated radiometal from circulating conjugates, with cleavage by exogenous or endogenous enzymes.

It can also be desirable to utilize pretargeting radioimmunotherapy. Under this approach, antibody-directed localization and radionuclide delivery are separated physically and temporally. First, the antibody conjugate is administered so as to bind the target. A clearing agent can be applied to clear the blood. Then, a low molecular weight radioactive ligand that binds the antibody conjugate is administered. This approach effectively separates the slow distribution of the antibody moiety from rapid binding and elimination of the radioisotope-tagged ligand. For example, an antibody-streptavidin conjugate can be employed in the first step, followed by a radiolabeled biotin derivative. See e.g., Sharkey et al. (2005) Clin Cancer Res 11, 7109s-7121s.

It can also be desirable to utilize antibody-directed enzyme prodrug therapy (ADEPT). See e.g., Wu et al. (2005) Nature Biotech 23(9), 1137-1146. This alternate form of pretargeting is a two-step process in which, first, an antibody-enzyme conjugate is administered that localizes on or in the target and clears from systemic circulation over time. Once the target/nontarget ration is sufficiently high, a prodrug is given that is converted to an active drug by the targeted enzyme. One advantage of this approach is the ability to use prodrugs that would be too toxic in untargeted form.

Antibody Administration

The biomolecules described herein can be used therapeutically either as exogenous materials or as endogenous materials. Exogenous agents are those produced or manufactured outside of the body and administered to the body. Endogenous agents are those produced or manufactured inside the body by some type of device (biologic or other) for delivery to within or to other organs in the body.

Administration of biomolecules by a variety of methods is well known in the arts. Administration can include, for example, methods involving direct injection (eg, systemic or stereotactic), implantation of cells engineered to secrete the factor of interest, drug-releasing biomaterials, implantable matrix devices, implantable pumps, injectable gels and hydrogels, liposomes, micelles (e.g., up to 30 μm), microspheres (e.g., 1-100 μm), reservoir devices, etc.

A safe and effective amount of an anti-SAM and/or neuropilin 1 antibody is, for example, that amount that would cause the desired therapeutic effect in a patient while minimizing undesired side effects. The dosage regimen will be determined by skilled clinicians, based on factors such as the exact nature of the condition being treated, the severity of the condition, the age and general physical condition of the patient, and so on.

The compositions of the present invention can include one or more pharmaceutically acceptable vehicles for said compound(s). Such pharmaceutical formulations are discussed in depth below.

Adverse reactions to antibody administration in a subject can be attenuated in a variety of ways known in the art. For example, infusion reactions (e.g., fever, chills, headaches, vomiting, and diarrhoea) can be attenuated by humanization, attentuating effector functions (e.g., antibody-dependent cell-mediated cytotoxicity and complement dependent cytotoxicity), premedication, and by incremental increase in the rate of infusion of antibody formulation. See e.g. Carter et al. (2006) Nat Rev Immunol. 6(5), 343-357. As another example, Fc-mediated reactions, such as acute and severe influenza-like syndrome, can be largely overcome by attenuating the interaction between the Fc region of the antibody and the receptors for the antibody (e.g., IgG receptors; FcγRs) expressed by the patient. In general, increasing the potency of the antibody or extending its half-life in plasma can allow the dose or frequency of administration to be reduced, with the associated benefits of improved quality of life and/or convenience for the patient, and/or reduced cost of the drug.

Parenteral

The biomolecules described herein can be administered parenterally, including intravenous, intramuscular, subcutaneous, and intraperitoneal injections.

Excipients, commonly used in the parenteral delivery of small drug molecules, including solubility enhancers, osmotic agents, buffers, and preservatives, can also be included in biomolecule formulations. Inclusion of antiaggregation and antiadsorption agents, such as surfactants and albumin, when formulating and delivering biomolecules can add increased stability and decrease the risk of the active biomolecule interacting with an interface, which can lead to unfolding, aggregation, and/or precipitation. The biomolecule can be lyophilized for added stability during storage, and re-processed before parenteral administration.

For example, antibody delivery can be by intravenous infusion, usually entailing multiple doses. Local, controlled release methods for antibody delivery are also known in the art (see e.g., See e.g., Raza et al. (2005) Expert Opin Biol Ther. 5(4), 477-494; Stayton et al. (2005) Orthod Craniofacial Res 8, 219-225; Grainger (2004 Expert Opin Biol Ther. 4(7), 1029-44; Varde and Pack (2004) Expert Opin Biol Ther. 4(1), 35-51; Whittlesey and Shea (2004) Exp Neurol. 190(1), 1-16).

Antibodies can be administered in an amount of, for example, about [[0.05 mg to about 2.5 mg]] per injection. As another example, antibodies can be injected at a concentration of about [[0.1 mg to about 1 mg]] per injection. Preferably, immunopeptide inhibitors are injected at a concentration of about [[0.3 mg to about 0.5 mg]] per injection.

Cell Implantation

Antibodies described above can be delivered by implanting antibody-producing hybridoma cells (see e.g., Bromsamle et al. (2000) J. Neuroscience 20, 8061-8068).

Oral

Oral administration of the biomolecular agents described herein provides ease of administration as well as the ability to achieve systemic distribution of the agent. A variety of means to avoid degradation of the relatively fragile bioagents of the present invention are known to the art. Carrier-based systems for biomolecule delivery can be used in conjunction with oral delivery. For example, bioadhesive systems that adhere to the intestinal epithelium are available (see e.g., Ramdas et al. (1999) J. Biomater. Appl. 13, 290-296, describing alginate encapsulated bioadhesive chitosan microspheres for intestinal drug delivery). As another example, certain devices that can release formulations in the intestine for several days or several weeks are available.

Pulmonary

Pulmonary delivery of macromoles and/or drugs, such as the biomolecules described herein, provide for relatively easy, non-invasive administration to the circulatory system for systemic circulation, airway surface, and/or airway cells (see e.g., Cryan (2004) AAPS J. 7(1) article 4, E20-41, providing a review of pulmonary delivery technology). Advantages of pulmonary delivery include noninvasiveness, large surface area for absorption (~75 m2), thin (~0.1 to 0.5 μm) alveolar epitheliuem permitting rapid absorption, absence of first pass metabolism, decreased proteolytic activity, rapid onset of action, and high bioavailablity. Drug formulations for pulmonary delivery, with or without excipients and/or a dispersible liquid, are known to the art. Carrier-based systems for biomolecule delivery, such as polymeric delivery systems, liposomes, and micronized carbohydrates, can be used in conjunction with pulmonary delivery. Penetration enhancers (e.g., surfactants, bile salts, cyclodextrins, enzyme inhibitors (e.g., chymostatin, leupeptin, bacitracin), and carriers (e.g., microspheres and liposomes) can be used to enhance uptake across the alveolar epithelial cells for systemic distribution.

Various inhalation delivery devices, such as metered-dose inhalers, nebulizers, and dry-powder inhalers, that can be used to deliver the biomolecules described herein are known to the art (e.g., AErx (Aradigm, Calif.); Respimat (Boehringer, Germany); AeroDose (Aerogen Inc., CA)). As known in the art, device selection can depend upon the state of the biomolecule (e.g., solution or dry powder) to be used, the method and state of storage, the choice of excipients, and the interactions between the formulation and the device.

Dry powder inhalation devices are particularly preferred for pulmonary delivery of protein-based agents (e.g., Spinhaler (Fisons Pharmaceuticals, NY); Rotohaler (GSK, NC); Diskhaler (GSK, NC); Spiros (Dura Pharmaceuticals, CA); Nektar (Nektar Pharmaceuticals, CA)). Dry powder formulation of the active biological ingredient to provide good flow, dispersability, and stability is known to those skilled in the art.

Pumps

The biomolecules described herein can be delivered, for example, via a surgically implanted osmotic pump or cannula system.

Carrier Delivery Systems

Carrier delivery systems encapsulate the biomolecule of interest and provide controlled release of the agent over extended periods of time. Generally a carrier includes molecules conjugated to, mixed with, or used for encapsulating biomolecular agents. Carrier-based systems for biomolecular agent delivery can: tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; and/or improve shelf life of the product.

Polymeric release systems can be used to deliver small molecule drugs, pharmocologic agents, proteins, enzymes, peptides, polypeptides, nucleotides, polynucleotides, oligonucleotides, antisense oligonucleotides, nucleosides, antibodies, viral and nonviral vectors, etc. for a variety of purposes discussed above (see Whittlesey and Shea (2004) Experimental Neurology 190, 1-16). Polymeric systems can also be designed to deliver multiple biomolecules that can act synergistically or sequentially on cellular processes. Polymeric delivery systems can maintain therapeutic levels of the biomolecular agents described herein, reduce harmful side effects, decrease the amount of biomolecule required, decrease the number of dosages, facilitate delivery of agents with short in vivo half-lives, and overcome barriers associated with low oral and transdermal bioavailabilities. Release rates can be controlled by altering the pore size, structure, and polymer contents of synthetic polymers such as the nondegradable synthetic polymer EVAc and the degradable synthetic polymer polyester PLGA. Furthermore, the degradation of the material itself serves to govern release profiles, providing an additional level of control over release rate. Polymeric delivery systems described herein can be tailored for release durations of, for example, minutes, hours, days, weeks, and even years depending upon the physical and chemical properties of the delivered molecule, the polymer employed, and the processing conditions used during fabrication.

Both natural (e.g., collagen) and synthetic polymers (e.g., silicone, poly-lactide-co-glycolide (PLGA), and polyethylene vinyl-co-acetate (EVAc)) can be utilized for the local and systemic delivery of biomolecules. Biodegradable polymers are preferable for biomolecule delivery because the device can disappear over time, eliminating the need for surgical retrieval. PLGA is a widely used biopolymer due to its commercial availabilty, controllable degradation rate, proven biocompatibility, and FDA approval (see e.g., Lu et al. (2000) Biomaterials 21, 1837-1845). Polyanhydrides are a similar class of degradeable polymer that can be used for biomolecule delivery.

Microspheres

Polymeric microspheres can facilitate delivery of the biomolecules described herein. For example, sustained delivery microspheres can be stereotactically injected to over express an encoded protein or release a biomolecular inhibitor of that protein at a target site. Microspheres are produced using naturally occurring or synthetic polymers to produce particulate systems in the size range of 0.1 to 500 μm. Generally, microspheres are physically and chemically more stable than liposomes and allow for higher agent loading. Polymeric micelles and polymeromes are polymeric delivery vehicles with similar characteristics to microspheres and can also facilitate encapsulation and delivery of the biomolecules described herein.

Fabrication, encapsulation, and stabilization of microspheres for a variety of biomolecule payloads are within the skill of the art (see e.g., Varde & Pack (2004) Expert Opin. Biol. 4(1)35-51). Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme).

Release rate of microspheres can be tailored by type of polymer, polymer molecular weight, copolymer composition, excipients added to the microsphere formulation, and microsphere size.

The type of polymer and the way in which it degrades affects agent release kinetics. Bulk-eroding polymers, such as PLGA, readily allow permeation of water into the polymer matrix with polymer degradation throughout the matrix. Bulk erosion typically results in biphasic or triphasic release profiles. In contrast, surface eroding polymers, such as polyanhydrides, are composed of relatively hydrophobic monomers linked by labile bonds, resulting in resistance to water permeation into the polymer bulk but rapid degradation at the polymer/water interface via hydrolysis. Typically, the encapsulated agent is released from the surface degradation, with the largest rate of release at the beginning and, as the surface area decreases, asymptotically decreasing.

Generally, encapsulated agent release rate decreases with increased polymer molecular weight in bulk-eroding polymers but has little effect in surface-eroding polymers. Microsphere size also affects release rate, with the rate of flux of the biomolecule out of the matrix increasing with decreased particle size. Microspheres can be formulated to contain one or more polymers and the relative ratio of each monomeric unit can affect the release rate.

Excipients can be added to the microsphere formulation to stabilize the emulsion during fabrication and to stabilize the biomolecule during fabrication and/or release. In the case of microsphere encapsulated proteins, addition of excipients, such as PEG, carbohydrates, and buffering salts (e.g., magnesium hydroxide), can prevent aggregation and stabilize the folded protein structure. As another example, encapsulated protein biomolecules in PLGA microspheres in the presence of the hydrophilic excipient mannitol can enhance biomolecular stability. Excipients can also impact release rate. For example, PVA in the biomolecule solution can stabilize the primary emulsion and provide more uniform distribution throughout the matrix, prevent coalescence of inner aqueous-phase droplets, and decrease initial release burst and overall release rate. Coating of microspheres can be used to alter in vivo properties. For example, coating PLGA microspheres with DPPC can decrease uptake of the biomolecule cargo into macrophages. As another example, coating particles with mucoadhesive polymers such as chitosan and hydroxypropylcellulose can increase residency time of pulmonary carriers.

Microspheres encapsulating the biomolecules described herein can be administered in a variety of means including parenteral, oral, pulmonary, implantation, and pumping device. For single walled polymeric microspheres, the biphasic release rate of the bioactive molecule depends on the ratio of surface-associated to encapsulated drug. Typically an initial "burst release" (resulting from of the incorporated biomolecule being left on the surface of the microsphere) is followed by a more prolonged release (i.e., biphasic release), with rates dictated by the polymer used. Double-walled polymeric micropsheres exhibit a more linear release rate (see e.g., Yang et al. (2003) J. Controlled Release 88, 201-213).

Hydrogels

Polymeric hydrogels, composed of hydrophillic polymers such as collagen, fibrin, and alginate, can also be used for the sustained release of incorporated biomolecules (see e.g., Sakiyama et al. (2001) FASEB J. 15, 1300-1302). Biomolecules incorporated into the hydrogel can stimulate cellular function directly from the matrix or following release.

Polymeric Implants

Three-dimensional polymeric implants, on the millimeter to centimeter scale, can be loaded with biomolecules (see e.g., Teng et al (2002) Proc. Natl. Acad. Sci. U.S.A. 99, 3024-3029). These polymeric implants can serve as structural for cell adhesion and tissue formation while also providing controlled release of biomolecules. A polymeric implant typically provides a larger depot of the bioactive factor. The implants can also be fabricated into structural supports, tailoring the geometry (e.g., shape, size, porosity) to the application. The porosity of the scaffold can influence cell seeding and cell infiltration from the surrounding tissue. Extracellular matrix proteins can be incorporated in or on the scaffold to influence cell adhesion and migration. For example, polymeric delivery vehicles shaped into structural supports, such as guidance channels or bridges, can provide architectural organization and biochemical factors to stimulate tissue formation. As another example, polymeric delivery systems can provide support structures for stem cell adhesion coupled with release of one or more proteins or other biomolecules to stimulate differentiation to a specific cell fate. Three-dimensional polymeric implants can be formed, for example, by direct casting of the polymer and drug or by processing loaded microspheres into a three-dimensional structure. Three-dimensional polymeric implants for biomolecule delivery can be formulated in a variety of means known to the art including, but not limited to, emulsion methods, solvent casting, and carbon dioxide foaming process (see e.g., Whittlesey and Shea (2004) Experimental Neurology 190, 1-16). Implantable matrix-based delivery systems are also commercially available in a variety of sizes and delivery profiles (e.g., Innovative Research of America, Sarasota, Fla.).

As an alternative to release, biomolecules can be immobilized on or in polymeric delivery systems. This approach includes substrate mediated delivery and solid-phase delivery. Generally, the polymeric substrate functions to support cell adhesion and place the biomolecular cargo directly in the cellular microenvironment (see e.g., Whittlesey and Shea (2004) Experimental Neurology 190, 1-16). Substrate mediated delivery can be used to deliver both nonviral and viral vectors. This approach is especially preferable for viral vector delivery as it mimics how many such vectors associate with the extracellular matrix as a means to facilitate cellular binding and internalization. For example, implantation of an adenovirus-modified collagen gel can result in transduction throughout the matrix with a differing delivery profile as compared to direct injection, thus localizing gene delivery and avoiding distal side effects (see e.g., Levy et al. (2001) Gene Ther. 8, 659-667). As another example, biomolecules can be delivered from polymer-coated stents and microcoils (se e.g., Abrahams et al. (2002) Stroke 33, 1376-132; Klugherz et al. (2002) Hum. Gene Ther. 13, 443-454.

In formulating polymeric release systems, various additives can be included to stabilize the biomolecule to be delivered. Such additives and measures include, for example, carbohydrate sugars, polyethylene glycol, complexation with metal ions, and coencapsulation with a weak base to minimize the pH reduction during degradation.

"Smart" Polymeric Carriers

The biomolecular therapeutic agents described herein can be delivered to intracellular targets via so-called "smart" polymeric carriers. See e.g., Stayton et al. (2005) Orthod Craniofacial Res 8, 219-225; Wu et al. (2005) Nature Biotech (2005) 23(9), 1137-1146. Generally, carriers of this type utilize polymers that are hydrophilic and stealth-like at physiological pH, but become hydrophobic and membrane-destabilizing after uptake into the endosomal compartment (i.e., acidic stimuli from endosomal pH gradient) where they enhance the release of the cargo molecule into the cytoplasm. The design of the smart polymeric carrier can incorporate pH-sensing functionalities, hydrophobic membrane-destabilizing groups, versatile conjugation and/or complexation elements to allow the drug incorporation, and an optional cell targeting component. Potential therapeutic macromolecular cargo includes, but is not limited to, peptides, proteins, antibodies, polynucleotides, plasmid DNA (pDNA), aptamers, antisense oligodeoxynucleotides (ASODN), silencing RNA, and ribozymes. As an example, smart polymeric carriers can enhance the cytoplasmic delivery of antibody-targeted conjugates that are internalized through receptor mediated endocytosis. As another example, smart polymeric carriers can enhance cytoplasmic delivery of protein therapeutics.

Polymeric carriers include, for example, the family of poly (alkylacrylic acid) polymers, specific examples including poly(methylacrylic acid), poly(ethylacrylic acid) (PEAA), poly(propylacrylic acid) (PPAA), and poly(butylacrylic acid) (PBAA), where the alkyl group progressively increased by one methylene group.

Such polymeric carriers can be designed to provide a range of pH profiles and membrane-destabilizing activities, allowing their molecular properties to be matched to specific drugs and loading ranges. For example, the pH profile can be controlled by the choice of the alkylacrylic acid monomer and by ratio of the carboxylate-containing alkylacrylic acid monomer to alkylacrylate monomer. Similarly, the membrane destabilizing activity can be controlled by the lengths of the alkyl segment on the alkylacrylic acid monomer and the alkylacrylate monomer.

Smart polymeric carriers with potent pH-responsive, membrane destabilizing activity can be designed to be below the renal excretion size limit. For example, poly(EAA-co-BA-co-PDSA) and poly(PAA-co-BA-co-PDSA) polymers exhibit high hemolytic/membrane destabilizing activity at the low molecular weights of 9 and 12 kDa, respectively.

Various linker chemistries are available to provide degradable conjugation sites for proteins, nucleic acids, and/or targeting moieties. For example, pyridyl disulfide acrylate (PDSA) monomer allow efficient conjugation reactions through disulfide linkages that can be reduced in the cytoplasm after endosomal translocation of the therapeutics.

Liposomes

The drug carrying capacity and release rate of liposomes can depend on the lipid composition, size, charge, drug/lipid ratio, and method of delivery. Conventional liposomes are composed of neutral or anionic lipids (natural or synthetic). Commonly used lipids are lecithins such as (phosphatidylcholines), phosphatidylethanolamines (PE), sphingomyelins, phosphatidylserines, phosphatidylglycerols (PG), and phosphatidylinositols (PI). A commonly used method of encapsulation is rehydration of a lipid film with a biomolecule solution followed by freeze-thawing and extrusion. Other techniques for forming biomolecule liposomes include the proliposome technique (see e.g., Galovic et al. (2002) Eur. J. Pharm. Sci. 15, 441-448) and the crossflow injection technique (see e.g., Wagner et al. (2002) J. Liposome Res. 12, 259-270). Liposome encapsulation efficiency can be monitored and optimized through various procedures known to the art, including differential scanning calorimetry (see e.g., Lo et al. (199%) J. Pharm. Sci. 84, 805-814).

Targeted liposomes and reactive liposomes can also be used to deliver the biomolecules of the invention. Targeted liposomes have targeting ligands, such as monoclonal antibodies or lectins, attached to their surface, allowing interaction with specific receptors and/or cell types. Reactive or polymorphic liposomes include a wide range of liposomes, the common property of which is their tendency to change their phase and structure upon a particular interaction (eg, pH-sensitive liposomes) (see e.g., Lasic (1997) Liposomes in Gene Delivery, CRC Press, FL).

SAM and Neuropilin 1 Proteins

In other aspects, the resent invention utilizes a purified SAM and Neuropilin 1 proteins encoded by a SAM and Neuropilin 1 nucleic acid or gene. A preferred form of SAM and Neuropilin 1 is a purified native SAM and Neuropilin 1 protein that has the deduced amino acid sequences of SEQ ID NOs. 1-18. Variants of native SAM and Neuropilin 1 proteins such as fragments, analogs and derivatives of native SAM and Neuropilin 1 proteins are also within the invention. Such variants include, e.g., a polypeptide encoded by a naturally occurring allelic variant of a native SAM or Neuropilin 1 gene, a polypeptide encoded by an alternative splice form of a native SAM or Neuropilin 1 gene, a polypeptide encoded by a homolog of a native SAM or Neuropilin 1 gene, and a polypeptide encoded by a non-naturally occurring variant of a native SAM or Neuropilin 1 gene.

SAM and Neuropilin 1 protein variants have a peptide sequence that differs from a native SAM or Neuropilin 1 protein in one or more amino acids. The peptide sequence of such variants can feature a deletion, addition, or substitution of one or more amino acids of a native SAM or Neuropilin 1 polypeptide. Amino acid insertions are preferably of about 1, 2, 3, 4, 5, 6, 7, 8, 9, 10, 11, 12, 13, 14, 15, 16, 17, 18, 19, 20, 21, 22, 23, 24 to 25 contiguous amino acids, and deletions are preferably of about 1, 2, 3, 4, 5, 6, 7, 8, 9, 10, 11, 12, 13, 14, 15, 16, 17, 18, 19, 20, 21, 22, 23, 24 to 25 contiguous aminoacids. In some applications, variant SAM and Neuropilin 1 proteins substantially maintain a SAM or Neuropilin 1 protein functional activity (e.g., association with pancreatic disease including diabetes and pancreatic cancer). For other applications, variant SAM and Neuropilin 1 proteins lack or feature a significant reduction in an SAM and Neuropilin 1 protein functional activity. Where it is desired to retain a functional activity of native SAM or Neuropilin 1 protein, preferred SAM and Neuropilin 1 protein variants can be made by expressing nucleic acid molecules that feature silent or conservative changes. Variant SAM and Neuropilin 1 proteins with substantial changes in functional activity can be made by expressing nucleic acid molecules within the invention that feature less than conservative changes.

SAM and Neuropilin 1 protein fragments corresponding to one or more particular motifs and/or domains or to arbitrary sizes, for example, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 200, 250, 300, 400, 500, 600, 700, 800, 900, 1000, 1100, 1150 and 1200 amino acids in length are intended to be within the scope of the present invention. Isolated portions of SAM and Neuropilin 1 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a SAM or Neuropilin 1 protein of the present invention may be arbitrarily divided into fragments of desired length with no overlap of the fragments, or preferably divided into overlapping fragments of a desired length. The fragments can be produced (recombinantly or by chemical synthesis) and tested to identify those fragments which can function as either agonists or antagonists of a native SAM and Neuropilin 1 protein.

Another aspect of the present invention concerns recombinant forms of the SAM and Neuropilin 1 proteins. Recombinant polypeptides preferred by the present invention, in addition to native SAM and Neuropilin 1 protein, are encoded by a nucleic acid that has at least 85% sequence identity (e.g., 85%, 86%, 87%, 88%, 89%, 90%, 91%, 92%, 93%, 94%, 95%, 96%, 97%, 98%, and 99%) with gene sequences encoding proteins having SEQ ID NOs: 1-19. In a preferred embodiment, variant SAM and Neuropilin 1 proteins have one or more functional activities of native SAM or Neuropilin 1 protein.

SAM and Neuropilin 1 protein variants can be generated through various techniques known in the art. For example, SAM and Neuropilin 1 protein variants can be made by mutagenesis, such as by introducing discrete point mutation(s), or by truncation. Mutation can give rise to a SAM or Neuropilin 1 protein variant having substantially the same, or merely a subset of the functional activity of a native SAM or Neuropilin 1 protein. Alternatively, antagonistic forms of the protein can be generated which are able to inhibit the function of the naturally occurring form of the protein, such as by competitively binding to another molecule that interacts with SAM and Neuropilin 1 protein. In addition, agonistic forms of the protein may be generated that constitutively express on or more SAM or Neuropilin 1 functional activities. Other variants of SAM and Neuropilin 1 proteins that can be generated include those that are resistant to proteolytic cleavage, as for example, due to mutations which alter protease target sequences. Whether a change in the amino acid sequence of a peptide results in a SAM or Neuropilin 1 protein variant having one or more functional activities of a native SAM or Neuropilin 1 protein can be readily determined by testing the variant for a native SAM and Neuropilin 1 protein functional activity.

As another example, SAM or Neuropilin 1 protein variants can be generated from a degenerate oligonucleotide sequence. Chemical synthesis of a degenerate gene sequence can be carried out in an automatic DNA synthesizer, and the synthetic genes then ligated into an appropriate expression vector. One purpose for a degenerate set of genes is to provide, in one mixture, all of the sequences encoding the desired set of potential SAM or Neuropilin 1 protein sequences. The synthesis of degenerate oligonucleotides is well known in the art (see, e.g., Narang, S A (1983) Tetrahedron 39:3; Itakura et al. (1981) RECOMBINANT DNA, PROC 3RD CLEVELAND SYMPOS. MACROMOLECULES, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, e.g., Scott et al. (1990) Science 249:386-390; Roberts et al. (1992) Proc. Natl. Acad. Sci. USA 89:2429-2433; Devlin et al. (1990) Science 249: 404-406; Cwirla et al. (1990) Proc. Natl. Acad. Sci. USA 87: 6378-6382; as well as U.S. Pat. Nos. 5,223,409; 5,198,346; and 5,096,815).

Similarly, a library of coding sequence fragments can be provided for a SAM or Neuropilin 1 gene clone in order to generate a variegated population SAM or Neuropilin 1 protein fragments for screening and subsequent selection of fragments having one or more native SAM or Neuropilin 1 protein functional activities. A variety of techniques are known in the art for generating such libraries, including chemical synthesis. In one embodiment, a library of coding sequence fragments can be generated by (i) treating a double-stranded PCR fragment of a SAM or Neuropilin 1 gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with SI nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of SAM or Neuropilin 1 gene variants. The most widely used techniques for screening large gene libraries typically involve cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins. To screen a large number of protein mutants, techniques that allow one to avoid the very high proportion of non-functional proteins in a random library and simply enhance the frequency of functional proteins (thus decreasing the complexity required to achieve a useful sampling of sequence space) can be used. For example, recursive ensemble mutagenesis (REM), an algorithm that enhances the frequency of functional mutants in a library when an appropriate selection or screening method is employed, might be used. Arkin and Yourvan (1992) Proc. Natl. Acad. Sci. USA 89:7811-7815; Yourvan et al. (1992) Parallel Problem Solving from Nature, Maenner and Manderick, eds., Elsevier Publishing Co., Amsterdam, pp. 401-410; Delgrave et al. (1993) Protein Engineering 6(3): 327-331.

The invention also provides for reduction of SAM or Neuropilin 1 proteins to generate mimetics, e.g. peptide or non-peptide agents, that are able to disrupt binding of SAM or Neuropilin 1 protein to other proteins or molecules with which the native SAM or Neuropilin 1 protein interacts. Thus, the techniques described herein can also be used to map which determinants of SAM or Neuropilin 1 protein participate in the intermolecular interactions involved in, e.g., binding of SAM or Neuropilin 1 protein to other proteins which may function upstream (e.g., activators or repressors of SAM or Neuropilin 1 functional activity) of the SAM or Neuropilin 1 protein or to proteins or nucleic acids which may function downstream of the SAM or Neuropilin 1 protein, and whether such molecules are positively or negatively regulated by the SAM or Neuropilin 1 protein. To illustrate, the critical residues of an SAM or Neuropilin 1 protein, similar to the RGD motif described above, which are involved in molecular recognition of, e.g., SAM or Neuropilin 1 protein or other components upstream or downstream of the SAM or Neuropilin 1 protein can be determined and used to generate SAM or Neuropilin 1 protein-derived peptidomimetics which competitively inhibit binding of the SAM or Neuropilin 1 protein to that moiety. By employing scanning mutagenesis to map the amino acid residues of a SAM or Neuropilin 1 protein that are involved in binding other extracellular proteins, peptidomimetic compounds can be generated which mimic those residues of a native SAM or Neuropilin 1 protein. Such mimetics may then be used to interfere with the normal function of an SAM or Neuropilin 1 protein.

For example, non-hydrolyzable peptide analogs of such residues can be generated using benzodiazepine (see, e.g., Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopepitides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1: 1231), and beta-aminoalcohols (Gordon et al. (1985) Biochem. Biophys. Res. Commun. 126:419; and Dann et al. (1986) Biochem. Biophys. Res. Commun. 134: 71). SAM or Neuropilin 1 proteins may also be chemically modified to create SAM or Neuropilin 1 protein derivatives by forming covalent or aggregate conjugates with other chemical moieties, such as glycosyl groups, lipids, phosphate, acetyl groups and the like. Covalent derivatives of SAM or Neuropilin 1 protein can be prepared by linking the chemical moieties to functional groups on amino acid side chains of the protein or at the N-terminus or at the C-terminus of the polypeptide.

The present invention further pertains to methods of producing the subject SAM or Neuropilin 1 proteins. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant SAM or Neuropilin 1 protein can be isolated from host cells using techniques known in the art for purifying proteins including ion-exchange chromatography, gel filtration chromatography, ultrafiltration, electrophoresis, and immunoaffinity purification with antibodies specific for such protein.

For example, after a SAM or Neuropilin 1 protein has been expressed in a cell, it can be isolated using any immuno-affinity chromatography. More specifically, an anti-SAM or Neuropilin 1 antibody (e.g., produced as described below) can be immobilized on a column chromatography matrix, and the matrix can be used for immuno-affinity chromatography to purify the SAM or Neuropilin 1 protein from cell lysates by standard methods (see, e.g., Ausubel et al., supra). After immuno-affinity chromatography, the SAM or Neuropilin 1 protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, an SAM or Neuropilin 1 protein is expressed as a fusion protein containing an affinity tag (e.g., GST) that facilitates its purification.

Proteins that Associate with SAM or Neuropilin 1 Proteins

The invention also features methods for identifying polypeptides that can associate with SAM or Neuropilin 1 protein. Any method that is suitable for detecting protein-protein interactions can be employed to detect polypeptides that associate with SAM or Neuropilin 1 protein. Examples of such methods include co-immunoprecipitation, crosslinking, and co-purification through gradients or chromatographic columns of cell lysates or proteins obtained from cell lysates and the use of SAM or Neuropilin 1 protein to identify proteins in the lysate that interact with the SAM or Neuropilin 1 protein. For these assays, the SAM or Neuropilin 1 protein can be a full length SAM or Neuropilin 1 protein, a particular domain of SAM or Neuropilin 1 protein, or some other suitable fragment of SAM or Neuropilin 1 protein. Once isolated, such an interacting protein can be identified and cloned and then used, in conjunction with standard techniques, to alter the activity of the protein with which it interacts. For example, at least a portion of the amino acid sequence of a protein that interacts with SAM or Neuropilin 1 protein can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and PCR Protocols: A Guide to Methods and Applications, Innis et al., eds. Academic Press, Inc., NY, 1990).

Additionally, methods can be employed that result directly in the identification of genes that encode proteins that interact with SAM or Neuropilin 1 protein. These methods include, e.g., screening expression libraries, in a manner similar to the well known technique of antibody probing of Igt11 libraries, using labeled SAM or Neuropilin 1 protein or SAM or Neuropilin 1 fusion protein, e.g., SAM or Neuropilin 1 protein or domain fused to a marker such as an enzyme, fluorescent dye, a luminescent protein, or to an IgFc domain.

There are also methods available that can detect protein-protein interaction in vivo. For example, as described herein the two-hybrid system can be used to detect such interactions in vivo. See, e.g., Chien et al., Proc. Natl. Acad. Sci. USA 88:9578, 1991. Briefly, as one example of utilizing such a system, plasmids are constructed that encode two hybrid proteins: one plasmid includes a nucleotide sequence encoding the DNA-binding domain of a transcription activator protein fused to a nucleotide sequence encoding SAM or Neuropilin 1 protein, SAM or Neuropilin 1 protein variant or fragment, or SAM or Neuropilin 1 fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, SAM or Neuropilin 1 protein may be used as the bait. Total genomic or cDNA sequences are fused to the DNA encoding an activation domain. This library and a plasmid encoding a hybrid of bait SAM or Neuropilin 1 protein fused to the DNA-binding domain are co-transformed into a yeast reporter strain, and the resulting transformants are screened for those that express the reporter gene. For example, a bait SAM or Neuropilin 1 gene sequence, such as that encoding SAM or Neuropilin 1 protein or a domain of SAM or Neuropilin 1 protein can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait SAM or Neuropilin 1 protein are to be detected can be made using methods routinely practiced in the art. According to the particular system described herein, e.g., the cDNA fragments can be inserted into a vector such that they are translationally fused to the transcriptional activation domain of GAL4. This library can be co-transformed along with the SAM or Neuropilin 1 or SAM or Neuropilin 1-GAL4 encoding fusion plasmid into a yeast strain which contains a lacZ gene driven by a promoter which contains GAL4 activation sequence. A cDNA encoded protein, fused to GAL4 transcriptional activation domain, that interacts with bait SAM or Neuropilin 1 protein will reconstitute an active GAL4 protein and thereby drive expression of the HIS3 gene. Colonies that express HIS3 can then be purified from these strains and used to produce and isolate bait SAM or Neuropilin 1 protein-interacting proteins using techniques routinely practiced in the art.

Diabetes Mellitus

Diabetes mellitus is characterized by a progressive loss of islet β-cells with concomitant loss of the body's ability to maintain normoglycemia. The current invention provides a method to monitor, detect, and identify diabetes mellitus. An agent capable of both specifically binding SAMs and/or neuropilin 1, as well as detection by an imaging device, can be administered to a patient with diabetes mellitus, and an image can be created by an imaging device. The resulting image can be used to determine the total β-cell mass in the pancreas. From this total cell mass the extent of the disease, if any, can be determined. Images generated at successive time points using the described method can be compared and progression of disease can be monitored. Additionally, the described method can be used to monitor the efficacy of treatments administered for the purpose of increasing, maintaining, or reversing loss of total β-cell mass.

Further, in another aspect of the present invention, it has been determined that SAMs are important in terms of insulin release. Thus, another aspect of the present invention includes targeting these particular molecules for drug therapies useful in the treatment of diabetes mellitus.

Pancreatic Cancer

In pancreatic cancer, as in most cancers, it is thought that metastatic spread is the critical threshold in the process of cancer progression that leads to significant decline in patient survival. Although surgical modalities are the preferred intervention, the potential for occult metastatic spread of the disease often requires the administration of systemic therapies. Some of the patients who receive systemic treatment do so unnecessarily as surgical resection of the primary and local metastatic lesions is curative. Conversely, some patients may not receive any systemic therapy when in fact they harbor occult metastatic or micrometastatic lesions.

Islet cell carcinomas are derived from pancreatic islet β-cells and often express many of the same cell surface proteins as the β-cells from which they arise. The present invention provides a key diagnostic method for the detection of occult metastatic lesions and for the early detection of pancreatic cancers.

The current invention provides a method for locating local and distal metastatic lesions arising from a primary pancreatic cancer expressing SAMs and/or neuropilin 1. The method includes administering to a mammal an agent capable of both specifically binding SAMs and/or neuropilin 1 and detection by an imaging device. The resulting image generated by the method can be analyzed and potentially metastatic lesions expressing SAMs and/or neuropilin 1 can be identified. Additionally, the imaging could be repeated over a period of time to determine the rate of growth of the primary or metastatic lesion, or to assess the efficacy of an intervening modality, including but not limited to surgery, radiation, chemotherapy, pharmaceutical therapy, or otherwise.

Transplantation

Transplantation of pancreatic islet cells is emerging as a new therapy for the treatment of diabetes. The transplantation of pancreatic islet cells allows many patients to become insulin independent; however, some of these patients will later revert back to a insulin dependence. The potential causes of these reversions are not known but the loss of transplanted islet cell mass is believed to be a major factor. The lack of an effective method for imaging these islet cell masses in vivo has hindered research into the causes and potential treatments for these reversions to insulin dependence.

The current invention provides a method for determining the total transplanted β-cell mass. Subsequent to transplantation an agent can be administered that binds selectively to SAMs and/or neuropilin 1, and images taken. The resulting image generated by the method can be analyzed and the total β-cell mass can be assessed. Images generated both pre- and post-transplantation can be compared to determine the increase in total β-cell mass, post implantation. Continued follow up images can be used to assess the stability of transplanted cells.

Conjugated Agents

One non-limiting aspect of the current invention includes administering to a mammal in need thereof a first agent that is conjugated to a second agent, wherein the first agent is capable of specifically binding to SAMs and/or neuropilin 1, and the second agent is a reporter agent capable of detection by an external imaging device. For the purposes of imaging the second agent may be selected from the group comprising radioisotopes, fluorescent tags, paramagnetic ions, enzymes. Several radioisotopes could be used including, but not limited to, iodine 131, yttrium 90, Iodide 124, Zirconium 89, Technicium-99, and Indium 111. Methods of conjugating radioisotopes and paramagnetic ions are well known in the art. Additionally, methods of imaging radioisotopes and paramagnetic ions are also well known in the art. Alternatively, the first and second agents could be administered separately, such that the first agent is allowed to bind to SAMs and/or neuropilin 1, and the second agent is then administered and allowed to bind to the first agent.

Multiple Agents with Binding Capacities

It is further recognized that several layers of agents are possible. For example, in one non-limiting aspect of the present invention, a first agent capable of binding SAMs and/or neuropilin 1 is administered to a mammal followed by second agent capable of binding the first agent which is conjugated to a third agent. In this scenario the third agent consists of a radioisotope, fluorescent tag, paramagnetic ion, or enzyme capable of detection by an imaging device.

Imaging Devices

In any of various methods described herein utilizing imaging devices, any suitable imaging device may be used. Devices currently known in the art include, but are not limited to, devices for nuclear magnetic resonance, magnetic resonance imaging, computer tomography, and positron emission tomography. Other methods for imaging include the use of radioisotopes, paramagnetic ions, labeled antibodies, labeled antibody fragments, labeled polypeptides, labeled nucleic acids, labeled probes, fluorescent imaging methods, and the like. As noted herein, the imaging device or method may detect a first agent bound directly to SAMs and/or neuropilin 1, or may detect a second or third agent bound to the first as described herein. In some instances, more than three agents may be used and layered as described herein.

Methods for Treating Pancreatic Disease

The current invention provides a method for treating disease comprising administering to a mammal in need thereof an agent that selectively binds SAMs and/or neuropilin 1. In accordance with a further aspect of the invention the agent is selected from a group consisting of an antibody, antibody fragment, variable region of an antibody, protein, polypeptide, nucleic acids, probes, oligonucleotides, and ribozymes.

Conjugated First Agents

One non-limiting aspect of the current invention comprises administering to a mammal in need thereof a first agent that is conjugated to a second agent, wherein the first agent is capable of specifically binding to SAMs and/or neuropilin 1. Because anti-SAMs and/or anti-neuropilin 1 antibodies selectively bind cells expressing the SAMs and/or neuropilin 1 (e.g., cells from patients suffering from pancreatic disease), they can be used in methods to target and/or destroy such SAM or neuropilin 1 expressing cells. Thus, the second agent may be, for example, selected from the group consisting of a cytotoxic agent, radioisotope, toxin, agent capable of inducing cellular senescence, an enzyme, or any other agent capable of providing a desired effect when bound to the first agent. For example, to treat synaptic adhesion molecule associated pancreatic disease, anti-synaptic adhesion molecule antibodies can be labeled with a cytotoxic agent (e.g., ricin), or a radioisotope and administered to an animal having the pancreatic disease (e.g., by intratumoral injection). Further, to treat neuropilin 1 associated pancreatic disease, anti-neuropilin 1 antibodies can be labeled with a cytotoxic agent or radioisotope, as described above, and administered to an animal having the pancreatic disease.

The current invention is also well adapted to treatments known in the art as Antibody-directed Enzyme Prodrug Therapy. In this aspect the second conjugated agent consists of an enzyme capable of converting a third agent, a pro-drug, into an biologically active product. The third agent may be selected from a group of agents that, when modified by the enzymatic action of the second agent, generate a product with cytotoxic or cytostatic properties.

Method for Preventing Autoimmune Diabetes and/or Other Autoimmune Diseases

Antibodies, polypeptides, or other agents that bind to, block, or otherwise interfere with SAMs and/or neuropilin 1 may be used to treat patients with autoimmune diabetes, or may be used prophylactically to prevent individuals at risk for autoimmune diabetes from contracting the disorder. Such agents may function in a number of ways by preventing immune attack on insulin-producing islet β-cells. Any suitable agent may be used as described above, including antibodies, antibody fragments, variable regions of antibodies, proteins, polypeptides, nucleic acids, probes, oligonucleotides, protein-methylation compounds, and ribozymes. Any of various SAMs that serves as part of the "immunological synapse" may be targeted in this manner, including SynCam and Thy-1. In addition, neuropilin 1 may be targeted in this aspect of the present invention.

Other Agents

For the purposes of treatment, in many aspects of the present invention, antibodies may be used. Antibodies have properties that make them especially adapted to the current invention. Specifically, they have the ability to recognize almost limitless epitopes, including linear and conformational epitopes comprised of proteins, carbohydrates, glycoproteins, lipoproteins, and/or lipids.

In the case of administration of the antibody to a human, the antibodies may comprise fully humanized antibodies. Antibodies derived from non-human sources generally cannot be administered to humans because the primary, secondary, and tertiary structures of the antibodies, particularly the crystallizable fragments, are subject to interspecies variations. In most instances the human immune system recognizes these variations as foreign. Methods for the production of antibodies are known in the art. Such antibodies include but are not limited to polyclonal, monoclonal, chimeric, single chain, Fab fragments and a Fab expression library. Additionally, the use of peptide mimetrics to target a specific protein is known in the art.

In other aspects, the present invention utilizes proteins capable of binding SAMs and/or neuropilin 1. In one non-limiting aspect of the current invention the proteins capable of binding SAMs and/or neuropilin 1 are purified native ligands of SAMs and/or neuropilin 1. Native ligands of SAMs include, but are not limited to, neuroligin 2, neurexin 1, neurexin 2, SynCam, Thy-1, and neuronal pentraxin. Variants of these native ligands such as fragments, analogs and derivatives of native ligands are also within the scope of the present invention. Such variants include, e.g., a polypeptide encoded by a naturally occurring allelic variant of a native ligand, a polypeptide encoded by an alternative splice form of a native ligand, a polypeptide encoded by a homolog of a native ligand, and polypeptides encoded by a non-naturally occurring variant of a native ligand.

Isolated peptidyl portions of native ligands can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, synaptic adhesion molecule or neuropilin 1 proteins of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can bind synaptic adhesion molecule or neuropilin 1 proteins.

Variants of synaptic adhesion molecule or neuropilin 1 ligands can be generated through various techniques known in the art. For example, ligand variants can be made by mutagenesis, such as by introducing discrete point mutation(s), or by truncation. Mutation can give rise to a ligand variant having substantially the same, or merely a subset of the functional activity of a ligand. Other variants of ligands that can be generated include those that are resistant to proteolytic cleavage, for example, due to mutations that alter protease target sequences. Whether a change in the amino acid sequence of a peptide results in ligand variant having one or more functional activities of a native ligands can be readily determined by testing the variant for a native synaptic adhesion molecule or neuropilin 1 protein's functional activity.

Combinatorial mutagenesis has a potential to generate very large libraries of mutant proteins. To screen a large number of protein mutants, techniques that allow one to avoid the very high proportion of non-functional proteins in a random library and simply enhance the frequency of functional proteins (thus decreasing the complexity required to achieve a useful sampling of sequence space) can be used. For example, recursive ensemble mutagenesis (REM), an algorithm that enhances the frequency of functional mutants in a library when an appropriate selection or screening method is employed, might be used. Arkin and Yourvan (1992) Proc. Natl. Acad. Sci. USA 89:7811-7815; Yourvan et al. (1992) Parallel Problem Solving from Nature, Maenner and Manderick, eds., Elsevier Publishing Co., Amsterdam, pp. 401-410; Delgrave et al. (1993) Protein Engineering 6(3): 327-331.

The invention also provides for reduction of ligands, antibodies to SAMs and/or neuropilin 1, or other proteins capable of specifically binding SAMs and/or neuropilin 1 to generate mimetics, e.g. peptide or non-peptide agents, that are able to bind SAMs or neuropilin 1.

For example, non-hydrolyzable peptide analogs of such residues can be generated using benzodiazepine (see, e.g., Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopepitides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1: 1231), and beta-aminoalcohols (Gordon et al. (1985) Biochem. Biophys. Res. Commun. 126:419; and Dann et al. (1986) Biochem. Biophys. Res. Commun. 134: 71). Ligands may also be chemically modified to create ligand derivatives by forming covalent or aggregate conjugates with other chemical moieties, such as glycosyl groups, lipids, phosphate, acetyl groups and the like. Covalent derivatives of ligands can be prepared by linking the chemical moieties to functional groups on amino acid side chains of the protein or at the N-terminus or at the C-terminus of the polypeptide.

Identification and Separation

The current invention provides a method for identifying and separating mammalian cells expressing SAMs and/or neuropilin 1 from cells not expressing SAMs or neuropilin 1 comprising combining cells with an agent capable of binding SAMs and separating the cells capable of binding the agent from cells incapable of binding the agent. The synaptic adhesion molecule may include neuroligin 1, neuroligin 2, neuroligin 3, neuroligin 4X, neuroligin 4Y, neurexin 1α, neurexin 2α, neurexin 3α, neurexin 1β, neurexin 2β, neurexin 3β, SynCam, Thy-1, and neuronal pentraxin. Further, neuropilin 1 may be utilized. In accordance with a further aspect of the invention the agent is selected from a group consisting of an antibody, antibody fragment, variable region of an antibody, protein, polypeptide, nucleic acids, probes, oligonucleotides, and ribozymes.

In one non-limiting aspect of the present invention, the cells to be separated are obtained from a tissue. Methods for isolating cells from a tissue explant are well known by those skilled in the art.

Separation and Transplantation

Transplantation of islet β-cells from the pancreas is emerging as a potential therapy for the treatment of diabetes mellitus. The transplantation procedure consists of harvesting pancreatic tissue from a donor. The β-cells are then identified and separated from the remaining population of cells. The resulting population of islet β-cells are either transplanted directly into the recipient or are expanded in vitro and then transplanted. Transplantation occurs by injection into the portal vein with the resulting formation of islet masses in the hepatic tissue.

The current technique provides a method for separating β-cells from a mixture of cells comprising adding an agent capable of binding SAMs and/or neuropilin 1 to a mixture of cells and separating the cells capable of binding the agent from those incapable of binding the agent based on the ability of cells to bind the agent. The resulting population of islet β-cells could be used for transplantation into a recipient in need thereof. Additionally, the current invention could be used to separate a population of synaptic adhesion molecule expressing stem cells from a sample of stem cells.

Pancreatic Cells

One non-limiting aspect of the current invention comprises combining pancreatic tissue or cells obtained therefrom with an agent capable of binding SAMs and/or neuropilin 1 and separating the cells binding the agent from the cells not binding the agent. Separating pancreatic cells expressing SAMs and/or neuropilin 1 could be useful for numerous purposes. For example, isolated pancreatic cancer cells expressing SAMs and/or neuropilin 1 could be used in the preparation of a cancer vaccine. It is appreciated that separation could be obtained by a variety of methods.

Affinity for Agent

In one aspect of the invention cells are mixed with an agent that is capable of binding SAMs and/or neuropilin 1 whether it is immobilized on a solid surface or free in solution. The cells that bind the immobilized agent are then separated from the non-binding cells based on the affinity of SAM and/or neuropilin 1 expressing cells for the immobilized agent. The solid phase used in this invention may be any surface commonly used in such methods. For example, the solid phase may be particulate; it may be the surface of beads, e.g., glass or polystyrene beads, or it may be the solid wall surface of any of a variety of containers, e.g., centrifuge tubes, columns, microtiter plate wells, filters, membranes and tubing, among other containers.

In one aspect of the present invention, the agent is immobilized on magnetic or magnetizable particles, such as paramagnetic particles. A sample of cells is added to the particles and separation occurs based on the affinity of the cells expressing SAMs and/or neuropilin 1 to the agent bound to paramagnetic particles. The application of an external magnetic field aids the separation of the paramagnetic particles with the bound cells from the unbound cells. The sample is then washed with a buffer solution and the cells which remain bound to the immobilized agent are retained.

FACS Analysis

In one aspect of the present invention the method of separation is fluorescence-activated cell sorting (FACS). In this embodiment the cell sample would be treated with an agent, preferably an antibody that is conjugated to fluorescent tag. The population would be then be placed into a FACS analyzer and the cells binding the antibody would be separated from the non-binding cells based on intensity of emitted fluorescent radiation.

It is appreciated that several insubstantial substitutions could be made to this embodiment, as this method of cell sorting is readily known in the art. For example, the use of an unconjugated primary antibody capable of binding SAMs and/or neuropilin 1 followed by the addition of a conjugated secondary antibody, derived from a distinct species of animal, would be readily known to one skilled in the art. Additionally, any number of fluorescent tags with varying excitation and emission wavelengths could be used and would be readily known to one skilled in the art.

Identification

The current invention provides a method for identifying mammalian cells expressing SAMs and/or neuropilin 1 comprising combining a sample of cells with an agent capable of binding SAMs and/or neuropilin 1 and identifying the cells, directly or indirectly, that are capable of binding the agent. The synaptic adhesion molecule may be selected from the group consisting of neuroligin 1, neuroligin 2, neuroligin 3, neuroligin 4X, neuroligin 4Y, neurexin 1α, neurexin 2α, neurexin 3α, neurexin 1β, neurexin 2β, neurexin 3β, SynCam, Thy-1, and neuronal pentraxin. Further, neuropilin 1 may be used. In accordance with a further aspect of the invention the agent is selected from a group consisting of an antibody, antibody fragment, variable region of an antibody, protein, polypeptide, nucleic acids, probes, oligonucleotides, and ribozymes.

In one non-limiting aspect of the current invention the first agent is conjugated to a second agent which is capable of generating a signal either directly or indirectly, the signal being perceptible either visually or with the aid of an imaging device. The second agent may be selected from the group consisting of a fluorescent tag, radioisotope, enzyme, or paramagnetic ion.

Pharmaceutical Preparations and Methods of Administration

In addition to administration of the antibodies described above, other identified agents treat, inhibit, control and/or prevent, or at least partially arrest or partially prevent, pancreatic disease and can be administered to a subject at therapeutically effective doses for the inhibition, prevention, prophylaxis or therapy for damage caused by pancreatic disease. The agents of the present invention comprise a therapeutically effective dosage of an antibody, antibody fragment, variable region of an antibodies, proteins, polypeptides, nucleic acids, probes, oligonucleotides, ribozymes, and any combination thereof, and other compounds that bind SAMs and/or neuropilin 1, a term which includes therapeutically, inhibitory, preventive and prophylactically effective doses of the agents of the present invention and is more particularly defined below. Without being bound to any particular theory, applicants surmise that these pharmaceutical agents prevent damage caused by pancreatic diseases when administered to a subject suffering from a related condition by modulating β-cell adhesion, spreading, and migration. The subject is an animal, including, but not limited to, mammals, reptiles and avians, horses, cows, dogs, cats, sheep, pigs, and chickens, and specifically, humans.

Therapeutically Effective Dosage

Toxicity and therapeutic efficacy of such agents can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Agents that exhibit large therapeutic indices are preferred. While agents exhibiting toxic side effects may be used, care should be taken to design a delivery system that targets such agents to the site affected by the disease or disorder in order to minimize potential damage to unaffected cells and reduce side effects.

The data obtained from the cell culture assays and animal studies can be used in formulating a range of dosages for use in humans and other mammals. The dosage of such agents lies preferably within a range of circulating plasma or other bodily fluid concentrations that include the $ED_{50}$ with little or no toxicity. The dosage may vary within this range depending upon the dosage form employed and the route of administration utilized. For any agents of the invention, the therapeutically effective dose can be estimated initially from cell culture assays. A dosage may be formulated in animal models to achieve a circulating plasma concentration range that includes the $IC_{50}$ (the concentration of the test agent that achieves a half-maximal inhibition of symptoms) as determined in cell culture. Such information can be used to more accurately determine useful dosages in humans and other mammals. Agent levels in plasma may be measured, for example, by high performance liquid chromatography.

The amount of an agent that may be combined with pharmaceutically acceptable carriers to produce a single dosage form will vary depending upon the host treated and the particular mode of administration. It will be appreciated by those skilled in the art that the unit content of a agent contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage regime for treating a disease or condition with the agents and/or agent combinations of this invention is selected in accordance with a variety of factors, including the type, age, weight, sex, diet and medical condition of the patient, the route of administration, pharmacological considerations such as activity, efficacy, pharmacokinetic and toxicology profiles of the particular agent employed, whether an agent delivery system is utilized and whether the agent is administered as a pro-drug or part of a drug combination. Thus, the dosage regime actually employed may vary widely from subject to subject.

Formulations and Use

The agents of the present invention may be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. The individual agents may also be administered in combination with one or more additional agents of the present invention and/or together with other biologically active or biologically inert agents ("agent combinations"). Such biologically active or inert agents may be in fluid or mechanical communication with the agent(s) or attached to the agent(s) by ionic, covalent, Van der Waals, hydrophobic, hydrophilic or other physical forces. It is preferred that administration is localized in a subject, but administration may also be systemic.

The agents or agent combinations may be formulated by any conventional manner using one or more pharmaceutically acceptable carriers and/or excipients. Thus, the agents and their pharmaceutically acceptable salts and solvates may be specifically formulated for administration, e.g., by inhalation or insufflation (either through the mouth or the nose) or oral, buccal, parenteral or rectal administration. The agent or agent combinations may take the form of charged, neutral and/or other pharmaceutically acceptable salt forms. Examples of pharmaceutically acceptable carriers include, but are not limited to, those described in Remington's Pharmaceutical Sciences (A. R. Gennaro, Ed.), 20th edition, Williams & Wilkins PA, USA (2000).

The agents may also take the form of solutions, suspensions, emulsions, tablets, pills, capsules, powders, controlled- or sustained-release formulations and the like. Such agents will contain a therapeutically effective amount of the agent, preferably in purified form, together with a suitable amount of carrier so as to provide the form for proper administration to the patient. The formulation should suit the mode of administration.

Parenteral Administration

The agent or agent combination may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The agent may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the agent may be in powder form for constitution with a suitable vehicle, such as sterile pyrogen-free water, before use. For example, a agent suitable for parenteral administration may comprise a sterile isotonic saline solution containing between 0.1 percent and 90 percent weight per volume of the agent or agent combination. By way of example, a solution may contain from about 5 percent to about 20 percent, more preferably from about 5 percent to about 17 percent, more preferably from about 8 to about 14 percent, and still more preferably about 10 percent of the agent. The solution or powder preparation may also include a solubilizing agent and a local anesthetic such as lignocaine to ease pain at the site of the injection. Other methods of parenteral delivery of agents will be known to the skilled artisan and are within the scope of the invention.

Oral Administration

For oral administration, the agent or agent combination may take the form of tablets or capsules prepared by conventional means with pharmaceutically acceptable excipients such as binding agents, fillers, lubricants and disintegrants:

A. Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

B. Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

C. Lubricants

Lubricants include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

D. Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

The tablets or capsules may optionally be coated by methods well known in the art. If binders and/or fillers are used with the agents of the invention, they are typically formulated as about 50 to about 99 weight percent of the agent. Preferably, about 0.5 to about 15 weight percent of disintegrant, preferably about 1 to about 5 weight percent of disintegrant, may be used in the agent. A lubricant may optionally be added, typically in an amount of less than about 1 weight percent of the agent. Techniques and pharmaceutically acceptable additives for making solid oral dosage forms are described in Marshall, Solid Oral Dosage Forms, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the agent. Oral formulations preferably contain 10% to 95% agent. In addition, the agents of the present invention may be formulated for buccal administration in the form of tablets or lozenges formulated in a conventional manner. Other methods of oral delivery of agents will be known to the skilled artisan and are within the scope of the invention.

Controlled-Release Administration

Controlled-release (or sustained-release) preparations may be formulated to extend the activity of the agent or agent combination and reduce dosage frequency. Controlled-release preparations can also be used to effect the time of onset of action or other characteristics, such as blood levels of the agent, and consequently affect the occurrence of side effects.

Controlled-release preparations may be designed to initially release an amount of a agent that produces the desired therapeutic effect, and gradually and continually release other amounts of the agent to maintain the level of therapeutic effect over an extended period of time. In order to maintain a near-constant level of an agent in the body, the agent could be released from the dosage form at a rate that will replace the amount of agent being metabolized and/or excreted from the body. The controlled-release of an agent may be stimulated by various inducers, e.g., change in pH, change in temperature, enzymes, water, or other physiological conditions or molecules.

Controlled-release systems may include, for example, an infusion pump which may be used to administer the agent in a manner similar to that used for delivering insulin or chemotherapy to specific organs or tumors. Typically, using such a system, the agent is administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and blends thereof. In addition, a controlled release system can be placed in proximity of a therapeutic target, thus requiring only a fraction of a systemic dosage.

The agents of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of agents will be known to the skilled artisan and are within the scope of the invention.

Inhalation Administration

The agent or agent combination may also be administered directly to the lung by inhalation. For administration by inhalation, a agent may be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas may be used to deliver an agent directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer an agent to the lung. DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of the compound and a suitable powder base such as lactose or starch for these systems.

Another type of device that may be used to deliver an agent to the lung is a liquid spray device supplied, for example, by Aradigm Corporation. Liquid spray systems use extremely small nozzle holes to aerosolize liquid agent formulations that may then be directly inhaled into the lung. For example, a nebulizer device may be used to deliver a agent to the lung. Nebulizers create aerosols from liquid agent formulations by using, for example, ultrasonic energy to form fine particles that may be readily inhaled. Examples of nebulizers include devices supplied by Sheffield/Systemic Pulmonary Delivery Ltd., Aventis and Batelle Pulmonary Therapeutics.

In another example, an electrohydrodynamic ("EHD") aerosol device may be used to deliver an agent to the lung. EHD aerosol devices use electrical energy to aerosolize liquid agent solutions or suspensions. The electrochemical properties of the agent formulation are important parameters to optimize when delivering this agent to the lung with an EHD aerosol device. Such optimization is routinely performed by one of skill in the art. Other methods of intra-pulmonary delivery of agents will be known to the skilled artisan and are within the scope of the invention.

Liquid agent formulations suitable for use with nebulizers and liquid spray devices and EHD aerosol devices will typically include the agent with a pharmaceutically acceptable carrier. In one exemplary embodiment, the pharmaceutically acceptable carrier is a liquid such as alcohol, water, polyethylene glycol or a perfluorocarbon. Optionally, another material may be added to alter the aerosol properties of the solution or suspension of the agent. For example, this material may be a liquid such as an alcohol, glycol, polyglycol or a fatty acid. Other methods of formulating liquid agent solutions or suspensions suitable for use in aerosol devices are known to those of skill in the art.

Depot Administration

The agent or agent combination may also be formulated as a depot preparation. Such long-acting formulations may be administered by implantation (e.g., subcutaneously or intramuscularly) or by intramuscular injection. Accordingly, the agents may be formulated with suitable polymeric or hydrophobic materials such as an emulsion in an acceptable oil or ion exchange resins, or as sparingly soluble derivatives such as a sparingly soluble salt. Other methods of depot delivery of agent s will be known to the skilled artisan and are within the scope of the invention.

Topical Administration

For topical application, the agent or agent combination may be combined with a carrier so that an effective dosage is delivered, based on the desired activity ranging from an effective dosage, for example, of 1.0 μM to 1.0 mM. In one embodiment, a topical agent is applied to the skin. The carrier may be in the form of, for example, and not by way of limitation, an ointment, cream, gel, paste, foam, aerosol, suppository, pad or gelled stick.

A topical formulation may also consist of a therapeutically effective amount of the agent in an ophthalmologically acceptable excipient such as buffered saline, mineral oil, vegetable oils such as corn or arachis oil, petroleum jelly, Miglyol 182, alcohol solutions, or liposomes or liposome-like products. Any of these agents may also include preservatives, antioxidants, antibiotics, immunosuppressants, and other biologically or pharmaceutically effective agents which do not exert a detrimental effect on the agent. Other methods of topical delivery of agents will be known to the skilled artisan and are within the scope of the invention.

Suppository Administration

The agent or agent combination may also be formulated in rectal formulations such as suppositories or retention enemas containing conventional suppository bases such as cocoa butter or other glycerides and binders and carriers such as triglycerides, microcrystalline cellulose, gum tragacanth or gelatin. Suppositories may contain the agent in the range of 0.5% to 10% by weight. Other methods of suppository delivery of agents will be known to the skilled artisan and are within the scope of the invention.

Other Systems of Administration

Various other delivery systems are known in the art and can be used to administer the agents of the invention. Moreover, these and other delivery systems may be combined and/or modified to optimize the administration of the agents of the present invention. Exemplary formulations using the agents of the present invention are described below (the agents of the present invention are indicated as the active ingredient, but those of skill in the art will recognize that pro-drugs and agent combinations are also meant to be encompassed by this term).

Biological Methods

Methods involving conventional molecular biology techniques are generally known in the art and are described in detail in methodology treatises such as MOLECULAR CLONING: A LABORATORY MANUAL, 2nd ed., vol. 1-3, ed. Sambrook et al., Cold Spring Harbor Laboratory Press, Cold Spring Harbor, N.Y., 1989; and CURRENT PROTOCOLS IN MOLECULAR BIOLOGY, ed. Ausubel et al., Greene Publishing and Wiley-Interscience, New York, 1992 (with periodic updates). Various techniques using polymerase chain reaction (PCR) are described, e.g., in Innis et al., PCR PROTOCOLS: A GUIDE TO METHODS AND APPLICATIONS, Academic Press: San Diego, 1990. PCR-primer pairs can be derived from known sequences by known techniques such as using computer programs intended for that purpose. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Each reference is incorporated herein by reference in its entirety.

OTHER EMBODIMENTS

The detailed description set forth above is provided to aid those skilled in the art in practicing the present invention. The invention described and claimed herein, however, is not to be limited in scope by the specific embodiments herein disclosed because these embodiments are intended as illustration of several aspects of the invention. Any equivalent embodiments are intended to be within the scope of the present invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications, and other references cited in this application are incorporated herein by reference in their entirety for all purpose to the same extent as if each individual publication, patent, patent application, or other reference was specifically and individually indicated to be incorporated by reference in its entirety for all purposes.

What is claimed is:

1. A method for detecting a pancreatic β-islet cells expressing a synaptic adhesion molecule, the method comprising:

contacting the pancreatic β-islet cells with an antibody or fragment thereof that binds to the synaptic adhesion molecule; and detecting the antibody or fragment thereof, wherein the synaptic adhesion molecule is a human synaptic adhesion molecule selected from the group consisting of Neuroligin 1, Neuroligin 2, Neurexin 1α, Neurexin 1β, and Syncam.

2. A method according to claim 1, wherein the pancreatic β-islet cells are in a human.

3. A method according to claim 1, wherein the antibody or fragment thereof binds to a human synaptic adhesion molecule having a sequence encoded by one of SEQ ID NOs: 1, 2, 3, 7, 8 or 14.

4. A method according to claim 1, wherein the antibody is a polyclonal, monoclonal, chimeric, or single chain antibody.

5. A method according to claim 4, wherein the antibody is a monoclonal antibody.

6. A method according to claim 5, wherein the monoclonal antibody is a humanized or fully human monoclonal antibody.

7. A method according to claim 1 wherein the antibody fragment comprises an Fab fragment.

8. A method according to claim 1, wherein the antibody or fragment thereof is conjugated to a fluorescent tag, a radioisotope, an enzyme, or a paramagnetic ion and detecting comprises detecting the conjugated antibody or fragment thereof.

9. A method according to claim 8, wherein the method comprises imaging the pancreatic β-islet cells and detecting comprises imaging the conjugated antibody or fragment thereof.

10. A method according to claim 9, wherein the method further comprises determining total pancreatic β-cell mass.

11. A method according to claim 10, wherein the method further comprises detecting diabetes mellitus if present in a human or monitoring the status of diabetes mellitus in a human.

12. A method according to claim 10, wherein the method further comprises detecting a pancreatic β-islet cell tumor if present in a human.

13. A method according to claim 12, wherein the pancreatic β-islet cell tumor is pancreatic cancer.

14. A method of detecting presence or extent of Type I diabetes mellitus in a patient, the method comprising:

administering to the patient, an antibody or fragment thereof that binds to a synaptic adhesion molecule of pancreatic islet β-cells, wherein the antibody or fragment is conjugated to a radioisotope, a fluorescent tag, a paramagnetic ion or an enzyme capable of detection by an imaging device;

detecting binding of the antibody or fragment thereof to the pancreatic islet β-cells by generating an image with the imaging device; and analyzing the image to measure total pancreatic islet β-cell mass and determine, whether there is a loss of pancreatic islet β-cells as an indication of the presence or extent of Type I diabetes mellitus in the patient, wherein the synaptic adhesion molecule is a human synaptic adhesion molecule selected from the group consisting of Neuroligin 1, Neuroligin 2, Neurexin 1α, Neurexin 1β, and Syncam.

15. A method according to claim 14, wherein the antibody or fragment thereof binds to a human synaptic adhesion molecule having a sequence encoded by one of SEQ ID NOs: 1, 2, 3, 7, 8 or 14.

16. A method of detecting pancreatic islet β-cell cancer in a patient, the method comprising:

administering to the patient, an antibody or fragment thereof that binds to a synaptic adhesion molecule of pancreatic islet β-cells, wherein the antibody or fragment is conjugated to a radioisotope, a fluorescent tag, a paramagnetic ion or an enzyme capable of detection by an imaging device;

detecting binding of the antibody or fragment thereof to the pancreatic islet β-cells by generating an image with the imaging device; and analyzing the image to identify pancreatic islet β-cell cancer if present in the patient, wherein the synaptic adhesion molecule is a human synaptic adhesion molecule selected from the group consisting of Neuroligin 1, Neuroligin 2, Neurexin 1α, Neurexin 1β, and Syncam.

17. A method according to claim 16, wherein the antibody or fragment thereof binds to a human synaptic adhesion molecule having a sequence encoded by one of SEQ ID NOs: 1, 2, 3, 7, 8 or 14.

* * * * *

SEQUENCE LISTING

```
<160> NUMBER OF SEQ ID NOS: 18

<210> SEQ ID NO 1
<211> LENGTH: 4918
<212> TYPE: DNA
<213> ORGANISM: Homo sapiens
```

<400> SEQUENCE: 1

```
ccaccgactc ctgcccgcct caacacaatg ccttacctgt gaagcttgag gccactcaag     60
ttccaaattt gtgacaaatc ccccagggct cactggagtg gcagatatag acctgcagct    120
aactggattt gatttataag agagaaatct gcagtcaatg cccactcttg ccacactgct    180
aatatggaaa acagaatgtt caataggata tggtctgata aatagtgatg attgaagatg    240
ctgctccaat acatgtgaaa tcaatgggag atatctgctg tctgaagatc tttcagagct    300
tttctcgaca agctcccctg taagaaatcg gaggtatatt ctaccattat acagtctttc    360
tcaagtggat ataaatacgt ttgcctcact gtaaccagac aactagacaa ctaatgtggg    420
accatggcac tgcccagatg cacgtggcca aattatgttt ggagagcagt gatggcatgc    480
ttggtacacc ggggattggg tgccccattg actctctgta tgttgggatg tttgcttcag    540
gctggccatg tgctatcaca aaaattggat gatgtggacc cactggtggc taccaacttt    600
ggaaagataa gagggattaa gaaggaactc aataatgaaa ttttggggcc tgttattcaa    660
tttcttgggg ttccatatgc agccccacca acaggggaac gtcgttttca gcctccagaa    720
ccaccatctc cctggtcaga tatcagaaat gccactcaat ttgctcctgt gtgtccccag    780
aatatcattg atggcagatt gccagaagtc atgcttcctg tgtggtttac taataacttg    840
gatgtggttt catcatatgt gcaagaccag agcgaagact gcctatattt aaatatatat    900
gtcccgactg aggatgatat tcgggacagt gggggtccca aaccagtgat ggtgtatatc    960
catggtggct catatatgga aggtactgga aatttatatg atggaagtgt cttggcaagt   1020
tatggcaatg tgatcgtcat cacagtcaac tatcgacttg gagtactcgg tttcttgagt   1080
acaggcgatc aggctgcaaa ggggaactat ggactccttg atctcataca agctttaaga   1140
tggactagtg aaaacattgg attctttggt ggtgacccct taagaatcac tgtttttgga   1200
tctggtgctg gggttcatg tgtcaacctg ctgactttat cccattattc tgaaggtaac   1260
cgttggagca attcaaccaa aggacttttt caacgagcaa tagctcaaag tggaacagcc   1320
ctttccagct gggctgttag ttttcaacct gcaaaatatg ctagaatgtt ggccacaaaa   1380
gttggttgca atgtttcaga tacagtagag ttagtggaat gcctacagaa gaagccttac   1440
aaagaacttg ttgaccaaga tattcaacca gctcgatacc acatagcctt tggacctgtg   1500
attgatggtg atgtaatacc agacgacccc cagatattga tggagcaagg agagtttctc   1560
aactatgata taatgttagg agtgaaccaa ggggaagggt taaaatttgt tgaaaatata   1620
gtagatagcg atgatggtat atcagctagt gattttgact ttgctgtttc aaattttgtt   1680
gataatttat atggatatcc tgaaggcaaa gatgttttga gagaaaccat taagttcatg   1740
tatactgact gggctgaccg tcataaccct gaaaccagaa gaaagacatt actggctttg   1800
tttacggacc atcagtgggt ggcaccagct gtagccacag cggatcttca ctcaaacttt   1860
ggttcaccta cgtacttcta tgccttttac catcattgcc aaacagatca ggttccagct   1920
tgggctgatg cagcccacgg agacgaggtt ccctatgtac tgggaatccc catgattggc   1980
cctacagagt tatttccttg caatttctcc aaaaatgatg tgatgctgag tgcagttgta   2040
atgacatact ggacaaattt tgctaaaact ggtgacccaa atcaaccagt ccctcaagac   2100
acgaaattca ttcataccaa acccaaccgt tttgaagaag tagcatggac cagatattcc   2160
cagaaagacc aactttatct ccatattgga ttaaaaccaa gagttaaaga acattacaga   2220
gccaataagg tgaacctctg gttggagttg gtacctcatc tgcataatct caatgacatt   2280
tctcagtata cctctacaac aactaaagtg ccatcaactg acatcacttt cagacctacg   2340
```

```
agaaaaaatt ctgtacctgt cacgtcagcc tttcccactg ccaagcagga tgatcccaaa   2400
caacaaccaa gtccattttc agtggatcaa agggactact caacagagct gagtgtcact   2460
attgcagttg gagcatcact gctgtttctg aacatcttgg cctttgcagc cctgtactac   2520
aaaaaggata agaggagaca tgatgttcac aggagatgca gccctcagcg cactactacc   2580
aatgatctaa cccatgcaca agaagaggaa atcatgtccc tccaaatgaa gcacactgat   2640
ttggatcatg aatgtgagtc cattcatcca catgaggtgg ttcttcggac cgcctgtccc   2700
ccagattaca cactagctat gaggaggtca cctgatgatg ttcccttaat gacacccaac   2760
accattacaa tgattcccaa cactatacca gggattcagc ccttacacac attcaataca   2820
tttactggag gacagaacaa tactctgccc catccccatc cccacccccca ttcacattca   2880
acaaccaggg tatagccaga taagagaaac aaactatttt ttttgatgga ttgcagtaaa   2940
cgatcactga agattccttg gctttcaacc tacaagactt actatttaaa taaggaggaa   3000
tattatgtga atatacatat caagaacttt gggggttttg aaaaaaatga attgtatata   3060
tacaaatcaa ctttaaaaac aaatttcaat tgcttgaagc aattgttctg aatgatactt   3120
tttcattcac attcaagaat taattttttg aagatttaag ttacataatg gaattaggca   3180
tgtggaacac caaacaggaa agaactatgt ctgaaatata aaaaataaaa ataaaaaaac   3240
aactatgaat atgcacaagg gacacaccag tggaatgtca gataattttc accagttttt   3300
atttggagcc gttttattgt gtagaccata tttacatatt tggataagta cacaaagcgt   3360
caatgctgtt aatggcctta gcaaaggctc atgctgaaat ttgccagtaa aacaaagaag   3420
tttaaagact ggcaggtaca ccattatcac ataagtgctg tcagtataaa gttgtgggga   3480
taaaggaaac tggatatttt tagcacgatg tgcatgataa tttatatgct tggtggctgt   3540
gctgctgatt aagccgtaat taaaattctt ctcatcccat tggagttttt aatagaagct   3600
tcctccatca attggcagaa cctaaagaag attttaaggg gcaaaagtaa ttacaataaa   3660
ataattcaca gtagtttcaa tatagaagga attagctatt aaaggtattt gaagaaacta   3720
taggtatagt ggtgaatact cgctgatatg aatcccagaa aaaaatttcc tgtttttaat   3780
gttcttttca atcccatcta gataatttat agaaatataa ccctaattgg acatgtggta   3840
caggatctat aagttgctgt gtttttttgt tactctgtat tttgttcctt ttggtaaggt   3900
gaagtgtgtc caaagagtta cttgcaacag tctttcatga tatgaggatg cccccgtatt   3960
accactctga ttatagttct gagttctttg atttactcat gctgcatgac aaaatgttta   4020
ctaataacaa ttcattataa agttatatcc ctctttacat cacttatctt tctcactgag   4080
gttcattcac tggaatttac tcacgcaatc tcagtagagt acaacgtaga tacagaacct   4140
aggagagtca acatctggag gattttagtc tttcttacac atatgtgtga ttttaaacga   4200
atattctcag accacaggaa actcttcatc cccctgttgt ttaccagtaa cagtatatca   4260
cagacctttc caaatgtttg tatatgtaat cagatgtaca tttatattga aaaacaaatg   4320
agatggactt aaagagcaca tcctgataaa tactttctct ctcacctgta ctatatttct   4380
attagactaa agttatgtga ttttttttt acatttttc agatgactag caattttgat   4440
agtttataag ataatgcaaa gaactttctc tgacaaacta actgcagtaa cagaaacctt   4500
tcttttcagt tactcttttt caagaatgaa agattattat acaaaaaatt gtatactact   4560
tgatggaacc aactttgtac atcttggcca tgtcactggt cattgtgtga aataaagata   4620
atctggataa tgactattag tccaatgcta agaaacatga tctttgctca ttaaagagct   4680
aaaatgttta ttgctgtttt gtctttcttt tttctaaaaa aagaaaaaaa agaaaaaaag   4740
```

```
gaaaagaaga acaaagaaac atgactgtct caaagagtaa tttttctaga ttagaccagt   4800

caggtttttg aagacatata ggtaacttcc acagaaaaca caaacatgta tttaaaggca   4860

agtctcatct aagatgaaac tcataaaaat tatttaatgt ttgttatgaa tttaaaag     4918


<210> SEQ ID NO 2
<211> LENGTH: 4642
<212> TYPE: DNA
<213> ORGANISM: Homo sapiens

<400> SEQUENCE: 2

tccctctccc cccttctct ctctctccga gggggggggg tcccagggag ggaggggggg     60

tcccccgatc agcatgtggc tcctggcgct gtgtctggtg gggctggcgg gggctcaacg    120

cgggggaggg ggtcccggcg gcggcgcccc gggcggcccc ggcctgggcc tcggcagcct    180

cggcgaggag cgcttcccgg tggtgaacac ggcctacggg cgagtgcgcg gtgtgcggcg    240

cgagctcaac aacgagatcc tgggccccgt cgtgcagttc ttgggcgtgc cctacgccac    300

gccgcccctg ggcgcccgcc gcttccagcc gcctgaggcg cccgcctcgt ggcccggcgt    360

gcgcaacgcc accaccctgc cgcccgcctg cccgcagaac ctgcacgggg cgctgcccgc    420

catcatgctg cctgtgtggt tcaccgacaa cttggaggcg gccgccacct acgtgcagaa    480

ccagagcgag gactgcctgt acctcaacct ctacgtgccc accgaggacg gtccgctcac    540

aaaaaaacgt gacgaggcga cgctcaatcc gccagacaca gatatccgtg accctgggaa    600

gaagcctgtg atgctgtttc tccatggcgg ctcctacatg gaggggaccg gaaacatgtt    660

cgatggctca gtcctggctg cctatggcaa cgtcattgta gccacgctca actaccgtct    720

tggggtgctc ggttttctca gcaccgggga ccaggctgca aaaggcaact atgggctcct    780

ggaccagatc caggccctgc gctggctcag tgaaaacatc gcccactttg gggcgacccc    840

cgagcgtatc accatctttg gttccggggc aggggcctcc tgcgtcaacc ttctgatcct    900

ctcccaccat tcagaagggc tgttccagaa ggccatcgcc cagagtggca ccgccatttc    960

cagctggtct gtcaactacc agccgctcaa gtacacgcgg ctgctggcag ccaaggtggg   1020

ctgtgaccga gaggacagcg ctgaagctgt ggagtgtctg cgccggaagc cctcccggga   1080

gctggtggac caggacgtgc agcctgcccg ctaccacatc gcctttgggc ccgtggtgga   1140

tggcgacgtg gtccccgatg accctgagat cctcatgcag cagggagaat tcctcaacta   1200

cgacatgctc atcggcgtca accagggaga gggcctcaag ttcgtggagg actctgcaga   1260

gagcgaggac ggtgtgtctg ccagcgcctt tgacttcact gtctccaact ttgtggacaa   1320

cctgtatggc tacccggaag gcaaggatgt gcttcgggag accatcaagt ttatgtacac   1380

agactgggcc gaccgggaca atggcgaaat gcgccgcaaa accctgctgg cgctctttac   1440

tgaccaccaa tgggtggcac cagctgtggc cactgccaag ctgcacgccg actaccagtc   1500

tcccgtctac ttttacacct tctaccacca ctgccaggcg gagggccggc ctgagtgggc   1560

agatgcggcg cacggggatg aactgcccta tgtctttggc gtgcccatgg tgggtgccac   1620

cgacctcttc ccctgtaact tctccaagaa tgacgtcatg ctcagtgccg tggtcatgac   1680

ctactggacc aacttcgcca agactgggga ccccaaccag ccggtgccgc aggataccaa   1740

gttcatccac accaagccca atcgcttcga ggaggtggtg tggagcaaat tcaacagcaa   1800

ggagaagcag tatctgcaca taggcctgaa gccacgcgtg cgtgacaact accgcgccaa   1860

caaggtggcc ttctggctgg agctcgtgcc ccacctgcac aacctgcaca cggagctctt   1920

caccaccacc acgcgcctgc ctccctacgc cacgcgctgg ccgcctcgtc cccccgctgg   1980
```

```
cgccccgggc acacgccggc ccccgccgcc tgccaccctg cctcccgagc ccgagcccga   2040
gcccggccca agggcctatg accgcttccc cggggactca cgggactact ccacggagct   2100
gagcgtcacc gtggccgtgg gtgcctccct cctcttcctc aacatcctgg cctttgctgc   2160
cctctactac aagcgggacc ggcggcagga gctgcggtgc aggcggctta gcccacctgg   2220
cggctcaggc tctggcgtgc ctggtggggg ccccctgctc cccgccgcgg gccgtgagct   2280
gccaccagag gaggagctgg tgtcactgca gctgaagcgg ggtggtggcg tcggggcgga   2340
ccctgccgag gctctgcgcc ctgcctgccc gcccgactac accctggccc tgcgccgggc   2400
accggacgat gtgcctctct tggcccccgg ggccctgacc ctgctgccca gtggcctggg   2460
gccaccgcca cccccaccgc ccccctccct tcatcccttc gggcccttcc ccccgccccc   2520
tcccaccgcc accagccaca acaacacgct accccacccc cactccacca ctcgggtata   2580
gggggtgggt ggggaggccc tcctccccgg ccctccctgg cccggccact ccgaaggcag   2640
ggaggaggac ttggcaactg gcttttctcc tgtggagtcg tcacacgcca tccagcagcg   2700
ctaaggtgga catgggattc ctccctgcga tgcgtgtctt tcccacgcag agaagcccag   2760
tctcttctct ggatctgggc ctttgaacaa ctggggggcg ttttctcccc cccattggga   2820
caccagtctt cggtgtgtgg aatgtggtat tttcccgcgt ggaggtgtgc tttctcacaa   2880
cggggtgtgt tttcccatgt gcagggtgag gttttttttt gccaccctgg acacatgttg   2940
gccccctcaa agaatttctg tggggatttg taccccagaa tcctgttccc ccatcccttc   3000
tcccacctcc tcccctctcc ctccccctgg agaccctgga agtggtgtgt tcacatacag   3060
tgacccttgg ccaccagacc acagaggatg gagcctggga agcagcgagg aaatcacagc   3120
cccctcgccc ctgcctccct tgcccctacc ccggcgaagc atgttccccc cgacgccccc   3180
cttggcacaa gtcagatgaa gcacgttctg ccggggaggc cctcaccttc cagagaggac   3240
agacacagat ttcctgctgg gggagggagg agtccacgca tcctgatgct gcctggaagc   3300
ttattttccc gtggccagga cgcatttctc tgagtggaaa caggttcttg catgtggatg   3360
tgtgtttccc caggcagacg gcccctctct tcccagcact tccctgcctc cccccaggcct  3420
caggcccagc acccagttcc tcctcacatg gcaggtgagc acagacttct agttggcagg   3480
agctgaggag ggtgaacaaa ccccgaggga ggcccggccc ttgctcccga gttgggggga   3540
gggggtgtgg caacgtgccc cccgcagagg ccacgcatgt ttgaccaaag ccctcattgt   3600
ggtccgagga cagccttttc cccaggcctc agagcattgc tcatccgtgc caaactgggt   3660
aggtggattt gagcggaaag actcccaaaa tgtgccaaga atttcccagt cccaggcagg   3720
gcaggggaaa ctaagggcaa gcaggataca gggcgaggga tgtggcaggt gagggggctc   3780
ccgcctgtgc cccttctcct caccatgtct cccccaccct gcctcagttc tccgttcccc   3840
ttcatctccg tccccctctt tgaagctgtc cccatctcag tgtcagacca gccttctcct   3900
cagctgacca ccctcctctg acccacgccc cctccttgtc tgaaagaaag gagccttgaa   3960
tggtggaggg aggcagtggg gagaaaggtc tcaccggaca ggttgggaga atgaggtcag   4020
cggtgctggg gaacagatgg agggggcagt ggggacaggg cttgggcaga caccagcagg   4080
aataatttga aatgtgtgag gtgactcccc ggagggcctt gggcttgggc atttgggaaa   4140
agaatgatgt ctggaagggc ttaagggaca cagtggacga ggggagagtc ctcatctgct   4200
ggcattttgt ggggtgttag tgccaaactt gaataggggc tggggtgctg tcttccactg   4260
acacccaaat ccagaatccc tggtcttgag tccccagaac tttgcctctt gactgtccct   4320
tctcttccta cctccatcca tggaaaatta gttattttct gatcctttcc cctgcctggt   4380
```

```
ctagctcctc tccaaacagc catgccctcc aaatgctaga gacctgggcc ctgaaccctg   4440

tagacagatg ccctcagaat tggggcatgg gaggggggct gggggacccc atgattcagc   4500

cacggactcc aatgcccagc tcctctcccc aaaacaatcc cgacaatccc ttatccctac   4560

cccaaccctt tgcggctctg tacacatttt taaacctggc aaaagatgaa gagaatattg   4620

taaatataaa agtttaactg tt                                            4642
```

<210> SEQ ID NO 3
<211> LENGTH: 2793
<212> TYPE: DNA
<213> ORGANISM: Homo sapiens

<400> SEQUENCE: 3

```
tccctctccc ccccttctct ctctctccga gggggggggg tcccagggag ggaggggggg     60

tcccccgatc agcatgtggc tcctggcgct gtgtctggtg ggctggcgg gggctcaacg    120

cgggggaggg ggtcccggcg gcggcgcccc gggcggcccc ggcctgggcc tcggcagcct    180

cggcgaggag cgcttcccgg tggtgaacac ggcctacggg cgagtgcgcg gtgtgcggcg    240

cgagctcaac aacgagatcc tgggccccgt cgtgcagttc ttgggcgtgc cctacgccac    300

gccgcccctg ggcgcccgcc gcttccagcc gcctgaggcg cccgcctcgt ggcccggcgt    360

gcgcaacgcc accaccctgc cgcccgcctg cccgcagaac ctgcacgggg cgctgcccgc    420

catcatgctg cctgtgtggt tcaccgacaa cttggaggcg gccgccacct acgtgcagaa    480

ccagagcgag gactgcctgt acctcaacct ttacgtgccc accgaggacg gtccgctcac    540

aaaaaaacgt gacgaggcga cgctcaatcc gccagacaca gatatccgtg accctgggaa    600

gaagcctgtg atgctgtttc tccatggcgg ctcctacatg gaggggaccg gaaacatgtt    660

cgatggctca gtcctggctg cctatggcaa cgtcattgta gccacgctca actaccgtct    720

tggggtgctc ggttttctca gcaccgggga ccaggctgca aaaggcaact atgggctcct    780

ggaccagatc caggccctgc gctggctcag tgaaaacatc gcccactttg gggcgacccc    840

cgagcgtatc accatctttg gttccggggc aggggcctcc tgcgtcaacc ttctgatcct    900

ctcccaccat tcagaagggc tgttccagaa ggccatcgcc cagagtggca ccgccatttc    960

cagctggtct gtcaactacc agccgctcaa gtacacgcgg ctgctggcag ccaaggtggg   1020

ctgtgaccga gaggacagtg ctgaagctgt ggagtgtctg cgccggaagc cctcccggga   1080

gctggtggac caggacgtgc agcctgcccg ctaccacatc gcctttgggc ccgtggtgga   1140

tggcgacgtg gtccccgatg accctgagat cctcatgcag cagggagaat tcctcaacta   1200

cgacatgctc atcggcgtca accagggaga gggcctcaag ttcgtggagg actctgcaga   1260

gagcgaggac ggtgtgtctg ccagcgcctt tgacttcact gtctccaact ttgtggacaa   1320

cctgtatggc tacccggaag gcaaggatgt gcttcgggag accatcaagt ttatgtacac   1380

agactgggcc gaccgggaca atggcgaaat gcgccgcaaa accctgctgg cgctctttac   1440

tgaccaccaa tgggtggcac cagctgtggc cactgccaag ctgcacgccg actaccagtc   1500

tcccgtctac ttttacacct tctaccacca ctgccaggcg gagggccggc ctgagtgggc   1560

agatgcggcg cacggggatg aactgcccta tgtctttggc gtgcccatgg tgggtgccac   1620

cgacctcttc ccctgtaact tctccaagaa tgacgtcatg ctcagtgccg tggtcatgac   1680

ctactggacc aacttcgcca agactgggga ccccaaccag ccggtgccgc aggataccaa   1740

gttcatccac accaagccca atcgcttcga ggaggtggtg tggagcaaat tcaacagcaa   1800

ggagaagcag tatctgcaca taggcctgaa gccacgcgtg cgtgacaact accgcgccaa   1860
```

```
caaggtggcc ttctggctgg agctcgtgcc ccacctgcac aacctgcaca cggagctctt   1920
caccaccacc acgcgcctgc ctccctacgc cacgcgctgg ccgcctcgtc cccccgctgg   1980
cgccccgggc acacgccggc ccccgccgcc tgccaccctg cctcccgagc ccgagcccga   2040
gcccggccca agggcctatg accgcttccc cggggactca cgggactact ccacggagct   2100
gagcgtcacc gtggccgtgg gtgcctccct cctcttcctc aacatcctgg cctttgctgc   2160
cctctactac aagcgggacc ggcggcagga gctgcggtgc aggcggctta gcccacctgg   2220
cggctcaggc tctggcgtgc ctggtggggg ccccctgctc cccgccgcgg gccgtgagct   2280
gccaccagag gaggagctgg tgtcactgca gctgaagcgg ggtggtggcg tcggggcgga   2340
ccctgccgag gctctgcgcc ctgcctgccc gcccgactac accctggccc tgcgccgggc   2400
accggacgat gtgcctctct tggcccccgg ggccctgacc ctgctgccca gtggcctggg   2460
gccaccgcca cccccaccgc ccccctccct tcatcccttc gggcccttcc ccccgccccc   2520
tcccaccgcc accagccaca acaacacgct accccacccc cactccacca ctcgggtata   2580
gggggtgggt ggggaggccc tcctccccgg ccctccctgg cccggccact ccgaaggcag   2640
ggaggaggac ttggcaactg gcttttctcc tgtggagtcg tcacacgcca tccagcagcg   2700
ctaaggtgga catgggattc ctccctgcga tgcgtgtctt tcccacgcag agaagcccag   2760
tctcttctct ggatctgggc ctttgaacaa ctg                                2793
```

<210> SEQ ID NO 4
<211> LENGTH: 3905
<212> TYPE: DNA
<213> ORGANISM: Homo sapiens

<400> SEQUENCE: 4

```
gccggagagc tgatctcggg gattcgggtg cggagccctt ggcctggagg cgatatgggt     60
ggtccgtggc ccggttcagt cgcttgcagc agcccgggga acaggcctgt ctggccctga    120
gggagtcccc tttctgaagc tgtggtgctt ggacgacctg ctctctacat tgctgggcac    180
ctgtaggtgt ccctcgagag ctcagttttg aggttcaagt cagtgtggcc atgaaggggc    240
tgcctattgg gctgatgctg tgaccctgga gtctgcctct cctgccagtc cccctgcccg    300
gaacatgtgg ctgcggcttg gcccgccctc gctgtccctg agccccaagc ccacggttgg    360
caggagcctg tgcctcaccc tgtggttcct cagtttggcg ctgagggcca gtacccaggc    420
cccagcaccc acagtcaaca ctcactttgg gaagctaagg ggtgcccgag taccactgcc    480
cagtgagatc ctggggcctg tggaccaata cctgggggtg ccctacgcag ctcccccgat    540
cggcgagaaa cgtttcctgc cccctgaacc acccccatcc tggtcgggca tccggaacgc    600
cacacacttt cccccagtgt gcccccagaa catccacaca gctgtgcccg aagtcatgct    660
gccggtctgg ttcactgcca acttggatat cgtcgctact tacatccagg agcccaacga    720
agactgtctc tacctgaacg tctatgtgcc gacggaggat ggatccggcg ctaagaaaca    780
gggcgaggac ttagcggata atgacgggga tgaagatgaa gacatccggg acagtggtgc    840
taaacccgtc atggtctaca tccacggagg ctcttacatg gaagggacag gcaacatgat    900
tgatggcagc atcctcgcca gttatggcaa tgtcatcgtc atcaccctca actatcgggt    960
tggagtgcta ggtttcctga gtactggaga tcaggctgcc aagggcaact atgggctcct   1020
tgaccagatc caggccctcc gctgggtgag cgagaatatt gccttcttcg ggggagaccc   1080
ccgccggatc actgtctttg gctcgggcat tggtgcatcc tgcgtcagcc tcctcacgtt   1140
gtcacatcac tcagagggac ttttccagag agccatcatc caaagtggct ctgctctgtc   1200
```

```
cagctgggct gtgaactacc aaccagtgaa gtacaccagc ctgctggcag acaaagtggg   1260
ctgtaatgtg ctggacaccg tggatatggt ggactgtctt cggcaaaaga gtgccaagga   1320
gctggtagag caggacatcc agccagcccg ctaccacgtg gcctttggcc ctgtgattga   1380
tggtgatgtc attcctgatg accctgagat cctcatggag cagggcgagt tcctcaacta   1440
tgacatcatg ctaggtgtca accagggcga gggtctcaag tttgtggaag ggtggtgga    1500
ccctgaggat ggtgtctctg gcactgactt tgactattcc gtctccaatt ttgtggacaa   1560
tctgtatggc tatcctgagg gtaaggacac cctgcgagag accatcaagt tcatgtatac   1620
agactgggca gaccgtgaca accctgagac ccgccgtaaa acactggtgg cactcttcac   1680
tgaccaccag tgggtggagc cctcagtggt gacagccgat ctgcatgccc gctacggctc   1740
gcctacctac ttctacgcct tctatcatca ctgccagagc ctcatgaagc ctgcttggtc   1800
agatgcagct catggggatg aagtacccta tgtttttggg gttcctatgg taggccccac   1860
tgaccttttc ccctgcaact tctccaagaa tgatgttatg ctcagtgctg tcgtcatgac   1920
ctattggacc aactttgcca agactgggga tcccaacaag ccggtccccc aggacaccaa   1980
gttcattcac accaaggcca accgctttga ggaagtggcc tggtccaaat acaatccccg   2040
agaccagctc taccttcaca tcgggctgaa accaagggtc cgagatcatt accgggccac   2100
taaggtggcc ttttggaaac atctggtgcc ccacctatac aacctgcatg acatgttcca   2160
ctatacgtcc accaccacca aagtgccgcc tccggatacc acccacagct cccacatcac   2220
ccgcaggccc aatggcaaga cctggagcac caagcggcca gccatctcac ctgcctacag   2280
caacgagaat gcccaggggt cctggaacgg ggaccaggat gcagggccac tcctggtgga   2340
gaaccctcgt gactactcca ctgaattaag tgtcaccatc gccgtggggg cctccctcct   2400
gttccttaac gttctggcct tcgctgccct ctactaccgt aaggacaaac ggcgccagga   2460
gcccctgcgg cagcctagcc ctcagcgggg agccggggcc ccggagttgg gagctgctcc   2520
agaggaggag ctggcagcat tacaactggg ccccacccac cacgagtgtg aggccggtcc   2580
cccccatgac acgctgcgcc tcactgcatt gcccgactac accctgaccc tgcggcgctc   2640
cccggatgac atcccactca tgacccccaa caccatcact atgatcccca actccctggt   2700
agggctgcag acattgcacc cctataacac ctttgccgca gggttcaaca gtaccgggct   2760
gccccactca cactccacta cccgggtata gctccaactc agagcacagc caatctccag   2820
gctccctccc tcccagatcc aggaacacat gcacacacac acacacacac acgcagacac   2880
acacacacac acacatatat gtatacgcac gcacccacac cctacagcag atccacctgc   2940
acaaacatag acagatgtgg acatgcaccc gcatgtacaa aaacacaaat acggaagtaa   3000
acctgaacaa accctttaaa tggggacgca gatgagtcct cggtaaaccg aggacccatg   3060
aaacagcagc tgaagccagc tccctgaatc tgaccacaga cactcctggg gggcctgaaa   3120
gcaacagctg gacacccccct tggtgctcgc cttcggcctc tcttggaact gcaccaccga  3180
ccaactccag acttgggagc tttaaagagc aggatagctc ttcctcccca ggacttggtc   3240
tttttctgg gtcttgtttt gttgattttt ctttttaat tttggaacaa atgcttttcc    3300
aacccatgag tgctaagagc ctctggaagg gagggcttca ggcccgaagg tctctctggc   3360
tctaggaccc ccagtgctca cacaatcaga ccaaggaaca agacccccag gaaggaaaca   3420
gatttaagca agaccatggg gtggaaggag aaaggggcta gcactggatg gagctggagg   3480
gtcgtagggg agagatctcc aactctctct gtgtccgtgt ggagggctgc agagcctgca   3540
gggtgacctg cttccccaaa ggccaacagc attggcctgg ccagaccagg tgaccttaga   3600
```

```
tttggtgaac aacgtactat ggaagccaca tcactattgg gcccccaggt ctgatctggg   3660

ttttgcctct gcccttgggg aaatgctatc agaaattcgc cccattttct ttacagtctt   3720

ttgtgtctgt catttctctt tcaaaaaggc ggtgtttttt gttgttgttg gttttttttt   3780

tttttaaag aaaagttctt aaaacactaa cggaaaccca tggagtttgt cctttgtaaa   3840

aattttaaac acagtgtctt gatataaaaa taaaaaatcc agttagcact cccaaaaaaa   3900

aaaaa                                                               3905
```

<210> SEQ ID NO 5
<211> LENGTH: 5167
<212> TYPE: DNA
<213> ORGANISM: Homo sapiens

<400> SEQUENCE: 5

```
tttttttccc ttccttcatc tcctggcctc ggataagata aggcttgggg gatgcacgaa     60

ataatccaag tgattgatta gacctggcat ggcttggttg ggctggagaa agatcggggc    120

gcgctggaaa ccccgcgtga agatgaaatg actttttcga aagacttatc tttctgcagg    180

ctcgcctctg agctttgtct ccttggagcc acctcactta gacagcttcg gatgtggatg    240

cagatttgaa ccatgttgcg tccccaggga ctgctatggc tccctttgtt gttcacctct    300

gtctgtgtca tgttaaactc caatgttctt ctgtggataa ctgctcttgc catcaagttc    360

accctcattg acagccaagc acagtatcca gttgtcaaca caaattatgg taaaatccag    420

ggcctaagaa caccattacc cagtgagatc ttgggtccag tggagcagta cttaggggtc    480

ccctatgcct cacccccaac tggagagagg cggtttcagc caccagaatc ccccatcctcc   540

tggactggca tccgaaatgc tactcagttt tctgctgtgt gcccccagca cctggatgaa    600

agattcttat tgcatgacat gctgcccatc tggtttacca ccagtttgga tactttgatg    660

acctatgttc aagatcaaaa tgaagactgc ctttacttaa acatctatgt gcccatggaa    720

gatgatattc atgaacagaa cagtaagaag cctgttatgg tctatatcca tgggggatct    780

tacatggagg gaaccggtaa catgattgat ggcagcattt tggccagcta tgggaacgtc    840

atcgttatca ccattaacta ccgtctggga atactagggt ttttaagtac cggtgaccag    900

gcagcaaaag gcaactatgg gctcctggat cagattcaag cactgaggtg gattgaggag    960

aatgtcggag cctttggcgg ggaccccaag agagtgacta tctttggctc gggggctggg   1020

gcctcctgtg tcagcctgtt gaccctgtcc cactactcag aaggtctctt ccagaaggcc   1080

atcattcaga gcggcactgc cctgtccagc tgggcagtga actaccagcc ggccaagtac   1140

actcggatat tggcagacaa ggtcggctgc aacatgctgg acaccacgga catggtagaa   1200

tgtctgaaga acaagaacta caaggagctc atccagcaga ccatcacccc ggccacctac   1260

cacatagcct ttgggccggt gatcgacggc gacgtcatcc cagacgaccc ccagatcctg   1320

atggagcaag gcgagttcct caactacgac atcatgctgg gcgtcaacca aggggaaggc   1380

ctgaagttcg tggacggcat cgtggataac gaggacggtg tgacgcccaa cgactttgac   1440

ttctccgtgt ccaacttcgt ggacaacctt tacggctacc ctgaagggaa agacactttg   1500

cgggagacta tcaagttcat gtacacagac tgggccgata aggaaaaccc ggagacgcgg   1560

cggaaaaccc tggtggctct ctttactgac catcagtggg tggcccccgc cgtggccacc   1620

gccgacctgc acgcgcagta cggctccccc acctacttct atgccttcta tcatcactgc   1680

caaagcgaaa tgaagcccag ctgggcagat tcggcccatg gcgatgaagt cccctatgtc   1740

ttcggcatcc ccatgatcgg tcccacagag ctcttcagtt gtaatttctc caagaacgac   1800
```

```
gtcatgctca gtgccgtggt gatgacctac tggacgaact tcgccaaaac tggtgatcca   1860
aaccaaccag ttcctcagga taccaagttc attcatacaa aacccaatcg ctttgaagaa   1920
gtggcctggt ccaagtataa tcccaaagac cagctctatc tgcatattgg cttgaaaccc   1980
agagtgagag atcactaccg ggcaacgaaa gtggctttct ggttggaatt ggttcctcat   2040
ttgcacaact tgaacgagat attccagtat gtttcaacaa ccacaaaggt tcctccacca   2100
gacatgacat catttcccta tggcacccgg cgatctcccg ccaagatatg gccaaccacc   2160
aaacgcccag caatcactcc tgccaacaat cccaaacact ctaaggaccc tcacaaaaca   2220
gggcccgagg acacaactgt cctcattgaa accaaacgag attattccac cgaattaagt   2280
gtcaccattg ccgtcggggc gtcgctcctc ttcctcaaca tcttagcctt tgcggcgctg   2340
tactacaaaa aggacaagag gcgccatgag actcacaggc accccagtcc ccagagaaac   2400
accacaaatg atatcactca catccagaac gaagagatca tgtctctgca gatgaagcag   2460
ctggaacacg atcacgagtg tgagtcgctg caggcacacg acacgctgag gctcacctgc   2520
cctccagact acaccctcac gctgcgccgg tcgccggatg acatcccatt tatgacgcca   2580
aacaccatca ccatgattcc aaacacattg atggggatgc agcctttaca cacttttaaa   2640
accttcagtg gaggacaaaa cagtacaaat ttaccccacg gacattccac cactagagta   2700
tagcttttcc ctatttcccc tcctatccct ctgcccctac tgctcagcaa tgtaaaagag   2760
acaaataagg agaaagaaaa tctccaaacc aggaatgttt ttgtgccact gactttagat   2820
aaaaatgcaa aagggcagtc atcctgtccc agcagaccct tctcattggc attttccagt   2880
attgtgagat caatttctga ccatatgaaa tgtgaaaagt atatgtttct gttacaatac   2940
tgctttaaga tctaaaccat gccaacagat gtttcgtgtg actaggacat caccatttca   3000
aggaactgtg tgtttccaac atcatggtag cagcacacac ttccaaagct cagccaggga   3060
cacttaatat tttttaatta caatggaaat ttaaacattt ttatgtgggc tacacaatgg   3120
atggctcttc ttaagtgaag aaagactcta taggctttta cacagcacat gaagcagtaa   3180
tccagaaaga aggaaatgca gaattttatt atcaaagtaa gcgaattgac tgtgcagaaa   3240
aattgtaggg ttctgtggaa ggaggtattc tgccagcctg aactatattt aagaaacttt   3300
gtaaaaaata aaaatgtata tagctgtgag ctcaaacaaa aactgcagac aaacaaaaaa   3360
gagaaaagct tttatttgtg ttttcagttt gaaagaactt ttagcaaggt tgtgctttca   3420
aacacatatt agtcctacca ccttagttcc tctacagcaa aagaggcttt tcttcttaat   3480
tacatgtaaa caaagacatg ggattttctg acgtaagatt ttcatttgta ggaatatgtg   3540
atgtcaaatg gaagactcag aagttttgtg tggcctattt ctccctgtca ggttgcacag   3600
atgcatgtag agcattctta ggagaccatt gttttagaaa actttgattt gtacatgtta   3660
gttttcatga aattgcaaca cagagatagg tcctaaaagt ggaatgtatt taaaacttgt   3720
tgaattagac acacacacac agacacacac aaagaatcag cagagaaaac aaaatacaag   3780
tcctgttctg tagttcttgc cctttgaata tatttgggaa gagttgcttc ctatttcagg   3840
accctgccaa aaaagaagaa agcttgcctt tggtggggct atgccccttg gagtaaatac   3900
agctctgtgt tccctagcag ctgccggagg atttggctga tgaagtacct gctcagctta   3960
gctaatcaga ttaaaggaag acatgtatgt cttttgttta agcacctagt cccttatgta   4020
tcagtaaaca ggtttttaaa aatcttttat gtcatttata ggataaaaca tatgcttgtc   4080
tgaaaatatc accttttgtg gatttatctg atcaccaaat aataaatatt aagaagaatg   4140
ggggaaaaag gatagaatat taaaactgct ttgcataggt tttggggaa attaggatat   4200
```

```
cttcactgac aagacactga atggaattta ttcacccatt ttaaattggt tacttgggga   4260
tcagagattt gtctctccaa cagcttgtgg ttttcttatt actcattttc aggaaagttt   4320
gtagtattac aaggcagaag gaaacacagt agcaatggtt gctctatatt ttgtctttca   4380
aagattactg cattaccaag aaacagtagc caaagatgtt tgaagatcat gtcccttagc   4440
tgcattgtgg gttattctag aaatccaatg ttaaatgcct ctactaaagt ggggattccc   4500
cataaaaatt gtccagctac ctgactcttt tgcaataaca actttgatta ctgaatccat   4560
acactcaaac tatagtgata tatcagtgtt tgggagtgac ctctagaaaa aagaaaactg   4620
tttttagaaa tacataaaat cacttccaaa tcctgttgct tatgttgggt taaatttgaa   4680
agcaattctc tatatataaa tatgtgaaat attatgatct gaacttagca cacatgaagc   4740
aacatttctt tgctacacag aggtgtcttg gaaagatttc attcccaatt catttttcat   4800
agatctataa tcaggcaatt tctgcaagca atgtatgacc ccacctgagc aaccacaaat   4860
aggctctcca tgaaactgca aaggaactga tgtgtggcat ccatgctggt tttgtctgtc   4920
tataatatga attcaagtat ctgttcatat ttccaattgt ctcctgctag caatatgtgc   4980
cacaacatga cagtcttgtg acatcttaag gaaaagaaga gttcctgtta aatgaatagc   5040
tttagctttt acaggggatt atgattaaaa gtgatttagt acatcttaca tgatatctca   5100
tttctacgtg aaaagaagtt atagaatctt catagagttc catgagaaaa atatacttgc   5160
tatttat                                                             5167
```

<210> SEQ ID NO 6
<211> LENGTH: 5454
<212> TYPE: DNA
<213> ORGANISM: Homo sapiens

<400> SEQUENCE: 6

```
atttaagcga ttttttttcc ctccttcatc gccgggcctc ggataagatg acggcttggg     60
tgatgcacga aataacgcac gtgattgatt agacctggct tggcttggct agggaacgat    120
ccaggcgcgc tggagacccc gcgtgaagat gaaatgacgg ctgccttgga gttttcataa    180
gaaattgtcc ctggaggtgt tggatgatca cagcttcctt ggagcattgc agttgctgga    240
atccagtttc aggattaagg gagggctgcc tccttgcaat gggctgccaa gaaaacggct    300
gtgcttgttc ttaacctcag gctctgtctg tgatcagtct gagagtctct cccaggtcta    360
ctgctccctg gaaagcccta tctctctgca ggctcgcctc tgggctttgt ctccttggag    420
ccacatcact gggacagctg tggatgtgga tgcagatttg aaccatgtca cggccccagg    480
gactgctatg gcttcctttg ttgttcaccc cggtctgcgt catgttaaac tccaatgtcc    540
tcctgtggtt aactgctctt gccatcaagt tcaccctcat tgacagccaa gcacagtatc    600
cagttgtcaa cacaaattat ggcaaaatcc ggggcctaag aacaccgtta cccaatgaga    660
tcttgggtcc agtggagcag tacttagggg tcccctatgc ctcacccccc actggagaga    720
ggcggtttca gcccccagaa cccccgtcct cctggactgg catccgaaat actactcagt    780
ttgctgctgt gtgcccccag cacctggatg agagatcctt actgcatgac atgctgccca    840
tctggtttac cgccaatttg gatactttga tgacctatgt tcaagatcaa aatgaagact    900
gcctttactt aaacatctac gtgcccacgg aagatgatat tcatgatcag aacagtaaga    960
agcccgtcat ggtctatatc catgggggat cttacatgga gggcaccggc aacatgattg   1020
acggcagcat tttggcaagc tacggaaacg tcatcgtgat caccattaac taccgtctgg   1080
gaatactagg gtttttaagt accggtgacc aggcagcaaa aggcaactat gggctcctgg   1140
```

```
atcagattca agcactgcgg tggattgagg agaatgtggg agcctttggc ggggacccca   1200
agagagtgac catctttggc tcgggggctg ggcctcctg tgtcagcctg ttgaccctgt   1260
cccactactc agaaggtctc ttccagaagg ccatcattca gagcggcacc gccctgtcca   1320
gctgggcagt gaactaccag ccggccaagt acactcggat attggcagac aaggtcggct   1380
gcaacatgct ggacaccacg gacatggtag aatgcctgcg gaacaagaac tacaaggagc   1440
tcatccagca gaccatcacc ccggccacct accacatagc cttcgggccg gtgatcgacg   1500
gcgacgtcat cccagacgac ccccagatcc tgatggagca aggcgagttc ctcaactacg   1560
acatcatgct gggcgtcaac caaggggaag gcctgaagtt cgtggacggc atcgtggata   1620
acgaggacgg tgtgacgccc aacgactttg acttctccgt gtccaacttc gtggacaacc   1680
tttacggcta ccctgaaggg aaagacactt tgcgggagac tatcaagttc atgtacacag   1740
actgggccga taaggaaaac ccggagacgc ggcggaaaac cctggtggct ctctttactg   1800
accaccagtg ggtggccccc gccgtggcca ccgccgacct gcacgcgcag tacggctccc   1860
ccacctactt ctatgccttc tatcatcact gccaaagcga aatgaagccc agctgggcag   1920
attcggccca tggtgatgag gtcccctatg tcttcggcat ccccatgatc ggtcccaccg   1980
agctcttcag ttgtaacttt tccaagaacg acgtcatgct cagcgccgtg gtcatgacct   2040
actggacgaa cttcgccaaa actggtgatc caaatcaacc agttcctcag gataccaagt   2100
tcattcacac aaaacccaac cgctttgaag aagtggcctg gtccaagtat aatcccaaag   2160
accagctcta tctgcatatt ggcttgaaac ccagagtgag agatcactac cgggcaacga   2220
aagtggcttt ctggttggaa ctcgttcctc atttgcacaa cttgaacgag atattccagt   2280
atgtttcaac aaccacaaag gttcctccac cagacatgac atcatttccc tatggcaccc   2340
ggcgatctcc cgccaagata tggccaacca ccaaacgccc agcaatcact cctgccaaca   2400
atcccaaaca ctctaaggac cctcacaaaa cagggcctga ggacacaact gtcctcattg   2460
aaaccaaacg agattattcc accgaattaa gtgtcaccat tgccgtcggg gcgtcgctcc   2520
tcttcctcaa catcttagct tttgcggcgc tgtactacaa aaaggacaag aggcgccatg   2580
agactcacag gcgccccagt ccccagagaa acaccacaaa tgatatcgct cacatccaga   2640
acgaagagat catgtctctg cagatgaagc agctggaaca cgatcacgag tgtgagtcgc   2700
tgcaggcaca cgacacactg aggctcacct gcccgccaga ctacaccctc acgctgcgcc   2760
ggtcgccaga tgacatccca cttatgacgc caaacaccat caccatgatt ccaaacacac   2820
tgacggggat gcagcctttg cacactttta acaccttcag tggaggacaa aacagtacaa   2880
atttacccca cggacattcc accactagag tatagctttg ccctatttcc cttcctatcc   2940
ctctgcccta cccgctcagc aacatagaag agggaaggaa agagagaagg aaagagagag   3000
agaaagaaag tctccagacc aggaatgttt ttgtcccact gacttaagac aaaaatgcaa   3060
aaaggcagtc atcccatccc ggcagaccct tatcgttggt gttttccagt attacaagat   3120
caacttctga ccctgtgaaa tgtgagaagt acacatttct gttaaaataa ctgctttaag   3180
atctctacca ctccaatcaa tgtttagtgt gataggacat caccatttca aggccccggg   3240
tgtttccaac gtcatggaag cagctgacac ttctgaaact cagccaagga cacttgatat   3300
tttttaatta caatggaagt ttaaacattt ctttctgtgc cacacaatgg atggctctcc   3360
ttaagtgaag aaagagtcaa tgagattttg cccagcacat ggagctgtaa tccagagaga   3420
aggaaacgta gaaatttatt attaaaagaa tggactgtgc agcgaaatct gtacggttct   3480
gtgcaaagag gtgttttgcc agcctgaact atatttaaga gactttgtaa aaaagaaaaa   3540
```

tgtatatagc tgtgagttta aacaaaaacc acaaacagac aaacaagaaa aaaagctttt 3600
attggtgttt tcactttgaa agagctttta gcaaggttgt gcttttcatt gtgctctgta 3660
cgtatataaa tatatatata tacacacaca cacacacaca ttagtcatat cacctctgtt 3720
tcctccccaa caaaagaggc ttttcttctt aattacttgt ggtaaacaaa gacatgggat 3780
tttcttacat gagattctca tttgtaggag gatgtgatgt cccacagaag acccagacgg 3840
tctgtgtggc ctatttcccc cgtcaggttg cacaggtgca tgcaagagca ttcttaggag 3900
accactgttt tgaaaaactt ttgacttgta cgtgttagcc ttcatgaaat tgcagtacag 3960
agatgggtcc ccaaagtgga gtgtatttac agcttgttaa attagagaca tgcacacaca 4020
aagaatcagt agggagaaac aaaaatacaa gtcccgttct gtagctctgg ccctttgaat 4080
atgtttagga agagttgctt cccatttcag ggccctgcca aaaaaagaag aaagcttgcc 4140
tttggtgggg ctatgcccct tggagtaaat acggctctgt gttccctagc agctgcggga 4200
gggtttggcc gatgaagtac ctgctcagct tagctaatca gattgaagga agacatgtgt 4260
ctttcctttt tgtttaagca ctcggtccct tatttatcag taagcaggtt tttaaaaatc 4320
ttttatatca tttatgggat caaacatatg attgtctgaa aacatcactt tttgtggatt 4380
tgtgtatccg gtcaccaaac ggtgaatatt atagaagaat gggggaagaa aggatagaat 4440
attaaaactg ctttgcatgg gttttctggg aaattaggat aacttcactg agaagacatt 4500
gaatggaaat tattcaccca ttttaaattg gtgacctagg gatcagagat ttgtctttcc 4560
aacagcttgt catttttca tttctcttct catttttcag gaaagttttg agtgttataa 4620
ggtggaagga aacatagtag caatggatac ttttttgaaa aattattgca ttaccaagaa 4680
acagtagcca aagatatttg aagatcatgt tcctcggctc cattgtgggt tattctagaa 4740
atccagtctt aaatctctcc gctaaagtgg acattcccca taaaaattgt ccagctgcct 4800
ggctcttttg caataacaac ctttgattac tgaatcccta cactcaaact atagtgatat 4860
atcagtgttt gagagtgacc tctagaaaaa agaaaagtgt ttttagaaat gtgtacaagt 4920
cacccccaaa tcctattgct tatcttgggt taaatttgag agtgattctc tgtatataaa 4980
tatgtgaaat attattatct caacttagca cacgtgaagc aacatttctt tcctacagag 5040
aggtgtcatg gtaagatttc attccgaatt cattgtttca tagagctatg atcaggccat 5100
ttctgcaagc aatgtatgac ccccacctgag caaccacaaa taggctctct gtgaaactac 5160
aaaggaagtt atgtgtggca tccatgttgg tttcgtctgt ctgtaatgtg aattccagta 5220
tttgtttagt atttccagtt gtctcctgct agcaatatgt acagtaacgc gtcaggcttg 5280
tgacatttga ataaggaaaa acagagttcc tgttaagtga ataactttag cttttacagg 5340
ggattatgat caaaagtgat tttagtacat cttaaatgat atcttatttc tacatggaaa 5400
gaagttatag aatcttcata gagttctatg agaaaaaata tacttgctat ctat 5454

<210> SEQ ID NO 7
<211> LENGTH: 7505
<212> TYPE: DNA
<213> ORGANISM: Homo sapiens

<400> SEQUENCE: 7
ctctctctct ctctctctct ctctctttct ttctttccga tggggaagag agggtggtga 60
caagttagaa gcgcttgcgg aaggtccccg cccccaggat caggctcccc ctgcaagggg 120
acgatgcaaa ggtaaaagca cctcgctccg cagcatccag acctggaggg gctgcgacca 180
cgggccgagc ccacccattc cccagccaaa ggacgggccc gccgctctcc atggtactgc 240

```
ggagagctca gctccgccct tctctttcag aaggacagca cccggcgtca cgtaacccag    300
ccttctcagg ctccaccacc gccttttcct tcccagctct ttccctctcc tccccctcct    360
cctccttctc ctcctcctcc tcctcctgct cccctccgtt gcctgttctc ccctcccgca    420
ctcctggaga tagacgctca agcctgacgc ctctgaaaag gcagcagcag tcgccttatc    480
catagacctc aggaaattcg ctttgaccga tgcatgcttc aggctctggc tcgagctgag    540
gggaataacc gggcagatgt ctgagtcctt aaaaaagaca agataaaacc aaaatgcatc    600
accaacacac aaccaattga tgtgctggca tcttagcttg gccctgcaga ggcagagaga    660
aaagaagagg agctgttgcg atttccacat ctaacagctt ctggctattt cgcaactgct    720
gggtttgagt cctactgttg ccgtggctga aaagagaagt aaaatccaac ttgtgagacc    780
acgcacaagg aattaggctt tggctgcagc ggtgctgaag cccatgctat gacagaagaa    840
gcaggccttt gaagctatcc tcgggttaag aaatggtgcc ctaaagaggc aagcatccct    900
ttctccgttc tgctgtaaga caccacatct gaaggagaca gacttgaggc attcacaagc    960
atccaaggat actggctcac tgctggcttc ctgtactttc ttgagaaaag tgttttcttt   1020
ttactgactc tcactgcttc cttttggcct ggtaccactg gtggaacctg gcagataatg   1080
ggatttgagg agttaagtat ctgttgacac tgcagatact cttaaattag ttaatcagac   1140
tcaaatgggt cagtgctttc ccttgatctt ttgttgaagc cttttccaga acgttgtctc   1200
caaagtgcat cctccctttg gtctggaagt tctgtggcta ccctgtacca ctggggtcaa   1260
cgttttccag ttggaagagg actacaggga gagagggcgg ggttattgga agaagaagaa   1320
gaaaaaaaga actagataaa ggagggcaca tccctctcac tcccgccttt ccccttacct   1380
ttctgtctct cgggaccctt atttcttcgt cacggtgtcc aggaccattt tgaccctgtc   1440
ggccccggca cccccccgcc gcaccccagc cccgagcatg ggacggcgc tgctccagcg    1500
cgggggctgt tttcttctgt gcctctcgct gctgctcctg ggctgctggg cggagctggg   1560
cagcgggctg gagtttccgg gcgccgaggg ccaatggacg cgcttcccca agtggaacgc   1620
ctgctgcgag agcgagatga gcttccagct caagactcgc agcgcccgcg gcctcgtgct   1680
ctacttcgac gacgagggct tctgcgactt cctggagctg attctgacgc gcggcggccg   1740
cctgcagctc agcttctcca tcttctgcgc tgagcctgcg acgctcctgg ccgacacgcc   1800
ggttaacgac ggcgcctggc acagcgtgcg catccgccgc cagttccgca acaccacgct   1860
cttcatcgac caggtggagg ccaagtgggt ggaggtcaag tccaagcgca gggacatgac   1920
ggtgttcagc ggcctttcg tcgggggct gcccccggaa ctgcgcgccg cggcgctcaa     1980
gctcaccctg gcctcggtga gggagcggga gcccttcaag gggtggattc gtgacgtgag   2040
ggtcaactcc tcgcaggtcc tgcccgtgga cagcggcgag gtgaagctgg acgatgagcc   2100
gcccaacagc ggcgggggaa gcccgtgcga ggcgggcgag gagggcgagg gcggggtgtg   2160
cctcaacgga ggtgtgtgct ccgtggtgga cgaccaggcc gtgtgcgact gctcgcgaac   2220
cggcttccgc ggcaaggact gcagccaaga agacaacaat gtggaaggtc tggcgcacct   2280
gatgatgggc gaccaaggta aaagtaaagg aaaagaagaa tatattgcca cgttcaaagg   2340
atctgaatac ttctgctacg acttgtctca aaaccccatt caaagcagca gtgatgaaat   2400
aactctgtca tttaaaaccc ttcagaggaa tggactgatg cttcacactg ggaaatcggc   2460
tgattatgtc aatcttgccc tgaaaaatgg agctgtctct ctggtcatta atttgggatc   2520
aggggccttt gaagcactag tggagcctgt gaatggaaag tttaatgata atgcctggca   2580
tgatgtgaaa gtcaccagga atctgcgtca gcactcaggc attggacacg ctatggtgac   2640
```

```
aatatcagtg gatgggattc ttaccacaac gggctacacg caagaagatt ataccatgct   2700
ggggtctgat gactttttct atgttggagg cagtcccagc acagccgacc ttccagggtc   2760
accagtcagt aacaacttta tgggctgtct caaagaggtt gtatataaaa ataatgatgt   2820
gaggctggaa ttatctcgac ttgccaagca aggagatcct aagatgaaga tccatggagt   2880
ggtggcattt aaatgtgaga atgttgcaac tttagaccca atcacctttg aaaccccaga   2940
gtctttcatc tctttgccta aatggaatgc aaagaaaact ggctccatat catttgattt   3000
ccgtacaaca gagccaaatg gcctcatctt atttagccat ggcaagccaa gacatcagaa   3060
agatgccaag cacccacaga tgataaaggt ggacttcttt gctattgaga tgctagatgg   3120
ccacctctac ctcctcctgg acatggggtc aggtactata aaaataaaag ccctgttgaa   3180
gaaagtgaat gatggagaat ggtatcatgt ggacttccag agagacggac ggtcaggtac   3240
catttctgtc aacacgttgc gtactcccta cactgctcct ggtgagagtg agattctgga   3300
cctggatgat gagttgtacc tgggggggct gccagaaaat aaagctggcc ttgtcttccc   3360
caccgaggtg tggactgctc tgctcaacta tggctacgtg ggctgcatca gggatttgtt   3420
catcgatggc caaagcaaag atatccggca aatggctgaa gttcaaagta ctgctggagt   3480
gaagccttcc tgctcaaagg aaacagcaaa accgtgcctt agcaaccctt gcaaaaacaa   3540
tggcatgtgc agggatgggt ggaacagata tgtctgtgat tgttccggaa caggctatct   3600
tggcaggtcc tgtgagagag aggcaacggt tttgagctat gatgggagca tgtttatgaa   3660
aattcagctc cccgtagtca tgcatacgga ggctgaggat gtttccttac ggttccgatc   3720
ccagcgtgca tatggcattc tgatggcaac cacttctaga gactctgctg acaccctccg   3780
cctggagcta gacgcaggac gtgtgaaact gacggtcaat ctagattgta tcaggattaa   3840
ctgtaattcc agcaaaggtc ccgagactct tttgctggc tataacctca atgataacga   3900
gtggcacaca gtgcgtgtag ttcggcgtgg aaaaagttta aagttaacag tggatgacca   3960
acaggccatg acaggtcaaa tggcaggtga tcatactagg ctggagttcc ataacataga   4020
gactggcatc atcacagaac gacggtatct ttcttctgtc ccctccaact tcattggaca   4080
cctgcagagc ttgacattta atggaatggc atacattgac ctgtgtaaaa atggcgacat   4140
agattactgt gagcttaatg ccagatttgg cttcaggaac atcatagcag atcctgtcac   4200
cttcaagacc aaatcgagct atgttgcctt agctaccttg caagcctaca cttctatgca   4260
tctttttttc cagttcaaga caacatccct agatggatta attctatata acagtgggga   4320
tggaaatgac tttattgtgg ttgaattagt taaagggtac ttacattacg tgtttgattt   4380
gggaaatggt gctaacctca tcaaaggaag ctcaaataaa cctctcaatg acaatcagtg   4440
gcacaacgtg atgatatcaa gggacaccag caacctccac actgtaaaga ttgacacaaa   4500
aatcacaacg caaatcaccg ccggagccag gaacttagac ctcaagagtg acttatatat   4560
aggaggagta gctaaagaaa catacaaatc cttaccaaaa cttgtacatg ccaaagaagg   4620
ctttcaaggc tgcctggcat cagttgattt aaatggacgg cttccggacc tcatctccga   4680
tgctcttttc tgcaacggac agatcgagag aggatgtgaa gggcccagca caacctgcca   4740
agaggactca tgttccaatc aaggtgtgtg cttgcaacaa tgggatggct tcagctgtga   4800
ctgtagtatg acttccttca gtggaccact ctgcaatgac cctgggacga catatatctt   4860
tagcaaaggt ggtggacaaa tcacgtataa gtggcctcct aatgaccgac ccagtacacg   4920
agcagacaga ctggccatag gttttagcac tgttcagaaa gaagccgtat tggtgcgagt   4980
ggacagttct tcaggcttgg gtgactacct agaactgcat atacaccagg gaaaaattgg   5040
```

```
agttaagttt aatgttggga cagatgacat cgccattgaa gaatccaatg caatcattaa   5100
tgatgggaaa taccatgtag ttcgtttcac gaggagtggt ggcaatgcca cgttgcaggt   5160
ggacagctgg ccagtgatcg agcgctaccc tgcagggcgt cagctcacaa tcttcaatag   5220
ccaagcaacc ataataattg gcgggaaaga gcagggccag cccttccagg gccagctctc   5280
tgggctgtac tacaatggct tgaaagttct gaatatggca gccgaaaacg atgccaacat   5340
cgccatagtg ggaaatgtga gactggttgg tgaagtgcct tcctctatga caactgagtc   5400
aacagccact gccatgcaat cagagatgtc cacatcaatt atggagacta ccacgaccct   5460
ggctactagc acagccagaa gaggaaagcc cccgacaaaa gaacccatta gccagaccac   5520
agatgacatc cttgtggcct cagcagagtg tcccagcgat gatgaggaca ttgacccctg   5580
tgagccgagc tcaggtgggt tagccaaccc aacccgagca ggcggcagag agccgtatcc   5640
aggctcagca gaagtgatcc gggagtccag cagcaccacg ggtatggtcg ttgggatagt   5700
agccgctgcc gccctgtgca tccttatcct cctctatgcc atgtacaagt acagaaaccg   5760
ggatgaaggc tcataccatg tggacgagag tcgaaactac atcagtaact cagcacagtc   5820
caatggggct gttgtaaagg agaaacaacc cagcagtgcg aaaagctcca acaaaaataa   5880
gaaaaacaag gataaagagt attatgtctg atcccaagat cttaaatgga cacttgtata   5940
gaaatagtct tcattttatc tgagacataa tataaactta tttactttcc tttttatgaa   6000
gcacatacaa aagaagacag ggaatgcaat caggaaggaa agactttttta aaaaataaaa   6060
acaagtatct catgctcttg tttctcaaaa aagaaaaaca aaaaacaaaa aacaggggcc   6120
aataaattcc ctaacatcca cagtgttttc atttactctg cttgtcttta tgttgctgga   6180
acatttctaa aagacagtga tgaccgcacg cattcataaa gcaaaggagt actacagcat   6240
caaggcacaa cacaaaaacc aacacaaaac ataacacaaa aaagaagcta cctatgatcc   6300
tggatttagc caaagtgcta gcgctttcct gagaagtcag tccaattgcc agagaagact   6360
gtccttttga gtgactcaac ctgcaaacct ttaagagttt gccgcctggt gcaactggag   6420
cagtggttgg aacttgcatt tgaaacaaag tgctggcttt tttgaagact tgtgtaggaa   6480
cacattcaaa aagccccttt ctggttgtga gagaggaaaa aaaagtatgg aggccttatt   6540
ttcaaaaatg tgaaatataa ggcacgtttt cacacaaaat ttcaaaacaa aaacaagagg   6600
gcatagatgc aatcattggg aaattttcat gcacgcttat tatgttatta catatgttta   6660
tataaaatcc atctctgtgt gctttctgga ctgtgataag tgacgtttta tagcctgttg   6720
tatagaaaat gcaaaatata tctctgctct tcagccattt ttggtaaatt caatgttata   6780
agtgttgcta agtataggga gttttatgac atcagagcaa caattatttc agttgggttt   6840
ttcttttttt ttgccaccat tataaattgc cacaattact tttatttttt aaagaaatta   6900
cagtgtagtg tttattctaa ggaagatatg tatgaatgta tatacaaaga ctcagctact   6960
tcttttctta tatgtacagc cttcattctg ttgcaattaa gttttagtac ttgtatgaaa   7020
ggtgtgaatt agaaagtcac atatatacat atgtatctta taatcttttc tccctgaaat   7080
actcacattc ccacatacat tcactatttt cacacacaca cacacacaca cacacacaca   7140
cacacacaca cacacacgaa tccacagcaa tccatcagat atgctggaag atccaaacgt   7200
gcatacagta gcaaatattt attgacaaat tgaaaagcag gaaggaagag ggttgtgcca   7260
aggtattgat gacaaatggg gtgatttgct tcattgagat cttgctccca ggtaacctta   7320
agaagatttt agtccctaaa gaaatgaacc tttccttatc aaatagaata tcactgatat   7380
actgctgcat gaataagaac cattatgtgg gcaggttatg gaagcaaaat tggttaatct   7440
```

acaccttaac tctggctgct gcaattgaaa actttctttc taataaaata atatatatat 7500
ctctg 7505

<210> SEQ ID NO 8
<211> LENGTH: 3712
<212> TYPE: DNA
<213> ORGANISM: Homo sapiens

<400> SEQUENCE: 8 cttttttct ttttctttt ctttttctgt ttctctccct tactccttcg tctgcatctt 60
cttctcagct gcctttccgc cgttcgattc ccacttcctt cagaagggcg cactcttccc 120
tctgaacccc tcgccgggcg taagtgtcag gaggcggcgg acgcggagat tgcctcggga 180
gcaggcgatg cgcgccgctg ctccgcgcgc tgcccggggg aggctggcgc tagcgggcga 240
gccggccggg gctgaatgga gggaaggggc gcctggattc catggggtct gcttctgtct 300
tgaaaggagg ttgggccggc gaagtggcct ccctagtccc cgcacacaaa gctaaatgga 360
tttacctagt ggattcgcgg tggatgtctg tcatgtagaa gtgaggacct tccaggagga 420
gctttaaaca atttctcggc cccccacccg ccggcacgca ctctcgcccg aaactctttg 480
ggagtatctc tcgagaacct ggagccctgg aaatctggga gcagccaccc gctccgcgct 540
tgctgttccc ggggctgcct ttccggacaa gcccctctcc agctgcattc gcctcggcta 600
tgtttcggat tgtttggggt gctaggcacg gcggactcca ggaccccgag aagactgtcc 660
gaaggaggga gaggatgggt gccctggcgc ggtgaggcgg ccggcccctc agcccactcc 720
gcgccgcccg ctcccctgcg ccctctcctc tccccgcgcc ccaaactttg cctcccgcgg 780
cggctgcccc tcggcgggcg ccccgccatg taccagagga tgctccggtg cggcgccgag 840
ctgggctcgc ccgggggcgg cggcggcggc ggcggcggcg gcggcgcagg ggggcgcctg 900
gccctgcttt ggatagtccc gctcaccctc agcggcctcc taggagtggc gtggggggca 960
tccagtttgg gagcgcacca catccaccat ttccatggca gcagcaagca tcattcagtg 1020
cctattgcaa tctacaggtc accggcatcc ttgcgaggcg gacacgctgg gacgacatat 1080
atctttagca aaggtggtgg acaaatcacg tataagtggc ctcctaatga ccgacccagt 1140
acacgagcag acagactggc cataggtttt agcactgttc agaaagaagc cgtattggtg 1200
cgagtggaca gttcttcagg cttgggtgac tacctagaac tgcatataca ccagggaaaa 1260
attggagtta agtttaatgt tgggacagat gacatcgcca ttgaagaatc caatgcaatc 1320
attaatgatg ggaaatacca tgtagttcgt ttcacgagga gtggtggcaa tgccacgttg 1380
caggtggaca gctggccagt gatcgagcgc taccctgcag ggcgtcagct cacaatcttc 1440
aatagccaag caaccataat aattggcggg aaagagcagg gccagccctt ccagggccag 1500
ctctctgggc tgtactacaa tggcttgaaa gttctgaata tggcagccga aaacgatgcc 1560
aacatcgcca tagtgggaaa tgtgagactg gttggtgaag tgccttcctc tatgacaact 1620
gagtcaacag ccactgccat gcaatcagag atgtccacat caattatgga gactaccacg 1680
accctggcta ctagcacagc cagaagagga aagcccccga caaaagaacc cattagccag 1740
accacagatg acatccttgt ggcctcagca gagtgtccca gcgatgatga ggacattgac 1800
ccctgtgagc cgagctcagg tgggttagcc aacccaaccc gagcaggcgg cagagagccg 1860
tatccaggct cagcagaagt gatccgggag tccagcagca ccacgggtat ggtcgttggg 1920
atagtagccg ctgccgccct gtgcatcctt atcctcctct atgccatgta caagtacaga 1980
aaccgggatg aaggctcata ccatgtggac gagagtcgaa actacatcag taactcagca 2040

```
cagtccaatg gggctgttgt aaaggagaaa caacccagca gtgcgaaaag ctccaacaaa   2100
aataagaaaa acaaggataa agagtattat gtctgatccc aagatcttaa atggacactt   2160
gtatagaaat agtcttcatt ttatctgaga cataatataa acttatttac tttccttttt   2220
atgaagcaca tacaaaagaa gacagggaat gcaatcagga aggaaagact ttttaaaaaa   2280
taaaaacaag tatctcatgc tcttgtttct caaaaaagaa aaacaaaaaa caaaaaaacag   2340
gggccaataa attccctaac atccacagtg ttttcattta ctctgcttgt ctttatgttg   2400
ctggaacatt tctaaaagac agtgatgacc gcacgcattc ataaagcaaa ggagtactac   2460
agcatcaagg cacaacacaa aaaccaacac aaaacataac acaaaaaaga agctacctat   2520
gatcctggat ttagccaaag tgctagcgct ttcctgagaa gtcagtccaa ttgccagaga   2580
agactgtcct tttgagtgac tcaacctgca aacctttaag agtttgccgc ctggtgcaac   2640
tggagcagtg gttggaactt gcatttgaaa caaagtgctg gctttttga agacttgtgt    2700
aggaacacat tcaaaaagcc cctttctggt tgtgagagag gaaaaaaaag tatggaggcc   2760
ttattttcaa aaatgtgaaa tataaggcac gttttcacac aaaatttcaa aacaaaaaca   2820
agagggcata gatgcaatca ttgggaaatt ttcatgcacg cttattatgt tattacatat   2880
gtttatataa aatccatctc tgtgtgcttt ctggactgtg ataagtgacg ttttatagcc   2940
tgttgtatag aaaatgcaaa atatatctct gctcttcagc catttttggt aaattcaatg   3000
ttataagtgt tgctaagtat agggagtttt atgacatcag agcaacaatt atttcagttg   3060
ggtttttctt ttttttgcc accattataa attgccacaa ttacttttat tttttaaaga    3120
aattacagtg tagtgtttat tctaaggaag atatgtatga atgtatatac aaagactcag   3180
ctacttcttt tcttatatgt acagccttca ttctgttgca attaagtttt agtacttgta   3240
tgaaaggtgt gaattagaaa gtcacatata tacatatgta tcttataatc ttttctccct   3300
gaaatactca cattcccaca tacattcact attttcacac acacacacac acacacacac   3360
acacgaatcc acagcaatcc atcagatatg ctggaagatc caaacgtgca tacagtagca   3420
aatatttatt gacaaattga aaagcaggaa ggaagagggt tgtgccaagg tattgatgac   3480
aaatggggtg atttgcttca ttgagatctt gctcccaggt aaccttaaga agattttagt   3540
ccctaaagaa atgaaccttt ccttatcaaa tagaatatca ctgatatact gctgcatgaa   3600
taagaaccat tatgtgggca ggttatggaa gcaaaattgg ttaatctaca ccttaactct   3660
ggctgctgca attgaaaact ttctttctaa taaaataata tatatatctc tg           3712
```

<210> SEQ ID NO 9
<211> LENGTH: 6616
<212> TYPE: DNA
<213> ORGANISM: Homo sapiens

<400> SEQUENCE: 9

```
tgcagggatg cggcggcggg agcagccgcc ctgactcgcg gagcatcctc ctcggagagg     60
caccgcggcg gggcgggcgg ggagagaggc gcgaggcggc agacaccgct agccctggct    120
ctgccacccg tcggagacgg ggcggccctg tagctctgct acccaccctc cagcttctgg    180
cgccccgaga accaggcatc cctccctgct cttctgtcgg agcccgcggc gggggagggg    240
cgccgccgcc gccgcctgag ggaagccggc atctgggcct ctgcgcgcct cgccccgcgg    300
ccgggcccat ggcactgtga gcctgcaagg gagccccgct cagcgcgggg agcgcccggc    360
cccctcccgc cccatgcgcc cgcggctctg aagcctgagc gggggccggg ggccgggcgg    420
ggccggggcc gccgtaggca tggcgtccgg gagccggtgg cggccgacac cgccgccgct    480
```

```
gctgttgctg ctgctgctgg cgctggcggc gcgcgcggac ggcctggagt tcggcggcgg    540
ccccgggcag tgggctcgct acgcgcgctg ggcgggcgcg gcgagcagcg gcgagctcag    600
cttcagcctg cgcaccaacg ccacgcgcgc gctgctgctc tacctggacg acggcggcga    660
ctgcgacttc ctggagctgc tgctggtgga cggccgcctg cggctgcgct tcacgctttc    720
gtgcgccgag ccggccacgc tgcagctgga cacgccggtg gccgacgacc gctggcacat    780
ggtgctgctg acccgcgacg cgcgccgcac ggcgctggcg gtggacggcg aggcccgcgc    840
cgccgaggtg cgctccaagc ggcgcgagat gcaggtggcc agcgacctgt tcgtgggcgg    900
catcccgccc gacgtgcgcc tctcggcgct tacgctgagc accgtcaagt acgagccgcc    960
cttccgcggc ctcttggcca acctgaagct gggcgagcgg ccccccgcgc tgctgggcag   1020
ccagggcctg cgcggcgcca ccgccgaccc gctgtgcgcg cccgcgcgca acccctgcgc   1080
caacggcggc ctctgcaccg tgctggcccc cggcgaggtg ggctgcgact gcagccacac   1140
gggcttcggc ggcaagttct gcagcgaaga ggagcacccc atggaaggtc cggctcacct   1200
gacgttaaac agcgaagtag ggtccttact gttctccgag gggggggccg ggagaggagg   1260
agccggcgat gtgcaccagc caacaaaagg caaggaggag tttgtggcga ccttcaaagg   1320
caatgagttc ttctgctacg acctgtcaca caaccccatc cagagcagca ctgatgagat   1380
cacactggcc ttccgcaccc tgcaacgcaa cggcctgatg ctgcatacag gcaagtcggc   1440
cgactacgtc aacctgtccc tcaagtctgg ggctgtctgg ctggtcatca acctaggctc   1500
aggtgccttc gaggcccttg tggaacccgt caatggcaag ttcaacgaca acgcctggca   1560
cgacgtccgg gtcacccgaa acctgcgcca gcacgcaggg attggacacg ctatggtaaa   1620
caaactgcat tatctggtga ccatctcggt ggacgggatc ctgaccacca caggctacac   1680
gcaggaggat tacaccatgc tgggctctga tgacttcttc tacattgggg gcagccccaa   1740
cacagctgac ctgccgggct cgcccgtcag caacaacttc atgggctgcc tcaaggacgt   1800
ggtctataag aacaatgact tcaaattgga actatcccgc ctggcaaagg aaggggaccc   1860
caagatgaag ctgcaggggg acttgtcatt ccgctgtgag gatgtggctg ccctggaccc   1920
tgtgaccttt gagagtcccg aggcctttgt ggcgctgccc cgctggagcg ctaagcgcac   1980
tggctccatc tccctagact tccgcaccac cgagcccaat gggctgctgc tcttcagcca   2040
gggccggcgg gctggggggtg gagctggcag ccacagctct gctcagcggg ccgactactt   2100
tgccatggag ctattggacg gccacctcta tcttctgctg gacatgggat ctgggggcat   2160
caagctgcgg gcatccagcc gcaaggtcaa tgatggcgag tggtgtcacg tggacttcca   2220
gagggatggg cgaaaaggct ccatctcagt gaatagtcgc agcacgccgt tcttggccac   2280
tggagacagc gagattctgg acctggagag tgagctgtac ctgggcggtc tccctgaggg   2340
gggccgggtg gacctgcccc tgcccccaga ggtgtggaca gcagcactcc gggcaggcta   2400
cgtgggctgt gtgcgggacc tcttcataga tgggcgtagc cgagacctcc ggggcctggc   2460
tgaggctcag gggctgtgg gcgttgcccc cttttgctcc cgggagacgc tgaagcagtg   2520
tgcatctgcc ccctgtcgca atgggggcgt ctgtcgagaa ggctggaacc gcttcatctg   2580
tgactgcatc gggaccggct ttcttgggcg ggtctgtgag agagaggcca cggtcctgag   2640
ctacgatggc tccatgtaca tgaagatcat gctgcctaac gccatgcaca cggaggcaga   2700
ggatgtgtcc ctgcgtttca tgtcccagcg ggcctacgga ctcatgatgg ccaccacttc   2760
cagggagtct gccgacaccc tacgcctgga gctggatggg gggcagatga agctcactgt   2820
caacctcgac tgcctgcgcg tcggctgcgc acccagtaaa ggccccgaaa cgctgtttgc   2880
```

```
ggggcacaag ctcaatgaca atgagtggca cacggtgagg gtggtccggc gtggcaagag   2940
cctgcagctg tctgtggaca acgtgactgt ggagggacag atggcaggag cccatatgcg   3000
gctggagttc cacaacattg agacgggcat catgacggag cggcggttta tctccgtggt   3060
gccctccaac ttcatcgggc atctgagtgg gctcgtgttc aatggccagc cctacatgga   3120
ccagtgcaag gatggtgaca tcacctactg tgagctcaat gctcgctttg gcctgcgtgc   3180
catcgtggcc gatcccgtca ccttcaagag tcgcagcagc tacctggcac tcgccacgct   3240
ccaagcctat gcttccatgc acctcttctt ccagttcaag accacggccc ctgatgggct   3300
tcttctgttc aactcgggca acggcaatga cttcattgtc atcgagctgg tcaaggggta   3360
catccactac gtgtttgacc tggggaatgg cccgtccttg atgaagggga actcagacaa   3420
accagtcaat gacaaccagt ggcacaacgt ggtggtgtcc agggacccag gcaacgtgca   3480
cacgctcaag attgactccc gcactgtcac gcagcactcc aatggcgccc gaaacctcga   3540
tctcaaaggg gagttgtaca ttggcggtct gagcaagaat atgttcagca acctgcccaa   3600
gctggtggcc tcccgggatg gctttcaggg ctgcctggcc tcagtggacc tcaacggacg   3660
tctcccagac ctcatcgccg acgccctgca ccgcattggg caggtggaga ggggctgtga   3720
tggccccagc accacctgca ctgaagagtc ctgtgccaac cagggcgtct gcttgcagca   3780
gtgggatggc ttcacctgcg actgcaccat gacttcctat ggaggccctg tctgcaatga   3840
tcccgggacc acatacatct ttgggaaggg gggagcgctc atcacctaca cgtggccccc   3900
caatgacagg cccagcacga ggatggatcg cctggccgtg ggcttcagca cccaccagcg   3960
gagcgctgtg ctggtgcggg tggacagcgc ctccggcctt ggagactacc tgcagctgca   4020
catcgaccag ggcaccgtgg gggtgatctt taacgtgggc acggacgaca ttaccatcga   4080
cgagcccaac gccatagtaa gcgacggcaa ataccacgtg gtgcgcttca ctcgaagcgg   4140
cggcaacgcc accctgcagg tggacagctg gccggtcaac gagcggtacc cggcaggaaa   4200
ctttgataac gagcgcctgg cgattgctag acagagaatc ccctaccggc ttggtcgagt   4260
agtagatgag tggctgctcg acaaaggccg ccagctgacc atcttcaaca gccaggctgc   4320
catcaagatc gggggccggg atcagggccg cccccttccag ggccaggtgt ccggcctcta   4380
ctacaatggg ctcaaggtgc tggcgctggc cgccgagagc gaccccaatg tgcggactga   4440
gggtcacctg cgcctggtgg gggaggggcc gtccgtgctg ctcagtgcgg agaccacggc   4500
caccaccctg ctggctgaca tggccaccac catcatggag actaccacca ccatggccac   4560
taccaccacg cgccggggcc gctcccccac actgagggac agcaccaccc agaacacaga   4620
tgacctgctg gtggcctctg ctgagtgtcc aagcgatgat gaggacctgg aggagtgtga   4680
gcccagtact ggaggagagt taatattgcc cattatcacg gaggactcct tagaccccc    4740
tcccgtggcc acccgatccc ccttcgtgcc cccgcccccct accttctacc ccttcctcac   4800
gggagtgggc gccacccaag acacgctgcc cccgcccgcc gcgcgccgcc cgccctctgg   4860
gggcccgtgc caggccgagc gggacgacag cgactgcgag gagcccatcg aggcctcggg   4920
cttcgcctcc ggggaggtct ttgactccag cctcccccc acggacgacg aggacttttta   4980
caccaccttt cccctggtca cggaccgcac caccctcctg tcaccccgca aacccgctcc   5040
ccggcccaac ctcaggacag atggggccac gggcgcccct ggggtgctgt ttgccccctc   5100
cgccccggcc cccaacctgc cggcgggcaa aatgaaccac cgagacccgc ttcagccctt   5160
gctggagaac ccgcccttgg ggcccggggc ccccacgtcc tttgagccgc ggaggccccc   5220
tcccctgcgc cccggcgtga cctcagcccc cggcttcccc catctgccca cagccaaccc   5280
```

```
cacagggcct ggggagcggg gcccgccggg cgcagtggag gtgatccggg agtccagcag   5340

caccacgggc atggtggtgg gcattgtggc ggcggcggcg ctctgcatcc tcatcctcct   5400

ctacgccatg tataagtacc gcaatcgtga tgagggctcc taccaggtgg accagagccg   5460

aaactacatc agtaactcgg cccagagcaa tggggcggtg gtgaaagaga aggccccggc   5520

tgcccccaag acgcccagca aggccaagaa gaacaaagac aaggagtatt atgtctgagc   5580

ccccggcact gcgccccact gccagctgcc cctcctggga gggcccggga ggagggtgcc   5640

accctctccc tgccaggggc ctggggaccc tctccctggc tgcctcaggc ttctcttacg   5700

aagaggaaac gcaaaaaaag aaaaggaaaa accccgtgct cgcccccttc ctcctgccgt   5760

ccactgcgcg gcctcgtcag tcccggggct gactgtccct ctcagctctg cgcctgccag   5820

gcagggcacg tgctcacagc cctgggttga tttatttttt taagggggta gttttatttt   5880

ggtggggttg ggtgggaagg aaggctgggg gttttgtaaa gtgtccactg ctcgtcctgt   5940

taattttcct caatttttct tcttcttcct tctgtccctc ctgccttcct tctcttccca   6000

agccctccaa tccccatccc aggcttgctg tgtctcactg tccccaccct ccttccctac   6060

ttcttttttt gtgtgtctgg tttctccctt cctttcctcc ctttgggttt ccagagtcgg   6120

tgggagaagg gcgggagggt gggcccgagt ggcccagtgg gtgggtgggg tggggtgggg   6180

caagtgcccc aactcccctc accaggagag gcacctgctt ggtgccgccc agggaagggg   6240

ctcaggcctg acggaaggcc tgttctgtgt gtgccgccgg gcgacgtgca ttgatgggga   6300

agctgctgga ggagcagggg tggggggtgg gagggagggg aaaggcaaat gcagatatat   6360

attacagaca aatactctag attccacgag cagcagcctg tggcacccgc tgggcgcggg   6420

cagcagggaa gagggagcaa ggcattgtcc acagactgct ggggtcactt ctttgcccac   6480

gggctccctg ctcccccagt tttttttctc tctttgttaa caaatgtgtc tgagtcttgg   6540

aaaacacccc aaccccggaa atgtgtggga aaaagaaaac aaaaactttc caaattccaa   6600

aaaaaaaaaa aaaaaa                                                   6616
```

<210> SEQ ID NO 10
<211> LENGTH: 6390
<212> TYPE: DNA
<213> ORGANISM: Homo sapiens

<400> SEQUENCE: 10

```
tgcagggatg cggcggcggg agcagccgcc ctgactcgcg gagcatcctc ctcggagagg     60

caccgcggcg gggcgggcgg ggagagaggc gcgaggcggc agacaccgct agccctggct    120

ctgccacccg tcggagacgg ggcggccctg tagctctgct acccaccctc cagcttctgg    180

cgccccgaga accaggcatc cctccctgct cttctgtcgg agcccgcggc gggggagggg    240

cgccgccgcc gccgcctgag ggaagccggc atctgggcct ctgcgcgcct cgccccgcgg    300

ccgggcccat ggcactgtga gcctgcaagg gagccccgct cagcgcgggg agcgcccggc    360

cccctcccgc cccatgcgcc cgcggctctg aagcctgagc gggggccggg ggccgggcgg    420

ggccggggcc gccgtaggca tggcgtccgg gagccggtgg cggccgacac cgccgccgct    480

gctgttgctg ctgctgctgg cgctggcggc gcgcgcggac ggcctggagt tcggcggcgg    540

ccccgggcag tgggctcgct acgcgcgctg ggcgggcgcg gcgagcagcg gcgagctcag    600

cttcagcctg cgcaccaacg ccacgcgcgc gctgctgctc tacctggacg acggcggcga    660

ctgcgacttc ctggagctgc tgctggtgga cggccgcctg cggctgcgct tcacgctttc    720

gtgcgccgag ccggccacgc tgcagctgga cacgccggtg gccgacgacc gctggcacat    780
```

-continued

```
ggtgctgctg acccgcgacg cgcgccgcac ggcgctggcg gtggacggcg aggcccgcgc    840
cgccgaggtg cgctccaagc ggcgcgagat gcaggtggcc agcgacctgt tcgtgggcgg    900
catcccgccc gacgtgcgcc tctcggcgct tacgctgagc accgtcaagt acgagccgcc    960
cttccgcggc ctcttggcca acctgaagct gggcgagcgg ccccccgcgc tgctgggcag   1020
ccagggcctg cgcggcgcca ccgccgaccc gctgtgcgcg cccgcgcgca acccctgcgc   1080
caacggcggc ctctgcaccg tgctggcccc cggcgaggtg ggctgcgact gcagccacac   1140
gggcttcggc ggcaagttct gcagcgaaga ggagcacccc atggaaggtc cggctcacct   1200
gacgttaaac agcgaaggca aggaggagtt tgtggcgacc ttcaaaggca atgagttctt   1260
ctgctacgac ctgtcacaca accccatcca gagcagcact gatgagatca cactggcctt   1320
ccgcaccctg caacgcaacg gcctgatgct gcatacaggc aagtcggccg actacgtcaa   1380
cctgtccctc aagtctgggg ctgtctggct ggtcatcaac ctaggctcag gtgccttcga   1440
ggcccttgtg gaacccgtca atggcaagtt caacgacaac gcctggcacg acgtccgggt   1500
cacccgaaac ctgcgccagc acgcagggat tggacacgct atggtgacca tctcggtgga   1560
cgggatcctg accaccacag gctacacgca ggaggattac accatgctgg gctctgatga   1620
cttcttctac attgggggca gccccaacac agctgacctg ccgggctcgc ccgtcagcaa   1680
caacttcatg ggctgcctca aggacgtggt ctataagaac aatgacttca aattggaact   1740
atcccgcctg gcaaaggaag gggaccccaa gatgaagctg caggggggact tgtcattccg   1800
ctgtgaggat gtggctgccc tggaccctgt gacctttgag agtcccgagg cctttgtggc   1860
gctgccccgc tggagcgcta agcgcactgg ctccatctcc ctagacttcc gcaccaccga   1920
gcccaatggg ctgctgctct tcagccaggg ccggcgggct gggggtggag ctggcagcca   1980
cagctctgct cagcgggccg actactttgc catggagcta ttggacggcc acctctatct   2040
tctgctggac atgggatctg gggcatcaa gctgcgggca tccagccgca aggtcaatga   2100
tggcgagtgg tgtcacgtgg acttccagag ggatgggcga aaaggctcca tctcagtgaa   2160
tagtcgcagc acgccgttct tggccactgg agacagcgag attctggacc tggagagtga   2220
gctgtacctg ggcggtctcc ctgagggggg ccgggtggac ctgcccctgc cccagaggt   2280
gtggacagca gcactccggg caggctacgt gggctgtgtg cgggacctct tcatagatgg   2340
gcgtagccga gacctccggg gcctggctga ggctcagggg gctgtgggcg ttgcccccctt   2400
ttgctcccgg gagacgctga agcagtgtgc atctgccccc tgtcgcaatg gggcgtctg    2460
tcgagaaggc tggaaccgct tcatctgtga ctgcatcggg accggctttc ttgggcgggt   2520
ctgtgagaga gaggccacgg tcctgagcta cgatggctcc atgtacatga agatcatgct   2580
gcctaacgcc atgcacacgg aggcagagga tgtgtccctg cgtttcatgt cccagcgggc   2640
ctacggactc atgatggcca ccacttccag ggagtctgcc gacaccctac gcctggagct   2700
ggatgggggg cagatgaagc tcactgtcaa cctcggtaaa ggccccgaaa cgctgtttgc   2760
ggggcacaag ctcaatgaca atgagtggca cacggtgagg gtggtccggc gtggcaagag   2820
cctgcagctg tctgtggaca acgtgactgt ggagggacag atggcaggag cccatatgcg   2880
gctggagttc cacaacattg agacgggcat catgacggag cggcggttta tctccgtggt   2940
gccctccaac ttcatcgggc atctgagtgg gctcgtgttc aatggccagc cctacatgga   3000
ccagtgcaag gatggtgaca tcacctactg tgagctcaat gctcgctttg gcctgcgtgc   3060
catcgtggcc gatcccgtca ccttcaagag tcgcagcagc tacctggcac tcgccacgct   3120
ccaagcctat gcttccatgc acctcttctt ccagttcaag accacggccc ctgatgggct   3180
```

```
tcttctgttc aactcgggca acggcaatga cttcattgtc atcgagctgg tcaaggggta   3240
catccactac gtgtttgacc tggggaatgg cccgtccttg atgaagggga actcagacaa   3300
accagtcaat gacaaccagt ggcacaacgt ggtggtgtcc agggacccag gcaacgtgca   3360
cacgctcaag attgactccc gcactgtcac gcagcactcc aatggcgccc gaaacctcga   3420
tctcaaaggg gagttgtaca ttggcggtct gagcaagaat atgttcagca acctgcccaa   3480
gctggtggcc tcccgggatg gctttcaggg ctgcctggcc tcagtggacc tcaacggacg   3540
tctcccagac ctcatcgccg acgccctgca ccgcattggg caggtggaga ggggctgtga   3600
tggccccagc accacctgca ctgaagagtc ctgtgccaac cagggcgtct gcttgcagca   3660
gtgggatggc ttcacctgcg actgcaccat gacttcctat ggaggccctg tctgcaatga   3720
tcccgggacc acatacatct ttgggaaggg gggagcgctc atcacctaca cgtggccccc   3780
caatgacagg cccagcacga ggatggatcg cctggccgtg ggcttcagca cccaccagcg   3840
gagcgctgtg ctggtgcggg tggacagcgc ctccggcctt ggagactacc tgcagctgca   3900
catcgaccag ggcaccgtgg gggtgatctt taacgtgggc acggacgaca ttaccatcga   3960
cgagcccaac gccatagtaa gcgacggcaa ataccacgtg gtgcgcttca ctcgaagcgg   4020
cggcaacgcc accctgcagg tggacagctg gccggtcaac gagcggtacc cggcaggccg   4080
ccagctgacc atcttcaaca gccaggctgc catcaagatc gggggccggg atcagggccg   4140
ccccttccag ggccaggtgt ccggcctcta ctacaatggg ctcaaggtgc tggcgctggc   4200
cgccgagagc gaccccaatg tgcggactga gggtcacctg cgcctggtgg gggaggggcc   4260
gtccgtgctg ctcagtgcgg agaccacggc caccaccctg ctggctgaca tggccaccac   4320
catcatggag actaccacca ccatggccac taccaccacg cgccggggcc gctcccccac   4380
actgagggac agcaccaccc agaacacaga tgacctgctg gtggcctctg ctgagtgtcc   4440
aagcgatgat gaggacctgg aggagtgtga gcccagtact ggaggagagt taatattgcc   4500
cattatcacg gaggactcct tagacccccc tcccgtggcc acccgatccc ccttcgtgcc   4560
cccgcccccct accttctacc ccttcctcac gggagtgggc gccacccaag acacgctgcc   4620
cccgcccgcc gcgcgccgcc cgccctctgg gggcccgtgc caggccgagc gggacgacag   4680
cgactgcgag gagcccatcg aggcctcggg cttcgcctcc ggggaggtct ttgactccag   4740
cctcccccccc acggacgacg aggactttta caccaccttt cccctggtca cggaccgcac   4800
caccctcctg tcaccccgca aacccgctcc ccggcccaac ctcaggacag atggggccac   4860
gggcgcccct ggggtgctgt ttgcccccctc cgccccggcc cccaacctgc cggcgggcaa   4920
aatgaaccac cgagacccgc ttcagccctt gctggagaac ccgcccttgg ggcccggggc   4980
ccccacgtcc tttgagccgc ggaggccccc tcccctgcgc cccggcgtga cctcagcccc   5040
cggcttcccc catctgccca cagccaaccc cacagggcct ggggagcggg gcccgccggg   5100
cgcagtggag gtgatccggg agtccagcag caccacgggc atggtggtgg gcattgtggc   5160
ggcggcggcg ctctgcatcc tcatcctcct ctacgccatg tataagtacc gcaatcgtga   5220
tgagggctcc taccaggtgg accagagccg aaactacatc agtaactcgg cccagagcaa   5280
tggggcggtg gtgaaagaga aggccccggc tgcccccaag acgcccagca aggccaagaa   5340
gaacaaagac aaggagtatt atgtctgagc ccccggcact gcgccccact gccagctgcc   5400
cctcctggga gggcccggga ggagggtgcc accctctccc tgccaggggc ctggggaccc   5460
tctccctggc tgcctcaggc ttctcttacg aagaggaaac gcaaaaaaag aaaaggaaaa   5520
accccgtgct cgcccccttc ctcctgccgt ccactgcgcg gcctcgtcag tcccggggct   5580
```

```
gactgtccct ctcagctctg cgcctgccag gcagggcacg tgctcacagc cctgggttga   5640

tttatttttt taagggggta gttttatttt ggtggggttg ggtgggaagg aaggctgggg   5700

gttttgtaaa gtgtccactg ctcgtcctgt taattttcct caatttttct tcttcttcct   5760

tctgtccctc ctgccttcct tctcttccca agccctccaa tccccatccc aggcttgctg   5820

tgtctcactg tccccaccct ccttccctac ttcttttttt gtgtgtctgg tttctccctt   5880

cctttcctcc ctttgggttt ccagagtcgg tgggagaagg gcgggagggt gggcccgagt   5940

ggcccagtgg gtgggtgggg tggggtgggg caagtgcccc aactcccctc accaggagag   6000

gcacctgctt ggtgccgccc agggaagggg ctcaggcctg acggaaggcc tgttctgtgt   6060

gtgccgccgg gcgacgtgca ttgatgggga agctgctgga ggagcagggg tgggggggtgg   6120

gagggagggg aaaggcaaat gcagatatat attacagaca aatactctag attccacgag   6180

cagcagcctg tggcacccgc tgggcgcggg cagcagggaa gaggggagcaa ggcattgtcc   6240

acagactgct ggggtcactt ctttgcccac gggctccctg ctcccccagt tttttttctc   6300

tctttgttaa caaatgtgtc tgagtcttgg aaaacacccc aaccccggaa atgtgtggga   6360

aaaagaaaac aaaaactttc caaattccaa                                    6390
```

<210> SEQ ID NO 11
<211> LENGTH: 3550
<212> TYPE: DNA
<213> ORGANISM: Homo sapiens

<400> SEQUENCE: 11

```
ggcagcagcg gcgcggccgg ccccagtcgc cgtcggtctc ccgccttcgg gggaaccagg     60

tctccgtccc tcttctctcc tccagcccgc accgccccgc tccccagctc ggtttttccg    120

caggatttcc ctcgctctcc cctccctgct tggcccccgc gctcccctcc ctctccactc    180

ggcaccatgc cccctccccc gggcgctccc ccgggtttct gacggccctc tgcgccgctc    240

cgaccccgcc gggatgcaga gagaccccta gctcctcgcg atggacccag gcatcctgga    300

ccttggcgtt gccgctccgc ggacccccga tttcccggcg ggatccagtt gattttgttg    360

gctccggacc gaggcttggg ccctggttta cctccgcttc atccctaccc cgctcccgga    420

gctcggagcc ggaggggggc ttcgcggggt gcgcagcccc gcgtccccgc ccccggccat    480

ggggctgtga ggcggtcgcc cccgggccga aatgcccccc ggggggagcg ggccgggggg    540

gtgcccgcgc cgccccccgg ccctggctgg gcccctgccg ccgcctccac cgccgccgcc    600

gccacctctg ctgccgctgt tgccgctgtt gctgctgttg ctgctggggg cggccgaggg    660

ggcccgggtc tcctccagcc tcagcaccac ccaccacgtc caccacttcc acagcaagca    720

cggcaccgtg cccatcgcca tcaaccgcat gcccttcctc acccgcggcg gccacgccgg    780

gaccacatac atctttggga agggggggagc gctcatcacc tacacgtggc cccccaatga    840

caggcccagc acgaggatgg atcgcctggc cgtgggcttc agcacccacc agcggagcgc    900

tgtgctggtg cgggtggaca gcgcctccgg ccttggagac tacctgcagc tgcacatcga    960

ccagggcacc gtgggggtga tctttaacgt gggcacggac gacattacca tcgacgagcc   1020

caacgccata gtaagcgacg gcaaatacca cgtggtgcgc ttcactcgaa gcggcggcaa   1080

cgccaccctg caggtggaca gctggccggt caacgagcgg tacccggcag gaaactttga   1140

taacgagcgc ctggcgattg ctagacagag aatcccctac cggcttggtc gagtagtaga   1200

tgagtggctg ctcgacaaag gccgccagct gaccatcttc aacagccagg ctgccatcaa   1260

gatcgggggc cgggatcagg gccgcccctt ccagggccag gtgtccggcc tctactacaa   1320
```

```
tgggctcaag gtgctggcgc tggccgccga gagcgacccc aatgtgcgga ctgagggtca   1380
cctgcgcctg gtgggggagg ggccgtccgt gctgctcagt gcggagacca cggccaccac   1440
cctgctggct gacatggcca ccaccatcat ggagactacc accaccatgg ccactaccac   1500
cacgcgccgg ggccgctccc ccacactgag ggacagcacc acccagaaca cagatgacct   1560
gctggtggcc tctgctgagt gtccaagcga tgatgaggac ctggaggagt gtgagcccag   1620
tactggagga gagttaatat tgcccattat cacggaggac tccttagacc cccctcccgt   1680
ggccacccga tccccccttcg tgcccccgcc ccctaccttc taccccttcc tcacgggagt   1740
gggcgccacc caagacacgc tgcccccgcc cgccgcgcgc cgcccgccct ctgggggccc   1800
gtgccaggcc gagcgggacg acagcgactg cgaggagccc atcgaggcct cgggcttcgc   1860
ctccggggag gtctttgact ccagcctccc ccccacggac gacgaggact tttacaccac   1920
ctttcccctg gtcacggacc gcaccaccct cctgtcaccc cgcaaacccg ctccccggcc   1980
caacctcagg acagatgggg ccacgggcgc ccctggggtg ctgtttgccc cctccgcccc   2040
ggcccccaac ctgccggcgg gaaaaatgaa ccaccgagac ccgcttcagc ccttgctgga   2100
gaacccgccc ttggggcccg gggcccccac gtcctttgag ccgcggaggc cccctcccct   2160
gcgccccggc gtgacctcag cccccggctt cccccatctg cccacagcca accccacagg   2220
gcctggggag cggggcccgc cgggcgcagt ggaggtgatc cgggagtcca gcagcaccac   2280
gggcatggtg gtgggcattg tggcggcggc ggcgctctgc atcctcatcc tcctctacgc   2340
catgtataag taccgcaatc gtgatgaggg ctcctaccag gtggaccaga gccgaaacta   2400
catcagtaac tcggcccaga gcaatggggc ggtggtgaaa gagaaggccc cggctgcccc   2460
caagacgccc agcaaggcca agaagaacaa agacaaggag tattatgtct gagcccccgg   2520
cactgcgccc cactgccagc tgcccctcct gggagggccc gggaggaggg tgccaccctc   2580
tccctgccag gggcctgggg accctctccc tggctgcctc aggcttctct tacgaagagg   2640
aaacgcaaaa aaagaaaagg aaaaaccccg tgctcgcccc cttcctcctg ccgtccactg   2700
cgcggcctcg tcagtcccgg ggctgactgt ccctctcagc tctgcgcctg ccaggcaggg   2760
cacgtgctca cagccctggg ttgatttatt tttttaaggg ggtagtttta ttttggtggg   2820
gttgggtggg aaggaaggct gggggttttg taaagtgtcc actgctcgtc ctgttaattt   2880
tcctcaattt ttcttcttct tccttctgtc cctcctgcct tccttctctt cccaagccct   2940
ccaatcccca tcccaggctt gctgtgtctc actgtcccca ccctccttcc ctacttcttt   3000
ttttgtgtgt ctggtttctc ccttcctttc ctccctttgg gtttccagag tcggtgggag   3060
aagggcggga gggtgggccc gagtggccca gtgggtgggt ggggtggggt ggggcaagtg   3120
ccccaactcc cctcaccagg agaggcacct gcttggtgcc gcccagggaa ggggctcagg   3180
cctgacggaa ggcctgttct gtgtgtgccg ccgggcgacg tgcattgatg gggaagctgc   3240
tggaggagca ggggtggggg gtgggaggga ggggaaaggc aaatgcagat atatattaca   3300
gacaaatact ctagattcca cgagcagcag cctgtggcac ccgctgggcg cgggcagcag   3360
ggaagaggga gcaaggcatt gtccacagac tgctggggtc acttctttgc ccacgggctc   3420
cctgctcccc cagttttttt tctctctttg ttaacaaatg tgtctgagtc ttggaaaaca   3480
ccccaacccc ggaaatgtgt gggaaaaaga aaacaaaaac tttccaaatt ccaaaaaaaa   3540
aaaaaaaaaa                                                          3550
```

<210> SEQ ID NO 12
<211> LENGTH: 6163

<212> TYPE: DNA
<213> ORGANISM: Homo sapiens

<400> SEQUENCE: 12

```
caggactgga gggcttgagg aatgtggtgg tccctctctt cgttgtttct gccccctgag     60
gttgtgcttt ctcagggata tgcactctgc acttccattc ctgcagtgaa attaactcga    120
gcttggcagc tcgagaggag aatgtggcca ctttccgagg ctcagagtat ctgtgctacg    180
acctgtctca gaacccgatc cagagcagca gtgatgaaat caccctctcc tttaagacct    240
ggcagcgtaa cggcctcatc ctgcacacgg gcaagtcggc tgactatgtc aacctggctc    300
tgaaggatgg tgcggtctcc ttggtcatta acctggggtc cggggccttt gaggccattg    360
tggagccagt gaatggaaaa ttcaacgaca acgcctggca tgatgtcaaa gtgacacgca    420
acctccggca ggtgacaatc tctgtggatg gcattcttac cacgacgggc tacactcaag    480
aggactatac catgctgggc tcggacgact tcttctatgt aggaggaagc ccaagtaccg    540
ctgacttgcc tggctcccct gtcagcaaca acttcatggg ctgccttaaa gaggttgttt    600
ataagaataa tgacatccgt ctggagctgt ctcgcctggc ccggattgcg gacaccaaga    660
tgaaaatcta tggcgaagtt gtgtttaagt gtgagaatgt ggccacactg gaccccatca    720
actttgagac cccagaggct tacatcagct tgcccaagtg gaacactaaa cgtatgggct    780
ccatctcctt tgacttccgc accacagagc ccaatggcct gatcctcttc actcatggaa    840
agccccaaga gaggaaggat gctcggagcc agaagaatac aaaagtagac ttctttgccg    900
tggaactcct cgatggcaac ctgtacttgc tgcttgacat gggctctggc accatcaaag    960
tgaaagccac tcagaagaaa gccaatgatg gggaatggta ccatgtggac attcagcgag   1020
atggcagatc aggtactata tcagtgaaca gcaggcgcac gccattcacc gccagtgggg   1080
agagcgagat cctggacctg gaaggagaca tgtacctggg agggctgccg gagaaccgtg   1140
ctggccttat tctccccacc gagctgtgga ctgccatgct caactatggc tacgtgggct   1200
gcatccgcga cctattcatt gatgggcgca gcaagaacat tcgacagctg gcagagatgc   1260
agaatgctgc gggtgtcaag tcctcctgtt cacggatgag tgccaagcag tgtgacagct   1320
acccctgcaa gaataatgct gtgtgcaagg acggctggaa ccgcttcatc tgcgactgca   1380
ccggcaccgg atactgggga agaacctgcg aaagggaggc atccatcctg agctatgatg   1440
gtagcatgta catgaagatc atcatgccca tggtcatgca tactgaggca gaggatgtgt   1500
ccttccgctt catgtcccag cgagcttatg gctgctggt ggctacgacc tccagggact   1560
ctgccgacac cctgcgtctg gagctggatg gggggcgtgt caagctcatg gttaacttag   1620
actgtatcag gataaactgt aactccagca aaggaccaga gaccttgtat gcagggcaga   1680
agctcaatga caacgagtgg cacaccgttc gggtggtgcg gagaggaaaa agccttaagt   1740
taaccgtgga tgatgatgtg gctgagggta caatggtggg agaccatacc cgtttggagt   1800
tccacaacat tgaaacggga atcatgactg agaaacgcta catctccgtt gtcccctcca   1860
gctttattgg ccatctgcag agcctcatgt ttaatggcct tctctacatt gacttgtgca   1920
aaaatggtga cattgattat tgtgagctga aggctcgttt tggactgagg aacatcatcg   1980
ctgaccctgt cacctttaag accaagagca gctacctgag ccttgccact cttcaggctt   2040
acacctccat gcacctcttc ttccagttca agaccacctc accagatggc ttcattctct   2100
tcaatagtgg tgatggcaat gacttcattg cagtcgagct tgtcaagggg tatatacact   2160
acgtttttga cctcggaaac ggtcccaatg tgatcaaagg caacagtgac cgcccccctga   2220
atgacaacca gtggcacaat gtcgtcatca ctcgggacaa tagtaacact catagcctga   2280
```

```
aagtggacac caaagtggtc actcaggtta tcaatggtgc caaaaatctg gatttgaaag   2340
gtgatctcta tatggctggt ctggcccaag gcatgtacag caacctccca aagctcgtgg   2400
cctctcgaga tggctttcag ggctgtctag catcagtgga cttgaatgga cgcctgccag   2460
acctcatcaa tgatgctctt catcggagcg gacagatcga gcgtggctgt gaaggaccca   2520
gtaccacctg ccaggaagat tcatgtgcca accagggggt ctgcatgcaa caatgggagg   2580
gcttcacctg tgattgttct atgacctctt attctggaaa ccagtgcaat gatcctggcg   2640
ctacgtacat ctttgggaaa agtggtgggc ttatcctcta cacctggcca gccaatgaca   2700
ggcccagcac gcggtctgac cgccttgccg tgggcttcag caccactgtg aaggatggca   2760
tcttggtccg catcgacagt gctccaggac ttggtgactt cctccagctt cacatagaac   2820
aggggaaaat tggagttgtc ttcaacattg gcacagttga catctccatc aaagaggaga   2880
gaacccctgt aaatgacggc aaataccatg tggtacgctt caccaggaac ggcggcaacg   2940
ccaccctgca ggtggacaac tggccagtga atgaacatta tcctacaggc cggcagttaa   3000
ccatcttcaa cactcaggcg caaatagcca ttggtggaaa ggacaaagga cgcctcttcc   3060
aaggccaact ctctgggctc tattatgatg gtttgaaagt actgaacatg gcggctgaga   3120
acaaccccaa tattaaaatc aatggaagtg ttcggctggt tggagaagtc ccatcaattt   3180
tgggaacaac acagacgacc tccatgccac cagaaatgtc tactactgtc atggaaacca   3240
ctactacaat ggcgactacc acaacccgta agaatcgctc tacagccagc attcagccaa   3300
catcagatga tcttgtttca tctgctgaat gttcaagtga tgatgaagac tttgttgaat   3360
gtgagccgag tacagcaaac cccacggagc cgggaatcag acgggttccg ggggcctcag   3420
aggtgatccg ggagtcgagc agcacaacag ggatggtcgt cggcattgtg gctgctgccg   3480
ccctctgcat cttgatcctc ctgtacgcca tgtacaagta caggaacagg gacgaggggt   3540
cctatcaagt ggacgagacg cggaactaca tcagcaactc cgcccagagc aacggcacgc   3600
tcatgaagga gaagcagcag agctcgaaga gcggccacaa gaaacagaaa aacaaggaca   3660
gggagtatta cgtgtaaaca tgcgaacact gctcacacgc gagttttcac agttatttct   3720
atccacgcct atgaatcttt ggacggtgag atctcacaga tgtcagaact gctggaacta   3780
tgaaatgggg tatataacca cgactctggt ggggaaaacc gttttttaaa ggacacacac   3840
acacacagcg atgcatctct ctctaaagct cagccacggc tgcggcaagg tcccagcggt   3900
cgctgggaga cagaaggttt tgtgccctgc tgtatcataa agcacacact tagcgctctg   3960
gagccggacg gtggctccac cacttccgca ggcctggaaa cttccttctc cggaggacct   4020
tttactaaaa ggtagaagac ttcatggctt acttgttcca taactccaag tgagtctgta   4080
atgtttgtga agcttgactg taaccatgtt ttttctgttt aattatgtaa aaaacaaaac   4140
tacaacaaca aaaaaagaaa aaagttaaaa aagaaaaaaa caccaaaaaa caaaaacaaa   4200
caaaaaaaaa aacccacaac ccttatctgg ttctgaccag tgtgcgtgta actttatgat   4260
ctgaggggaa aaatggcttt tgggtttttg tttatttttt tgataatgac tggacatcag   4320
aagaggaaaa aaactcaaaa caaaagcgag agagactatt gccatatgaa ctcaaaagct   4380
atcatggtgt tcactctaca tatcaggtta tggtgtctct agaatctgtt gtttgtttcc   4440
tataagatgc tttgctgaac acatagcaaa attcatgtga cggatgataa attgattcga   4500
aaagctggtc ccccaggatc taatttcaga atttaccacc caaacccgga acagatgggt   4560
ttagggctgg tgttatcaga gctattggct ttacgtaaca atattgttcc tgtccattca   4620
cccagccaaa ttgtgttaaa gaggaaagcc ccacaaacta aaacagcctt tcctagggaa   4680
```

-continued

```
gaggaagggg aggtgggctg gatctgtgac tgattgaaat gcatgcaaat aaaaaagaca   4740
atattaaagt ctgttatcaa accagacagt aggggagttc aactcgtgat ggaaccacaa   4800
aaggtcacac aagccaacca tgtcatgcca gagtacaaaa cacatagttc tttccccgcc   4860
ccgaatgtga caatggtttt catagtggtt taattttgta gcctgacatt tatggataac   4920
tctgtccttc catttgctca cttctctctt cacccatctt ttttaaaaac aaataaatga   4980
ataaagctgc tgtgacacac acacaaaagg aatttaatag tataatatat atataaataa   5040
atatatatac agatatattt atcatggtat gtttgatggg atgactgaca caggaaatct   5100
gttaaagtct taaaatggaa tgagaatgtt gttttaaaag aaaatagcaa aacaacaaaa   5160
aagcaaacct taaaatgtga agaaagtgtg aattttagtt ttgtcacagt taactgtgtc   5220
aaagagaatt aaaaaaaaaa acttcagatt ttgtttacat attttactac atttttgctg   5280
gtataattcc ttagccacct atgtacatac tgctttaaga aatgtttttt tcctgtttat   5340
ttctgtttgg tttatattct ggttgtcttt ttctttttgt aaagaggaaa caatgtacag   5400
aaaaacaata aactggttgt atggccatag ctatccgaaa agcaagagac aaagcaagac   5460
aaatattcac acaaaaatga agtgtgtcct ctggagggtc agatatacaa tttcttttgt   5520
acagatgaaa atcaatcagc tgcttagatt tagaaatcta ctcttgctgg tctttgtaag   5580
ttgcatgaat atttgacttt gaaaaaatat cttaacgaca tggggcaaaa agtgcaatct   5640
aaatggtagc ctttactaat gtgtgtggaa agaggtgttc ctcattatct aatatttcaa   5700
tgtgttaaga gtttaatttt tttgttatca ttaaaaaaga caggattata aagagatatc   5760
aaagcacgat tttagataac ctaaacggcc cagcctatac gaagttgatt atatctcgat   5820
gtctgtaaaa gattgctgtt cttggagtct tgaggtcttg tgaattgatt tcctgctttc   5880
tttcattttt ttcaatttaa gtaataatac atttgttata ttcctttcag tgtaagtttc   5940
tatttggaca attttatggg aacatgtgca ttctctatgt gagcttctat catattcctg   6000
ttttattagc agaacctaaa ggaatttatt taatgatgtt gtgacattac tgctttttct   6060
tttttctttt cttagttcat atttgcattt tcgttcaagg atatgcttag caataaaatg   6120
ttcttcccaa aaaaaaaaaa aaaaaaaaaa aaaaaaaaaa aaa                     6163
```

<210> SEQ ID NO 13
<211> LENGTH: 4766
<212> TYPE: DNA
<213> ORGANISM: Homo sapiens

<400> SEQUENCE: 13

```
gatttgctct cgggagtgcg ctatttgcat atgacttgcc catttgtgaa tttggctccc     60
caactcctcg cttcacttca cctgtgcctc cctggtccgc gcacttcgca ggcgcccgcc    120
cgcctctcgg ccacctctgc agcctgccag gcacctcctc ttgcgctctc gctgatttcg    180
cccacccacc tccctccacc ccgtgccacg ttggtttggg tggctgctcc gcaccgggtt    240
cctcctcctc tcctctttcc ctccagtcct tcttattctc ttcctctggc tgcggtggct    300
gctgctgctg ctggttttca tccagttggg aaacccagga agccggcggc tgctccgtgg    360
cgctagtcca gcacgcccag ggttaaaagc ctcgcgccct tccgcggaga ctcccaggaa    420
cacccgaaga actcttccac ctgcagcccc cttttgcctg gcagttctgc attgcatctc    480
atggaagtgg aaacaggaaa ataaaaatgt tcaaactcct tggatgttgg gataaactca    540
cctgaaccca cttgggttcg ggctgcctcc ttctcttcct tcattgccac ctttcctctg    600
tgtggctccc gggagtgtgc ggttaagtca tcagactcga agtgcctaga gatccggagg    660
```

```
aagccgcgcc ggtcttcccc tgacatgcgt ggcatgccgg ggctccgtag gaggtttgct    720
atacctggga ggaccctggc attctaaatt tcagctccgg gaaagagaag ggctttttg    780
ccttttatct ttttttttc tttctttaag tagtaatttt ttaactgatt cattgtttgg    840
aaagcgcata ttgcttccct cttccccgaa ttctggcaac tcttcctcct gctatgatgg    900
gcccttgggc atcatgaact tcattactcc tcactggctg gaattcaaac tgcccatctg    960
tagtggtccc gtgcgttgac catgcacctg agaatccacg cgagacggag ccctcctcgc   1020
cggccggcct ggacgcttgg gatctggttc ctgttctggg gatgtatcgt cagctctgta   1080
tggagttctt ctaatgtagc ttcctcctcc tccacctctt cctcgccggg gtctcactct   1140
cagcacgagc accatttcca tggcagcaag catcactcag tgcctatttc tatctatcgt   1200
tcccctgttt cccttcgagg aggacacgct ggcgctacgt acatctttgg gaaaagtggt   1260
gggcttatcc tctacacctg gccagccaat gacaggccca gcacgcggtc tgaccgcctt   1320
gccgtgggct tcagcaccac tgtgaaggat ggcatcttgg tccgcatcga cagtgctcca   1380
ggacttggtg acttcctcca gcttcacata gaacagggga aaattggagt tgtcttcaac   1440
attggcacag ttgacatctc catcaaagag gagagaaccc ctgtaaatga cggcaaatac   1500
catgtggtac gcttcaccag gaacggcggc aacgccaccc tgcaggtgga caactggcca   1560
gtgaatgaac attatcctac aggccggcag ttaaccatct tcaacactca ggcgcaaata   1620
gccattggtg gaaaggacaa aggacgcctc ttccaaggcc aactctctgg gctctattat   1680
gatggtttga aagtactgaa catggcggct gagaacaacc ccaatattaa aatcaatgga   1740
agtgttcggc tggttggaga agtcccatca attttgggaa caacacagac gacctccatg   1800
ccaccagaaa tgtctactac tgtcatggaa accactacta caatggcgac taccacaacc   1860
cgtaagaatc gctctacagc cagcattcag ccaacatcag atgatcttgt ttcatctgct   1920
gaatgttcaa gtgatgatga agactttgtt gaatgtgagc cgagtacagg taggtcagca   1980
aaccccacgg agccgggaat cagacgggtt ccgggggcct cagaggtgat ccgggagtcg   2040
agcagcacaa cagggatggt cgtcggcatt gtggctgctg ccgccctctg catcttgatc   2100
ctcctgtacg ccatgtacaa gtacaggaac agggacgagg ggtcctatca agtggacgag   2160
acgcggaact acatcagcaa ctccgcccag agcaacggca cgctcatgaa ggagaagcag   2220
cagagctcga agagcggcca caagaaacag aaaaacaagg acagggagta ttacgtgtaa   2280
acatgcgaac actgctcaca cgcgagtttt cacagttatt tctatccacg cctatgaatc   2340
tttggacggt gagatctcac agatgtcaga actgctggaa ctatgaaatg gggtatataa   2400
ccacgactct ggtggggaaa accgtttttt aaaggacaca cacacacaca gcgatgcatc   2460
tctctctaaa gctcagccac ggctgcggca aggtcccagc ggtcgctggg agacagaagg   2520
ttttgtgccc tgctgtatca taaagcacac acttagcgct ctggagccgg acggtggctc   2580
caccacttcc gcaggcctgg aaacttcctt ctccggagga ccttttacta aaaggtagaa   2640
gacttcatgg cttacttgtt ccataactcc aagtgagtct gtaatgtttg tgaagcttga   2700
ctgtaaccat gttttttctg tttaattatg taaaaaacaa aactacaaca acaaaaaaag   2760
aaaaaagtta aaaaagaaaa aaacaccaaa aaacaaaaac aaacaaaaaa aaaaacccac   2820
aaccccttatc tggttctgac cagtgtgcgt gtaactttat gatctgaggg gaaaaatggc   2880
ttttgggttt ttgtttattt ttttgataat gactggacat cagaagagga aaaaaactca   2940
aaacaaaagc gagagagact attgccatat gaactcaaaa gctatcatgg tgttcactct   3000
acatatcagg ttatggtgtc tctagaatct gttgtttgtt tcctataaga tgctttgctg   3060
```

```
aacacatagc aaaattcatg tgacggatga taaattgatt cgaaaagctg gtcccccagg   3120
atctaatttc agaatttacc acccaaaccc ggaacagatg ggtttagggc tggtgttatc   3180
agagctattg gctttacgta acaatattgt tcctgtccat tcacccagcc aaattgtgtt   3240
aaagaggaaa gccccacaaa ctaaaacagc ctttcctagg gaagaggaag gggaggtggg   3300
ctggatctgt gactgattga aatgcatgca aataaaaaag acaatattaa agtctgttat   3360
caaaccagac agtaggggag ttcaactcgt gatggaacca caaaaggtca cacaagccaa   3420
ccatgtcatg ccagagtaca aaacacatag ttctttcccc gccccgaatg tgacaatggt   3480
tttcatagtg gtttaatttt gtagcctgac atttatggat aactctgtcc ttccatttgc   3540
tcacttctct cttcacccat ctttttaaa aacaaataaa tgaataaagc tgctgtgaca   3600
cacacacaaa aggaatttaa tagtataata tatatataaa taaatatata tacagatata   3660
tttatcatgg tatgtttgat gggatgactg acacaggaaa tctgttaaag tcttaaaatg   3720
gaatgagaat gttgttttaa aagaaaatag caaaacaaca aaaaagcaaa ccttaaaatg   3780
tgaagaaagt gtgaatttta gttttgtcac agttaactgt gtcaaagaga attaaaaaaa   3840
aaaacttcag attttgttta catattttac tacatttttg ctggtataat tccttagcca   3900
cctatgtaca tactgcttta agaaatgttt ttttcctgtt tatttctgtt tggtttatat   3960
tctggttgtc tttttctttt tgtaaagagg aaacaatgta cagaaaaaca ataaactggt   4020
tgtatggcca tagctatccg aaaagcaaga gacaaagcaa gacaaatatt cacacaaaaa   4080
tgaagtgtgt cctctggagg gtcagatata caatttcttt tgtacagatg aaaatcaatc   4140
agctgcttag atttagaaat ctactcttgc tggtctttgt aagttgcatg aatatttgac   4200
tttgaaaaaa tatcttaacg acatggggca aaaagtgcaa tctaaatggt agcctttact   4260
aatgtgtgtg gaaagaggtg ttcctcatta tctaatattt caatgtgtta agagtttaat   4320
tttttgtta tcattaaaaa agacaggatt ataaagagat atcaaagcac gattttagat   4380
aacctaaacg gcccagccta tacgaagttg attatatctc gatgtctgta aaagattgct   4440
gttcttggag tcttgaggtc ttgtgaattg atttcctgct ttctttcatt tttttcaatt   4500
taagtaataa tacatttgtt atattccttt cagtgtaagt ttctatttgg acaattttat   4560
gggaacatgt gcattctcta tgtgagcttc tatcatattc ctgttttatt agcagaacct   4620
aaaggaattt atttaatgat gttgtgacat tactgctttt tcttttttct tttcttagtt   4680
catatttgca ttttcgttca aggatatgct tagcaataaa atgttcttcc caaaaaaaaa   4740
aaaaaaaaaa aaaaaaaaaa aaaaaa                                         4766
```

<210> SEQ ID NO 14
<211> LENGTH: 4324
<212> TYPE: DNA
<213> ORGANISM: Homo sapiens

<400> SEQUENCE: 14

```
ggttgggctc gcggcgctgt gattggtctg cccggactcc gcctccagcg catgtcatta     60
gcatctcatt agctgtccgc tcgggctccg gaggcagcca acgccgccag tctgaggcag    120
gtgcccgaca tggcgagtgt agtgctgccg agcggatccc agtgtgcggc ggcagcggcg    180
gcggcggcgc ctcccgggct ccggctccgg cttctgctgt tgctcttctc cgccgcggca    240
ctgatcccca caggtgatgg gcagaatctg tttacgaaag acgtgacagt gatcgaggga    300
gaggttgcga ccatcagttg ccaagtcaat aagagtgacg actctgtgat tcagctactg    360
aatcccaaca ggcagaccat ttatttcagg gacttcaggc ctttgaagga cagcaggttt    420
```

```
cagttgctga atttttctag cagtgaactc aaagtatcat tgacaaacgt ctcaatttct    480
gatgaaggaa gatacttttg ccagctctat accgatcccc cacaggaaag ttacaccacc    540
atcacagtcc tggtcccacc acgtaatctg atgatcgata tccagaaaga cactgcggtg    600
gaaggtgagg agattgaagt caactgcact gctatggcca gcaagccagc cacgactatc    660
aggtggttca aagggaacac agagctaaaa ggcaaatcgg aggtggaaga gtggtcagac    720
atgtacactg tgaccagtca gctgatgctg aaggtgcaca aggaggacga tggggtccca    780
gtgatctgcc aggtggagca ccctgcggtc actggaaacc tgcagaccca gcggtatcta    840
gaagtacagt ataagcctca agtgcacatt cagatgactt atcctctaca aggcttaacc    900
cgggaagggg acgcgcttga gttaacatgt gaagccatcg ggaagcccca gcctgtgatg    960
gtaacttggg tgagagtcga tgatgaaatg cctcaacacg ccgtactgtc tgggcccaac   1020
ctgttcatca ataacctaaa caaaacagat aatggtacat accgctgtga agcttcaaac   1080
atagtgggga aagctcactc ggattatatg ctgtatgtat acgatccccc cacaactatc   1140
cctcctccca caacaaccac caccaccacc accaccacca ccaccaccat ccttaccatc   1200
atcacagatt cccgagcagg tgaagaaggc tcgatcaggg cagtggatca tgccgtgatc   1260
ggtggcgtcg tggcggtggt ggtgttcgcc atgctgtgct tgctcatcat tctggggcgc   1320
tattttgcca gacataaagg tacatacttc actcatgaag ccaaaggagc cgatgacgca   1380
gcagacgcag acacagctat aatcaatgca gaaggaggac agaacaactc cgaagaaaag   1440
aaagagtact tcatctagat cagccttttt gtttcaatga ggtgtccaac tggccctatt   1500
tagatgataa agagacagtg atattggaac ttgcgagaaa ttcgtgtgtt tttttatgaa   1560
tgggtggaaa ggtgtgagac tgggaaggct tgggatttgc tgtgtaaaaa aaaaaaaaat   1620
gttctttgga aagtacactc tgctgtttga cacctctttt ttcgtttgtt tgtttgttta   1680
atttttattt cttcctacca agtcaaactt ggatacttgg atttagtttc agtagattgc   1740
agaaaattct gtgccttgtt ttttgtttgt ttgttgcgtt cctttctttt ccccctttgt   1800
gcacatttat ttcctccctc taccccaatt tcggattttt tccaaaatct cccattttgg   1860
aatttgcctg ctgggattcc ttagactctt ttccttccct tttctgttct agtttttttac  1920
ttttgtttat ttttatggta actgctttct gttccaaatt cagtttcata aaaggagaac   1980
cagcacagct tagatttcat agttcagaat ttagtgtatc cataatgcat tcttctctgt   2040
tgtcgtaaag atttgggtga acaaacaatg aaaactcttt gctgctgccc atgtttcaaa   2100
tacttagagc agtgaagact agaaaattag actgtgattc agaaaatgtt ctgtttgctg   2160
tggaactaca ttactgtaca gggttatctg caagtgaggt gtgtcacaat gagattgaat   2220
ttcactgtct ttaattctgt atctgtagac ggctcagtat agatacccta cgctgtccag   2280
aaaggtttgg ggcagaaagg actcctcctt tttccatgcc ctaaacagac ctgacaggtg   2340
aggtctgttc cttttatata agtggacaaa ttttgagttg ccacaggagg ggaagtaggg   2400
aggggggaaa tacagttctg ctctggttgt ttctgttcca aatgattcca tccacctttc   2460
ccaatcggcc ttacttctca ctaatttgta ggaaaaagca agttcgtctg ttgtgcgaat   2520
gactgaatgg gacagagttg attttttttt ttttttcctt tgtgcttagt taggaaggca   2580
gtaggatgtg gcctgcatgt actgtatatt acagatattt gtcatgctgg gatttccaac   2640
tcgaatctgt gtgaaacttt cattccttca gatttggctt gacaaaggca ggaggtacaa   2700
aagaagggct ggtattgttc tcacactggt ctgctgtcgc tctcagttct cgataggtca   2760
gagcagaggt ggaaaaacag catgtacgga ttttcagtta cttaatcaaa actcaaatgt   2820
```

```
gagtgttttt atctttttac ctttcataca ctagccttgg cctctttcct cagccttaag   2880

aaccatctgc caaaaattac tgatcctcgc atgatggcag ccatagtgca tagctactaa   2940

aatcagtgac cttgaacata tcttagatgg ggagcctcgg gaaaaggtag aggagtcacg   3000

ttaccattta catgttttaa agaaagaagt gtggggattt tcactgaaac gtctaggaaa   3060

tctagaagta gtcctgaagg acagaaacta aactcttacc atatgtttgg taagactcca   3120

gactccagct aacagtccct atggaaagat ggcatcaaaa aagatagatc tatatatata   3180

tataaatata tattctatta cattttcagt gagtaatttt ggattttgca aggtgcattt   3240

ttactattgt tacattatgt ggaaaactta tgctgattta tttaaggggg aaaaagtgtc   3300

aactctttgt tatttgaaaa catgtttatt tttcttgtct ttattttaac ctttgataga   3360

accattgcaa tatgggggcc ttttgggaac ggactggtat gtaaaagaaa atccattatc   3420

gagcagcatt ttatttaccc ctcccctatc cctaggcact taaccaagac aaaaagccac   3480

aatgaacatc cctttttcaa tgaattttat aatctgcagc tctattccga gcccttagca   3540

cccattccga ccatagtata atcatatcaa agggtgagaa tcatttagca tgttgttgaa   3600

aggttttttt tcagttgttc tttttagaaa aaaagaaaaa caaaaacaaa aacaaaaaaa   3660

aaaaatcaca ccattgctca cagaattggc atctcatttt tgggacctcc catctttctg   3720

ttttgaaaag tgtacagtag tgcagtgttc ctgatgtaac tttatggctt acaatgttga   3780

catgtctcag gttcatgtgt tgcgattggt gttttccgtc tcaggtagat tgcaaagtgt   3840

aggccccaca cattggaaaa aataataata aaacaaagca aaaacaggaa attatggatt   3900

ttagttgtat attggtttat gtatttttttc ttaagtatac agtgcactgt ttgaaatgta   3960

ttgttgagta ttactttgta caggttgatc actttttttta gagtgaagaa agaacaaact   4020

tgttttttgt gtttttttaaa ggaatataaa ataatgaagg atgtataatt gatgccaaat   4080

aagcttgttc tttagtcaca ccgacgtctt atttttccct ttaggccagt tctgtttttta   4140

aggtgtacat ggacaatgtt acagtgtaag aaactccata tccatatgtt cccattcgca   4200

ttttgtattg gttcatgtat accattttta caaaaaaaaa aagaaaaaaa agaagtacta   4260

taaaatatct gtcttcttaa taaaaaaaaa ttaatgttac aaagtgaaaa aaaaaaaaaa   4320

aaaa                                                                 4324
```

<210> SEQ ID NO 15
<211> LENGTH: 1145
<212> TYPE: DNA
<213> ORGANISM: Homo sapiens

<400> SEQUENCE: 15

```
ggaggctgca gcagcggaag accccagtcc agatccagga ctgagatccc agaaccatga     60

acctggccat cagcatcgct ctcctgctaa cagtcttgca ggtctcccga gggcagaagg    120

tgaccagcct aacggcctgc ctagtggacc agagccttcg tctggactgc cgccatgaga    180

ataccagcag ttcacccatc cagtacgagt tcagcctgac ccgtgagaca aagaagcacg    240

tgctctttgg cactgtgggg gtgcctgagc acacataccg ctcccgaacc aacttcacca    300

gcaaatacaa catgaaggtc ctctacttat ccgccttcac tagcaaggac gagggcacct    360

acacgtgtgc actccaccac tctggccatt ccccacccat ctcctcccag aacgtcacag    420

tgctcagaga caaactggtc aagtgtgagg gcatcagcct gctggctcag aacacctcgt    480

ggctgctgct gctcctgctc tccctctccc tcctccaggc cacggatttc atgtccctgt    540

gactggtggg gcccatggag gagacaggaa gcctcaagtt ccagtgcaga gatcctactt    600
```

```
ctctgagtca gctgaccccc tccccccaat ccctcaaacc ttgaggagaa gtggggaccc    660

caccccctcat caggagttcc agtgctgcat gcgattatct acccacgtcc acgcggccac    720

ctcaccctct ccgcacacct ctggctgtct ttttgtactt tttgttccag agctgcttct    780

gtctggttta tttaggtttt atccttcctt ttctttgaga gttcgtgaag agggaagcca    840

ggattgggga cctgatggag agtgagagca tgtgaggggt agtgggatgg tggggtacca    900

gccactggag ggtcatcct tgcccatcgg gaccagaaac ctgggagaga cttggatgag    960

gagtggttgg gctgtgcctg ggcctagcac ggacatggtc tgtcctgaca gcactcctcg   1020

gcaggcatgg ctggtgcctg aagaccccag atgtgagggc accaccaaga atttgtggcc   1080

taccttgtga gggagagaac tgagcatctc cagcattctc agccacaacc aaaaaaaaaa   1140

aaaaa                                                               1145
```

<210> SEQ ID NO 16
<211> LENGTH: 5895
<212> TYPE: DNA
<213> ORGANISM: Homo sapiens

<400> SEQUENCE: 16

```
gcagttggtg aaactcctct gtctcccgct catcttttca ttgctcgttc ccctccttcc     60

cgcagacacc cggacctccc ctgggcgcca gctccgcggc tccaacgggt ccagaaacaa    120

gccggatttt tttttttct tcctggaaat tggctttggt gtgtgttgcc ctacctccct    180

cctccccctc ccacccacag cccccccccg gcctttttt tttttttttt tttttttgag    240

acatggcccg ggcagtggct cctggaagag gaacaagtgt gggaaaaggg agaggaagcc    300

ggagctaaat gacaggatgc aggcgacttg agacacaaaa agagaagcgt tcctctcgga    360

tccaggcatt gcctcgctgc tttcttttct ccaagacggg ctgaggattg tacagctcta    420

ggcggagttg gggctcttcg gatcgcttag attctcctct ttgctgcatt tccccccacg    480

tcctcgttct cccgcgtctg cctgcggacc cggagaaggg agaatggaga gggggctgcc    540

gctcctctgc gccgtgctcg ccctcgtcct cgcccccggcc ggcgcttttc gcaacgataa    600

atgtggcgat actataaaaa ttgaaagccc cgggtacctt acatctcctg gttatcctca    660

ttcttatcac ccaagtgaaa aatgcgaatg gctgattcag gctccggacc cataccagag    720

aattatgatc aacttcaacc ctcacttcga tttggaggac agagactgca agtatgacta    780

cgtggaagtc ttcgatggag aaaatgaaaa tggacatttt aggggaaagt tctgtggaaa    840

gatagcccct cctcctgttg tgtcttcagg gccatttctt tttatcaaat ttgtctctga    900

ctacgaaaca catggtgcag gattttccat acgttatgaa attttcaaga gaggtcctga    960

atgttcccag aactacacaa cacctagtgg agtgataaag tcccccggat tccctgaaaa   1020

atatcccaac agccttgaat gcacttatat tgtctttgcg ccaaagatgt cagagattat   1080

cctggaattt gaaagctttg acctggagcc tgactcaaat cctccagggg ggatgttctg   1140

tcgctacgac cggctagaaa tctgggatgg attccctgat gttggccctc acattgggcg   1200

ttactgtgga cagaaaacac caggtcgaat ccgatcctca tcgggcattc tctccatggt   1260

tttttacacc gacagcgcga tagcaaaaga aggtttctca gcaaactaca gtgtcttgca   1320

gagcagtgtc tcagaagatt tcaaatgtat ggaagctctg ggcatggaat caggagaaat   1380

tcattctgac cagatcacag cttcttccca gtatagcacc aactggtctg cagagcgctc   1440

ccgcctgaac taccctgaga atgggtggac tcccggagag gattcctacc gagagtggat   1500

acaggtagac ttgggccttc tgcgctttgt cacggctgtc gggacacagg gcgccatttc   1560
```

```
aaaagaaacc aagaagaaat attatgtcaa gacttacaag atcgacgtta gctccaacgg   1620
ggaagactgg atcaccataa aagaaggaaa caaacctgtt ctctttcagg gaaacaccaa   1680
ccccacagat gttgtggttg cagtattccc caaaccactg ataactcgat ttgtccgaat   1740
caagcctgca acttgggaaa ctggcatatc tatgagattt gaagtatacg gttgcaagat   1800
aacagattat ccttgctctg gaatgttggg tatggtgtct ggacttattt ctgactccca   1860
gatcacatca tccaaccaag ggacagaaa ctggatgcct gaaaacatcc gcctggtaac   1920
cagtcgctct ggctgggcac ttccacccgc acctcattcc tacatcaatg agtggctcca   1980
aatagacctg gggggaggaga agatcgtgag ggcatcatc attcagggtg ggaagcaccg   2040
agagaacaag gtgttcatga ggaagttcaa gatcgggtac agcaacaacg gctcggactg   2100
gaagatgatc atggatgaca gcaaacgcaa ggcgaagtct tttgagggca acaacaacta   2160
tgatacacct gagctgcgga cttttccagc tctctccacg cgattcatca ggatctaccc   2220
cgagagagcc actcatggcg gactggggct cagaatggag ctgctgggct gtgaagtgga   2280
agcccctaca gctggaccga ccactcccaa cgggaacttg gtggatgaat gtgatgacga   2340
ccaggccaac tgccacagtg gaacaggtga tgacttccag ctcacaggtg gcaccactgt   2400
gctggccaca gaaaagccca cggtcataga cagcaccata caatcagagt ttccaacata   2460
tggttttaac tgtgaatttg gctggggctc tcacaagacc ttctgccact gggaacatga   2520
caatcacgtg cagctcaagt ggagtgtgtt gaccagcaag acgggaccca ttcaggatca   2580
cacaggagat ggcaacttca tctattccca agctgacgaa aatcagaagg gcaaagtggc   2640
tcgcctggtg agccctgtgg tttattccca gaactctgcc cactgcatga ccttctggta   2700
tcacatgtct gggtcccacg tcggcacact cagggtcaaa ctgcgctacc agaagccaga   2760
ggagtacgat cagctggtct ggatggccat tggacaccaa ggtgaccact ggaaggaagg   2820
gcgtgtcttg ctccacaagt ctctgaaact ttatcaggtg attttcgagg gcgaaatcgg   2880
aaaaggaaac cttggtggga ttgctgtgga tgacattagt attaataacc acatttcaca   2940
agaagattgt gcaaaaccag cagacctgga taaaaagaac ccagaaatta aaattgatga   3000
aacagggagc acgccaggat acgaaggtga aggagaaggt gacaagaaca tctccaggaa   3060
gccaggcaat gtgttgaaga ccttagaccc catcctcatc accatcatag ccatgagtgc   3120
cctgggggtc ctcctggggg ctgtctgtgg ggtcgtgctg tactgtgcct gttggcataa   3180
tgggatgtca gaaagaaact tgtctgccct ggagaactat aactttgaac ttgtggatgg   3240
tgtgaagttg aaaaaagaca aactgaatac acagagtact tattcggagg catgaaggca   3300
gacagagatg aaaagacagt caaaggacgg aagtggaagg acgggagtga gctggggagc   3360
tgttgatctt tcactataca ggctgggaag tgtgttgatg accactgagc caggcttttc   3420
tcaggagctt caatgagtat ggccgacaga catggacaag gagctgtgtt caccatcgga   3480
ctcatgtgca gtcagctttt ttcctgttgg tttcatttga ataatcagat gctggtgttg   3540
agaccaagta tgattgacat aatcattcat ttcgacccct cctgcccctc tctctctctc   3600
tcctctcccc tttgtggatt ctttttggaa actgagcgaa atccaagatg ctggcaccaa   3660
gcgtattccg tgtggccctt tggatggaca tgctacctga aacccagtgc ccagaatata   3720
ctagaatcac cgcatttcag tggactcctg aagttgtact tgtgtataat tgcccgcgtc   3780
gtgcataggc aaagaaggat taggctgttt tctttttaaa gtactgtagc ctcagtactg   3840
gtgtagtgtg tcagctctgt ttacgaagca atactgtcca gttttcttgc tgtttttccg   3900
gtgttgtact aaacctcgtg cttgtgaact ccatacagaa aacggtgcca tccctgaaca   3960
```

cggctggcca ctgggtatac tgctgacaac cgcaacaaca aaaacacaaa tccttggcac 4020
tggctagtct atgtcctctc aagtgccttt ttgtttgtac tggttcattg tgttacatta 4080
acgacccact ctgcttcttg ctggtgaaag ccctgctctt taatcaaact ctggtggccc 4140
actgactaag aagaaagttt attttcgtgt gagatgccag cccctccggg caggcaaggg 4200
ctctgaagat ttggcaacgt ggcttaattg ttctgctttt tctgtagttc aatttcatgt 4260
ttcttgaccc ttttgtataa agctacaata ttctctctta ttgttctttc atatggaatg 4320
tattttcaaa tgtaaactct cttctctttc tctctcctat ctctctgtct tttttctctc 4380
ttagaattgg aggatttgcc attgtccagg aaagaaactt gcagctttaa cctgctggga 4440
atggcaaacg attttactag actttatgtt taaaaataaa taaataaggg aaattcctaa 4500
ctttgccctc caaagtctaa ctttggtttt cttgttaact ggttaaagtg acagtatctt 4560
ttttccttat ctattctatt caaaatgacc tttgatagaa atgttggcat ttagtagaaa 4620
tagtgataag ttgaggaaag aaataataca aattggcttt caagtgagac ccaaaggaag 4680
aactggataa aatcttccaa atccaaaagc atgagatttt tctatccaaa tatgcaaaaa 4740
tgacccaaga gaactttctt attttgctac tgagtcacac aagggaagtg gaaggaagaa 4800
cagttaattt aagaatgaaa ctataaatcc tgatgcctgg gggtcaagta ttttaagata 4860
agagggggaa aaacacataa agtcaaacaa atgttttaaa aattcataac agcaaccttg 4920
aaaaaataga cttaaatgaa tgcttctaga aacttccagc ggctcacaaa gaataagcct 4980
gccttagggc tggcaacatc taagcctcta acagcacagg gaagcaaata tcttaccagg 5040
cagcctatga attaacccaa agaagctttg gttggttttg gtggattttt atcatgccat 5100
gttggacatg agatttttta gatcttcctt cccacattgc tagacgtctc actcaaagac 5160
atttgttggg agtcacattt gcatcataga cgagacagtc cattcatctt agttaaattg 5220
gattgagaat gccttttgtt tccaggaaaa tattgatcac catgaaagaa gaatagtttt 5280
ttgtccccag agacattcat ttagttgata taatcctacc agaaggaaag cactaagaaa 5340
cactcgtttg ttgtttttaa aggcaacaga cttaaagttg tcctcagcca aggaaaaatg 5400
atactgcaac tttaaaattt aaagtatctt gcactgataa atatatttaa aaattatatg 5460
tttataaagt tattaatttg taaaggcagt gttacaaaat gttcagttta tattgtttta 5520
gattgttttg taatttttaa aggtgtaaaa taacatattt tttctttatg gaaatctata 5580
aaactttctg tagtaaaatg ttttcatttt actggtatat tattgcttca tgttttgtac 5640
catcataaga ttttgtgcag attttttta cagaaattat tattttctat gacaatatga 5700
cacttgtaaa ttgttgtttc aaaatgaaca gcgaagcctt aactttaaat gacatttgta 5760
ttctcagaca ctgagtagca taaaaaccac atagaactga actgtaactt aaattccaaa 5820
ctatgactac tacattccaa agaaacagtt gaattaaaca ttttcataaa atatcccaca 5880
aaaaaaaaaa aaaaa 5895

<210> SEQ ID NO 17
<211> LENGTH: 2478
<212> TYPE: DNA
<213> ORGANISM: Homo sapiens

<400> SEQUENCE: 17
gcagttggtg aaactcctct gtctcccgct catcttttca ttgctcgttc ccctccttcc 60
cgcagacacc cggacctccc ctgggcgcca gctccgcggc tccaacgggt ccagaaacaa 120
gccggatttt tttttttct tcctggaaat tggctttggt gtgtgttgcc ctacctccct 180

```
cctcccctc ccacccacag ccccccccg gcctttttt tttttttttt tttttttgag    240
acatggcccg ggcagtggct cctggaagag gaacaagtgt gggaaaaggg agaggaagcc    300
ggagctaaat gacaggatgc aggcgacttg agacacaaaa agagaagcgt tcctctcgga    360
tccaggcatt gcctcgctgc tttcttttct ccaagacggg ctgaggattg tacagctcta    420
ggcggagttg gggctcttcg gatcgcttag attctcctct ttgctgcatt tccccccacg    480
tcctcgttct cccgcgtctg cctgcggacc cggagaaggg agaatggaga gggggctgcc    540
gctcctctgc gccgtgctcg ccctcgtcct cgccccggcc ggcgcttttc gcaacgataa    600
atgtggcgat actataaaaa ttgaaagccc cgggtacctt acatctcctg gttatcctca    660
ttcttatcac ccaagtgaaa aatgcgaatg gctgattcag gctccggacc catacccagag    720
aattatgatc aacttcaacc ctcacttcga tttggaggac agagactgca agtatgacta    780
cgtggaagtc ttcgatggag aaaatgaaaa tggacatttt aggggaaagt tctgtggaaa    840
gatagcccct cctcctgttg tgtcttcagg gccatttctt tttatcaaat ttgtctctga    900
ctacgaaaca catggtgcag gattttccat acgttatgaa attttcaaga gaggtcctga    960
atgttcccag aactacacaa cacctagtgg agtgataaag tcccccggat tccctgaaaa   1020
atatcccaac agccttgaat gcacttatat tgtctttgcg ccaaagatgt cagagattat   1080
cctggaattt gaaagctttg acctggagcc tgactcaaat cctccagggg ggatgttctg   1140
tcgctacgac cggctagaaa tctgggatgg attccctgat gttggccctc acattgggcg   1200
ttactgtgga cagaaaacac caggtcgaat ccgatcctca tcgggcattc tctccatggt   1260
tttttacacc gacagcgcga tagcaaaaga aggtttctca gcaaactaca gtgtcttgca   1320
gagcagtgtc tcagaagatt tcaaatgtat ggaagctctg ggcatggaat caggagaaat   1380
tcattctgac cagatcacag cttcttccca gtatagcacc aactggtctg cagagcgctc   1440
ccgcctgaac taccctgaga atgggtggac tcccggagag gattcctacc gagagtggat   1500
acaggtagac ttgggccttc tgcgctttgt cacggctgtc gggacacagg gcgccatttc   1560
aaaagaaacc aagaagaaat attatgtcaa gacttacaag atcgacgtta gctccaacgg   1620
ggaagactgg atcaccataa aagaaggaaa caaacctgtt ctctttcagg gaaacaccaa   1680
ccccacagat gttgtggttg cagtattccc caaaccactg ataactcgat ttgtccgaat   1740
caagcctgca acttgggaaa ctggcatatc tatgagattt gaagtatacg gttgcaagat   1800
aacagattat ccttgctctg gaatgttggg tatggtgtct ggacttattt ctgactccca   1860
gatcacatca tccaaccaag ggacagaaa ctggatgcct gaaaacatcc gcctggtaac   1920
cagtcgctct ggctgggcac ttccacccgc acctcattcc tacatcaatg agtggctcca   1980
aatagacctg gggaggaga agatcgtgag ggcatcatc attcagggtg ggaagcaccg   2040
agagaacaag gtgttcatga ggaagttcaa gatcgggtac agcaacaacg gctcggactg   2100
gaagatgatc atggatgaca gcaaacgcaa ggcgaagtct tttgagggca acaacaacta   2160
tgatacacct gagctgcgga cttttccagc tctctccacg cgattcatca ggatctaccc   2220
cgagagagcc actcatggcg gactggggct cagaatggag ctgctgggct gtgaagtgga   2280
agcccctaca gctggaccga ccactcccaa cgggaacttg gtggatgaat gtgatgacga   2340
ccaggccaac tgccacagtg gaacaggtga tgacttccag ctcacaggtg gcaccactgt   2400
gctggccaca gaaaagccca cggtcataga cagcaccata caatcaggta tcaaataaaa   2460
tacgaaatgt gacagatt                                                 2478
```

<210> SEQ ID NO 18
<211> LENGTH: 2373
<212> TYPE: DNA
<213> ORGANISM: Homo sapiens

<400> SEQUENCE: 18

```
gcagttggtg aaactcctct gtctcccgct catcttttca ttgctcgttc ccctccttcc     60
cgcagacacc cggacctccc ctgggcgcca gctccgcggc tccaacgggt ccagaaacaa    120
gccggatttt tttttttct tcctggaaat tggctttggt gtgtgttgcc ctacctccct    180
cctcccctc ccacccacag cccccccccg gccttttttt tttttttttt tttttttgag    240
acatggcccg ggcagtggct cctggaagag gaacaagtgt gggaaaaggg agaggaagcc    300
ggagctaaat gacaggatgc aggcgacttg agacacaaaa agagaagcgt tcctctcgga    360
tccaggcatt gcctcgctgc tttcttttct ccaagacggg ctgaggattg tacagctcta    420
ggcggagttg gggctcttcg gatcgcttag attctcctct ttgctgcatt tccccccacg    480
tcctcgttct cccgcgtctg cctgcggacc cggagaaggg agaatggaga gggggctgcc    540
gctcctctgc gccgtgctcg ccctcgtcct cgccccggcc ggcgcttttc gcaacgataa    600
atgtggcgat actataaaaa ttgaaagccc cgggtacctt acatctcctg gttatcctca    660
ttcttatcac ccaagtgaaa aatgcgaatg gctgattcag gctccggacc cataccagag    720
aattatgatc aacttcaacc ctcacttcga tttggaggac agagactgca agtatgacta    780
cgtggaagtc ttcgatggag aaaatgaaaa tggacatttt aggggaaagt tctgtggaaa    840
gatagcccct cctcctgttg tgtcttcagg gccatttctt tttatcaaat ttgtctctga    900
ctacgaaaca catggtgcag gattttccat acgttatgaa attttcaaga gaggtcctga    960
atgttcccag aactacacaa cacctagtgg agtgataaag tcccccggat tccctgaaaa   1020
atatcccaac agccttgaat gcacttatat tgtctttgcg ccaaagatgt cagagattat   1080
cctggaattt gaaagctttg acctggagcc tgactcaaat cctccagggg ggatgttctg   1140
tcgctacgac cggctagaaa tctgggatgg attccctgat gttggccctc acattgggcg   1200
ttactgtgga cagaaaacac caggtcgaat ccgatcctca tcgggcattc tctccatggt   1260
tttttacacc gacagcgcga tagcaaaaga aggtttctca gcaaactaca gtgtcttgca   1320
gagcagtgtc tcagaagatt tcaaatgtat ggaagctctg ggcatggaat caggagaaat   1380
tcattctgac cagatcacag cttcttccca gtatagcacc aactggtctg cagagcgctc   1440
ccgcctgaac taccctgaga atgggtggac tcccggagag gattcctacc gagagtggat   1500
acaggtagac ttgggccttc tgcgctttgt cacggctgtc gggacacagg gcgccatttc   1560
aaaagaaacc aagaagaaat attatgtcaa gacttacaag atcgacgtta gctccaacgg   1620
ggaagactgg atcaccataa aagaaggaaa caaacctgtt ctctttcagg gaaacaccaa   1680
ccccacagat gttgtggttg cagtattccc caaaccactg ataactcgat ttgtccgaat   1740
caagcctgca acttgggaaa ctggcatatc tatgagattt gaagtatacg gttgcaagat   1800
aacagattat ccttgctctg gaatgttggg tatggtgtct ggacttattt ctgactccca   1860
gatcacatca tccaaccaag gggacagaaa ctggatgcct gaaaacatcc gcctggtaac   1920
cagtcgctct ggctgggcac ttccacccgc acctcattcc tacatcaatg agtggctcca   1980
aatagacctg gggaggaga agatcgtgag ggcatcatc attcagggtg ggaagcaccg   2040
agagaacaag gtgttcatga ggaagttcaa gatcgggtac agcaacaacg gctcggactg   2100
```

-continued

```
gaagatgatc atggatgaca gcaaacgcaa ggcgaagtct tttgagggca acaacaacta   2160

tgatacacct gagctgcgga cttttccagc tctctccacg cgattcatca ggatctaccc   2220

cgagagagcc actcatggcg gactggggct cagaatggag ctgctgggct gtgaagtgga   2280

aggtggcacc actgtgctgg ccacagaaaa gcccacggtc atagacagca ccatacaatc   2340

aggtatcaaa taaaatacga aatgtgacag att                                2373
```